US012225917B2

(12) United States Patent
Yu et al.

(10) Patent No.: US 12,225,917 B2
(45) Date of Patent: Feb. 18, 2025

(54) BERBERINE ALKALOID FORMULATIONS IN THE PREVENTION AND/OR TREATMENT OF INFECTIOUS DISEASE

(71) Applicant: IRP Health Pty Ltd, Mount Waverley (AU)

(72) Inventors: David Xiang Yu, Frankston South (AU); Zhicheng Xiao, Langwarrin (AU); Colin William Pouton, Alphington (AU); Zhiyong He, Pakenham (AU)

(73) Assignee: IRP HEALTH PTY LTD, Mount Waverly (AU)

( * ) Notice: Subject to any disclaimer, the term of this patent is extended or adjusted under 35 U.S.C. 154(b) by 1038 days.

(21) Appl. No.: 16/499,163

(22) PCT Filed: Mar. 28, 2018

(86) PCT No.: PCT/AU2018/050288
§ 371 (c)(1),
(2) Date: Sep. 27, 2019

(87) PCT Pub. No.: WO2018/176093
PCT Pub. Date: Oct. 4, 2018

(65) Prior Publication Data
US 2021/0329946 A1   Oct. 28, 2021

(30) Foreign Application Priority Data

Mar. 28, 2017 (AU) ................................. 2017901105
Aug. 15, 2017 (AU) ................................. 2017903261

(51) Int. Cl.
*A23K 20/132* (2016.01)
*A23K 50/30* (2016.01)
(Continued)

(52) U.S. Cl.
CPC ............ *A23K 20/132* (2016.05); *A23K 50/30* (2016.05); *A23K 50/75* (2016.05); *A61K 9/0053* (2013.01); *A61K 31/4375* (2013.01); *A61P 31/04* (2018.01)

(58) Field of Classification Search
CPC ...... A23K 20/132; A23K 50/30; A23K 50/75; A61P 31/04; A61K 9/0053; A61K 31/4375
See application file for complete search history.

(56) References Cited

U.S. PATENT DOCUMENTS

2007/0027176 A1   2/2007   Jin et al.
2007/0098649 A1   5/2007   Wu et al.
2017/0196240 A1   7/2017   Park et al.

FOREIGN PATENT DOCUMENTS

CN   102151260 A   8/2011
CN   102475193 A   5/2012
(Continued)

OTHER PUBLICATIONS

Zhang et al., "The effects of Forsythia suspensa extract and berberine on growth performance, immunity, antioxidant activities, and intestinal microbiota in broilers under high stocking density". Poultry Science 92:1981-1988. (Year: 2013).*

(Continued)

*Primary Examiner* — Donald R Spamer
*Assistant Examiner* — Assaf Zilbering
(74) *Attorney, Agent, or Firm* — HOLLAND & HART LLP

(57) ABSTRACT

This invention relates to berberine alkaloids, formulations thereof, and their use in the prevention and/or treatment of infectious disease in animals, particularly *Lawsonia* infection. In particular, the invention relates to berberine alkaloids, formulations thereof, and their application as antimicrobial agents in the prevention and/or treatment of (Continued)

infectious disease including bacterial, viral, parasitic or fungal infections, and for improving feed conversion ratio in food-producing animals. Also described is the use of berberine alkaloids as feed preservatives, added to feed compositions, and used in combination with further agents suitable for treating infectious disease.

9 Claims, 30 Drawing Sheets

(51) Int. Cl.
    *A23K 50/75*      (2016.01)
    *A61K 9/00*      (2006.01)
    *A61K 31/4375*      (2006.01)
    *A61P 31/04*      (2006.01)

(56) References Cited

FOREIGN PATENT DOCUMENTS

| | | |
|---|---|---|
| CN | 103768252 A | 5/2014 |
| CN | 104605164 A | 5/2015 |
| CN | 105056121 A | 11/2015 |
| CN | 106309464 A | 1/2017 |
| CN | 106490337 A | 3/2017 |
| WO | 2002021933 A2 | 3/2002 |
| WO | 2013182038 A1 | 12/2013 |
| WO | 2015186956 A1 | 12/2015 |

OTHER PUBLICATIONS

Tummaruk et al., "The use of herbal medicine as an alternative antimicrobial in the feed of post-weaning piglets—A filed trial". Journal of Applied Animal science vol. 2 No. 3 Sep.-Dec. 2009. (Year: 2009).*
Murphy et al., "EMA and EFSA Joint Scientific Opinion on measures to reduce the need to use antimicrobial agents" EFSA Journal 2017;15(1):4666 (Year: 2017).*
Su et al., "Antibacterial Activities and Antibacterial Mechanism of Polygonum cuspidatum Extracts against nosocomial Drug-Resistant Pathogens". Molecules 2015, 20, 11119-11130. (Year: 2015).*
Malik, T.A. et al "Synergistic approach for treatment of chicken coccidiosis using berberine—A plant natural product." Microbial Pathogenesis, vol. 93, p. 56-62. 2016.
International Search Report for International Application No. PCT/AU2018/050288, mailed Jul. 3, 2018, 11 pages.
R Cutler, B Gleeson, S Page, J Norris, G Browning, Australian Veterinary Association Ltd and Animal Medicines Australia (Apr. 12, 2020) "Antimicrobial prescribing guidelines for pigs"; 60 pgs.

* cited by examiner

Fibrauretin (palmatine)

Palmatine chloride

Matrine

Oxymatrine

Arecoline

Arecoline hydrobromide

Baicalin

Baicalein

Anemonin

Andrographolide

Piceid

Hyperaemia    Intestinal translucency

BERBERINE ALKALOID FORMULATIONS IN THE PREVENTION AND/OR TREATMENT OF INFECTIOUS DISEASE

TECHNICAL FIELD OF THE INVENTION

This invention relates to berberine alkaloids, formulations thereof, and their use in the prevention and/or treatment of infectious disease in animals. In particular, the invention relates to berberine alkaloids, formulations thereof, and their use in the prevention and/or treatment of infectious disease including bacterial, viral, parasitic or fungal infections in food-producing animals.

BACKGROUND

Antibiotic use has been a staple in animal production worldwide for decades. It is estimated that the world uses about 63,000 tons of antibiotics each year to raise cows, chickens and pigs, which is roughly twice that of antibiotics prescribed by doctors globally to fight infections in people, with current trends suggesting world consumption of antibiotics in animals will go up by two-thirds in the next 20 years.

Antibiotics have been supplemented to animal and poultry feed to not only treat and control infections, but also as growth promoters at low doses, and are considered to improve the quality of the product, resulting in a lower percentage of fat and a higher protein content in the meat. According to the National Office of Animal Health (NOAH, 2001), they are used to "help growing animals digest their food more efficiently, get maximum benefit from it and allow them to develop into strong and healthy individuals", leading to economic advantages for farmers. It is therefore important to increase and develop the armamentarium of agents that have the potential to act as antibiotics to fight infectious disease and which are cost effective.

Antimicrobial resistance (AMR) is a natural process whereby microbes evolve to be able to resist the action of drugs, making them ineffective. This leads to antibiotics becoming less effective over time and in extreme cases, ultimately useless. AMR has increasingly become a problem because the pace at which new antibiotics are discovered has slowed dramatically and consequently there are a very limited number of new drugs. Meanwhile, antibiotic use has risen exponentially increasing the development of resistance.

Recently, the use of antibiotics in food-producing animals has once again come under scrutiny, with growing concerns that their overuse contributes to the spread of antibiotic-resistance genes by promoting the selection of antibiotic-resistant bacteria in animals. In addition, waste materials from animals may contain antibiotic residues, resulting in their wider dissemination in the environment. These are major problems of intensive farming methods and the issues caused by their use are largely those of developed rather than developing countries.

Antimicrobial resistance (AMR) threatens the effective prevention and treatment of an ever-increasing range of infections caused by bacteria, parasites, viruses and fungi. AMR is an increasingly serious threat to global public health that requires action across all government sectors and society. The wide and overuse of antibiotics in food-producing animals contributes to the emergence of antibiotic-resistant bacteria which can contaminate the food and then consumers who in turn can then develop antibiotic-resistant infections. FIG. 1 depicts the spread of AMR from food-producing animal to human.

The fear is the overuse of antibiotics in food-producing animals leading to the spread of drug-resistant bacteria to humans and then in turn the overuse of antibiotics in humans will and has given rise to 'superbugs'-bacteria that are resistant to several classes of antibiotics. Already, it has been estimated that superbugs have caused more than 320,000 deaths each year in China and the US with the death toll expected to exceed 10 million by year 2050 and have cost the world over 100 trillion USD.

The global burden of infections resistant to existing antimicrobial medicines is growing at an alarming rate. Methicillin-resistant *Staphylococcus aureus* (MRSA) and *Klebsiella pneumoniae* are a major cause of hospital-acquired infections. *K. pneumonia*, which are common intestinal bacteria, have become resistant to even last resort treatment by β-lactam carbapenem antibiotics in some countries. In many parts of the world, treatment of urinary tract infections caused by *E. coli* bacteria is now ineffective because of resistance to fluoroquinolone antibiotics.

Use of B-lactam antibiotics and fluoroquinolones can lead to secondary infection and further complications such as overgrowth of *Clostridium difficile* (CD). CD is a bacterium that can cause symptoms ranging from diarrhea to life-threatening inflammation of the colon. Illness from CD most commonly affects older adults often in long-term care facilities and typically occurs after use of antibiotic medications. However, studies show increasing rates of CD infection among people traditionally not considered high risk, such as younger and healthy individuals without a history of antibiotic use or exposure to health care facilities. Each year in the United States, about a half million people get sick as a result of release of CD toxins, and in recent years, CD infections have become more frequent, severe and difficult to treat with the rise of antimicrobial resistance. Ironically, the standard treatment for CD is another antibiotic: metronidazole for mild to moderate infection: vancomycin for more severe infection. However, up to 20 percent of people with CD get sick again. After two or more recurrences, rates of further recurrence increase up to 65 percent.

Patients with infections caused by drug-resistant bacteria are at an increased risk of worse clinical outcomes and death, and consume more health-care resources than patients infected with non-resistant strains of the same bacteria. Antimicrobial resistance is a complex problem that affects all of society and is driven by many interconnected factors. Single, isolated interventions have limited impact. Coordinated action is required to minimize the emergence and spread of antimicrobial resistance. It is important to develop new antimicrobial drugs as alternatives to combat the world wide resistance problems facing human and animal health.

Major government regulators are already now implementing serious new directives and legislation in controlling the use of antibiotics in food-producing animals to reduce selection of resistance, including the European Union, FDA, Australia's Department of Agriculture and Health. Major companies in the food industries, such as McDonalds and Wal-Mart, are proposing their own initiatives to reduce the use of antibiotics in food.

The phasing out or banning of antibiotic use in animals will and has led to a number of consequences. The Animal Health Institute of America estimates that, without the use of growth promoting antibiotics, the USA would require an additional 452 million chickens, 23 million more cattle and 12 million more pigs to reach the levels of production attained by the current practices, resulting in greater economic burden for the farming industry.

More worryingly, the reduction or withdrawal of antibiotics and changes in farming practices has resulted in some animal diseases becoming more widespread and prevalent: for example Necrotic Enteritis in poultry. This is reported by countries in Europe such as France and Scandinavia, where the banning of antibiotic growth promoters was accompanied by a dramatic increase in Necrotic Enteritis incidence, indicating antibiotic growth promoters had a prophylactic effect in controlling the disease. With more countries implementing policies to reduce antibiotic usage, the current cost of Necrotic Enteritis for the international poultry industry estimated to be approximately two billion US dollars per annum, is projected to rise even further. Other diseases cause significant loss to the poultry industry such as Coccidiosis. Spotty Liver Disease has become a major cause of mortality in egg layers and reduces egg production.

The reduction or withdrawal of antibiotic use and changes in farming practice has also affected the pig industry with diseases becoming more widespread and prevalent. Outbreaks of diarrhoea associated with Enterotoxigenic *E. coli* and swine dysentery associated with *Brachyspira* are responsible for high mortality and morbidity in pigs. Also damaging to the pig industry is the Ileitis group of conditions which are associated with the bacterium *Lawsonia intracellularis* and affect the small intestine. The group of conditions includes porcine intestinal adenopathy, necrotic enteritis, regional ileitis and proliferative hemorrhagic enteropathy.

*Salmonellosis* is one of the most common and widely distributed food-poisoning and is caused by the bacteria *salmonella*. It is estimated that tens of millions of human cases occur worldwide every year and the disease results in more than hundred thousand deaths. Antimicrobial resistance in *Salmonella* serotypes has been a global problem. Surveillance data demonstrated an obvious increase in overall antimicrobial resistance among salmonellae from 20%-30% in the early 1990s to as high as 70% in some countries at the turn of the century. *Salmonella* lives in the intestines of husbandry animals (especially chicken and cattle). It can be found in water, food, or on surfaces that have been contaminated with the feces of infected animals or humans (FIG. 2 depicts aspects of *Salmonella* infection and food poisoning).

Campylobacteriosis is a gastrointestinal disease caused by bacteria called *Campylobacter* (CB) and a major cause of foodborne illness. CB is mainly spread to humans by eating or drinking contaminated food (mainly poultry), water or unpasteurised milk. CB can also be spread through contact with infected people, or from contact with cats, dogs and farm animals that carry the bacteria. FIG. 3 shows the epidemiology.

Most people who become infected with CB will get diarrhoea, cramping, abdominal pain, and fever that lasts from one to two weeks. Symptoms usually develop within 2 to 5 days after infection. The diarrhoea may contain blood or mucous. In rare cases, CB can enter the bloodstream and cause more serious disease. Anyone can get campylobacteriosis, although very young children, the elderly, people with poor immunity and people who work with farm animals are at greater risk of infection. Treatment usually involves rehydration, but in severe or complicated cases, antibiotics such as Erythromycin are prescribed to reduce illness duration.

More specifically, there is a continued occurrence of CB contamination of poultry carcass/meat. Methods to control CB contamination have been focused at the processing plant through washing and evisceration. However, it is thought that if CB colonisation can be controlled in the birds' intestinal tract, prior to slaughter, then contamination of the processed birds was reduced.

The forced reduction or withdrawal of antibiotics leading a move to the 'post-antibiotic era' has resulted in the need to consider and develop alternatives to treat, control and protect food-producing animals (and humans) from disease. Currently, there is a need for medicaments including medicated feeds that may be used to alleviate the problems associated with the reduction or withdrawal of antibiotics and the consequential accompanying disease outbreaks. To date, no single cost-effective preventive or therapeutic agent that can substitute for antibiotics in animal feeds has been found.

SUMMARY OF INVENTION

The present disclosure relates to a method for the prevention and/or treatment of an infectious disease in an animal, wherein the method comprises administering a berberine alkaloid to the animal.

The present disclosure also relates to an animal feed comprising a berberine alkaloid and an animal foodstuff, wherein the berberine alkaloid is in an amount of about 0.001% w/w to 2% w/w of the animal foodstuff.

The present disclosure also relates to a dosing regimen comprising administering a berberine alkaloid or an animal feed disclosed herein, wherein the berberine alkaloid or animal feed is administered for 1 to 6 weeks and in an amount effective to prevent and/or treat an infectious disease in an animal.

The present disclosure also relates to a method for the reduction of feed conversion ratio in a food-producing animal, wherein the method comprises the step of administering a berberine alkaloid or an animal feed disclosed herein to the food-producing animal.

The present disclosure also relates to a method for preventing or treating an infectious disease in an animal comprising administering an animal feed disclosed herein.

The present disclosure also relates to a method for preventing or treating an infectious intestinal disease in an animal comprising administering an animal feed disclosed herein.

The present disclosure also relates to a method for preventing or treating an infectious disease caused by *Eimeria* in an animal comprising administering an animal feed disclosed herein.

The present disclosure also relates to a method for preventing or treating an infectious disease caused by bacteria from the genus *Clostridium* in an animal comprising administering an animal feed disclosed herein, wherein the bacteria are *C. perfringens*.

The present disclosure also relates to use of a berberine alkaloid in the preparation of a medicament for the prevention and/or treatment of:
   an infectious disease in an animal;
   an infectious intestinal disease in an animal;
   an infectious disease caused by *Eimeria* in an animal; or
   an infectious disease caused by bacteria from the genus *Clostridium*, wherein the bacteria are *C. perfringens*.

The present disclosure also relates to use of a berberine alkaloid in the prevention and/or treatment of:
   an infectious disease in an animal;
   an infectious intestinal disease in an animal;
   an infectious disease caused by *Eimeria* in an animal; or an infectious disease caused by bacteria from the genus *Clostridium*, wherein the bacteria are *C. perfringens*.

The present disclosure also relates to a berberine alkaloid for use in the prevention and/or treatment of:

an infectious disease in an animal;

an infectious intestinal disease in an animal;

an infectious disease caused by *Eimeria* in an animal; or an infectious disease caused by bacteria from the genus *Clostridium*, wherein the bacteria are *C. perfringens*.

Definitions

As used herein the term "acceptable excipient" refers to a solid or liquid filler, carrier, diluent or encapsulating substance that may be safely used in administration. Depending upon the particular route of administration, a variety of carriers, well known in the art may be used. These carriers or excipients may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline, and pyrogen-free water. Excipients are discussed, for example, in Remington: The Science and Practice of Pharmacy, $21^{st}$ Edition, Lippincott Williams and Wilkins, 2005.

As used herein the term "acceptable salt" refers to salts which are toxicologically safe for systemic administration. Acceptable salts, including acceptable acidic/anionic or basic/cationic are described in P. L. Gould, International Journal of Pharmaceutics, 1986 November, 33 (1-3), 201-217: S. M. Berge et al., Journal of Pharmaceutical Science, 1977 January, 66 (1), 1: P. Heinrich Stahl, Camille G. Wermuth (Eds.), Handbook of Pharmaceutical Salts: Properties, Selection and Use, Second Revised Edition, Wiley, 2011. Acceptable salts of the acidic or basic compounds of the invention can of course be made by conventional procedures (such as reacting a free acid with the desired salt-forming base or reacting a free base with the desired salt-forming acid).

Acceptable salts of acidic compounds include salts with cations and may be selected from alkali or alkaline earth metal salts, including, sodium, lithium, potassium, calcium, magnesium and the like, as well as non-toxic ammonium, quaternary ammonium, and amine cations, including, but not limited to ammonium, tetramethylammonium, tetraethylammonium, methylamine, dimethylamine, trimethylamine, triethylamine, ethylamine, triethanolamine and the like, and salts with organic bases. Suitable organic bases include N-methyl-D-glucamine, arginine, benzathine, diolamine, olamine, procaine and tromethamine.

Acceptable salts of basic compounds include salts with anions and may be selected from organic or inorganic acids. Suitable anions include acetate, acylsulfates, acylsulfonates, adipate, ascorbate, benzoate, besylate, bromide, camsylate, caprate, caproate, caprylate, chloride, citrate, docusate, edisylate, estolate, formate, fumarate, gluceptate, gluconate, glucuronate, hippurate, hyclate, hydrobromide, hydrochloride, iodide, isethionate, lactate, lactobionate, laurate, malate, maleate, mesylate, methylbromide, methylsulfate, napsylate, nitrate, octanoate, oleate, pamoate, phosphate, polygalacturonate, salicylate, stearate, succinate, sulfate, sulfonate, sulfosalicylate, tannate, tartrate, terephthalate, tosylate, triethiodide and the like.

Berberine is a positively charged quaternary ammonium cation. Acceptable salts of berberine include without limitation chloride, hemisulfate and iodide salts.

As used herein "acceptable solvent" is a solvent which for the purpose of the disclosure may not interfere with the biological activity of the solute. Examples of suitable solvents include, but are not limited to, water, ethanol and acetic acid, glycerol, liquid polyethylene glycols and mixtures thereof. A particular solvent is water. The term "solvate" refers to a complex of variable stoichiometry formed by a solute (for example, a berberine alkaloid) and a solvent. In particular, the solvent used is an "acceptable solvent" as defined herein. When water is the solvent, the molecule is referred to as a hydrate.

As used herein "IRP001" refers to berberine, which as described herein is a quaternary ammonium cation and plant natural product with antimicrobial activity. The terms "IRP001" and "berberine" are used interchangeably herein. As used herein, "IRP001 chloride" or "IRP001 Cl" denotes the chloride salt of berberine; and "IRP001 sulfate" refers to the hemisulfate salt of berberine. Thus, it would be appreciated that the terms "IRP001 sulfate", "berberine sulfate", "IRP001 hemisulfate, and "berberine hemisulfate" are equivalent herein. The molecular structures of berberine quaternary ammonium cation, and the chloride and hemisulfate salts are shown in FIG. 4.

As used herein, the term "berberine alkaloid(s)" refers to berberine and compounds which share similar structures and characteristics to berberine and are suitable for the compositions/methods/uses of the invention. Such compounds include, but are not limited to the protoberberines: berberrubine, corexime, tetrahydropalmatine, jatrorrhizine, 13-hydroxy berberine chloride, coralyne chloride, 7,8-dihydro-13-methylberberine, fibrauretin (palmatine), and 13-benzylberberine.

Berberine alkaloids can exist in different isomers or different isomeric forms, for example, various tautomers or tautomeric forms. It will be understood that the term "berberine alkaloid(s)" encompasses different isomeric forms in isolation from each other as well as combinations.

Berberine alkaloids can also exist in various amorphous forms and crystalline forms (i.e. polymorphs). It will be also understood that the term "berberine alkaloid(s)" encompasses different amorphous and crystalline forms in isolation from each other as well as combinations.

As used herein, the term "berberine alkaloid(s)" encompasses acceptable salts, solvates, solvates of said salts or pro-drugs thereof.

As used herein, the term "food-producing animal" refers to an animal that is farmed for the production of food for consumption by another animal, for example, a human. It would be understood that the term "food-producing animal" includes, for example, a chicken or pig.

It will be understood that the term "isomer" refers to structural or constitutional isomers, tautomers, regioisomers, geometric isomers, or stereoisomers including enantiomers or diastereisomers. Further, a racemate will be understood to comprise an equimolar mixture of a pair of enantiomers.

It will be understood that the term "prodrug" refers to an inactive form of a compound which is transformed in vivo to the active form. Suitable prodrugs include esters, phosphonate esters etc, of the active form of the compound. Further discussion of pro-drugs may be found in Stella, V. J. et al., "Prodrugs", *Drug Delivery Systems,* 1985, pp. 112-176, *Drugs,* 1985, 29, pp. 455-473 and "Design of Prodrugs", ed. H. Bundgard, Elsevier, 1985.

As used herein a "safe" residue level of berberine is one that poses an insignificant risk of disease, particularly cancer.

As used herein the term "treatment", "treat", "treating" and the like refer to the control, healing or amelioration of a disease, disorder or condition, or a decrease in the rate of advancement of a disease, disorder or condition, or defending against or inhibiting a symptom or side effect, reducing the severity of the development of a symptom or side effect, and/or reducing the number or type of symptoms or side effects suffered by an animal subject, as compared to not administering a pharmaceutical composition comprising a compound of the invention. The term "treatment" encompasses use in a palliative setting.

The term "prevention", "prevent", "preventing" and the like as used herein are intended to encompass treatments that are used to delay or slow down the development of a disease, disorder or condition, or symptom or side effect thereof.

With regard to "prevention" and "treatment", the term "effective amount", as used herein, refers to an amount when administered to an animal, achieves a desired effect. For example, an effective amount of a composition disclosed herein is an amount that prevents or treats Necrotic Enteritis in a chicken. The exact total effective amount of antimicrobial depends on the purpose of the treatment and other factors including the animal subject (e.g. chicken versus pig), route of administration, body weight and severity of the disease.

BRIEF DESCRIPTION OF DRAWINGS

FIG. 5 is a graph of bird mortality prior to autopsy for each group.

FIG. 6 is a graph depicting the median small intestinal lesion scores by treatment/challenge group.

FIG. 7 depicts Necrotic Enteritis lesion scores.

FIG. 8 Photograph of duodenum of bird from Group 9; NE challenged, IVP/Berberine Water 1.0 g/L FIG. 9 Photograph of duodenum of bird from Group 6; NE challenged, No Berberine treatment FIG. 10 Photograph of duodenum of bird from Group 12; NE challenged IVP/Berberine Feed 2.0 g/kg FIG. 11 Photograph of duodenum of bird from Group 4; No Challenge IVP Berbering Water 1.0 g/L.

FIG. 12 Photograph of duodenum of bird from Group 6; NE challenged, No IVP/Berberine.

Figure 1:
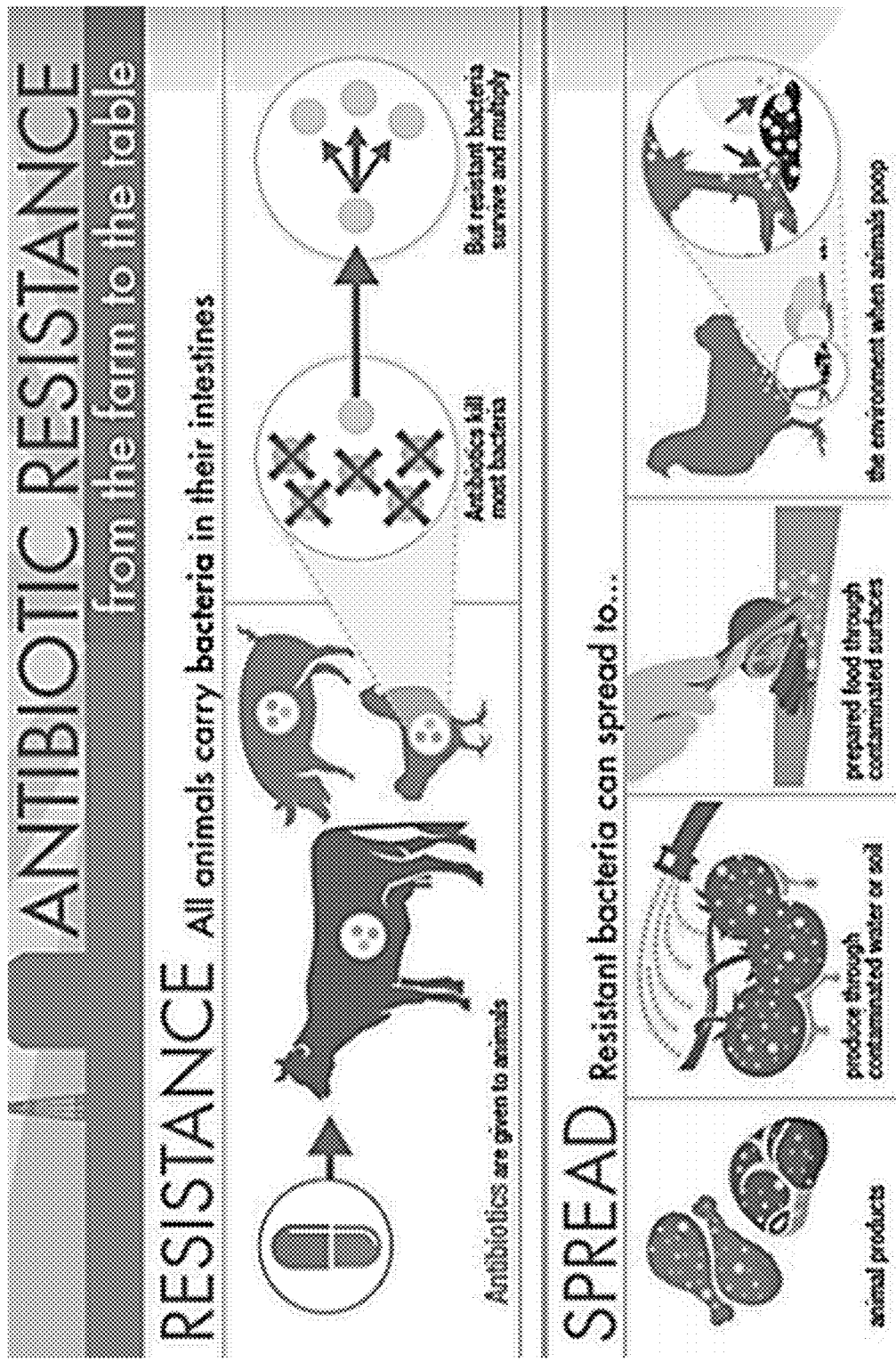
FIG. 1 depicts the spread of AMR from food-producing animal to human. Figure is taken from https://www.cdc.gov/foodsafety/challenges/from-farm-to-table.html.
Figure 2:
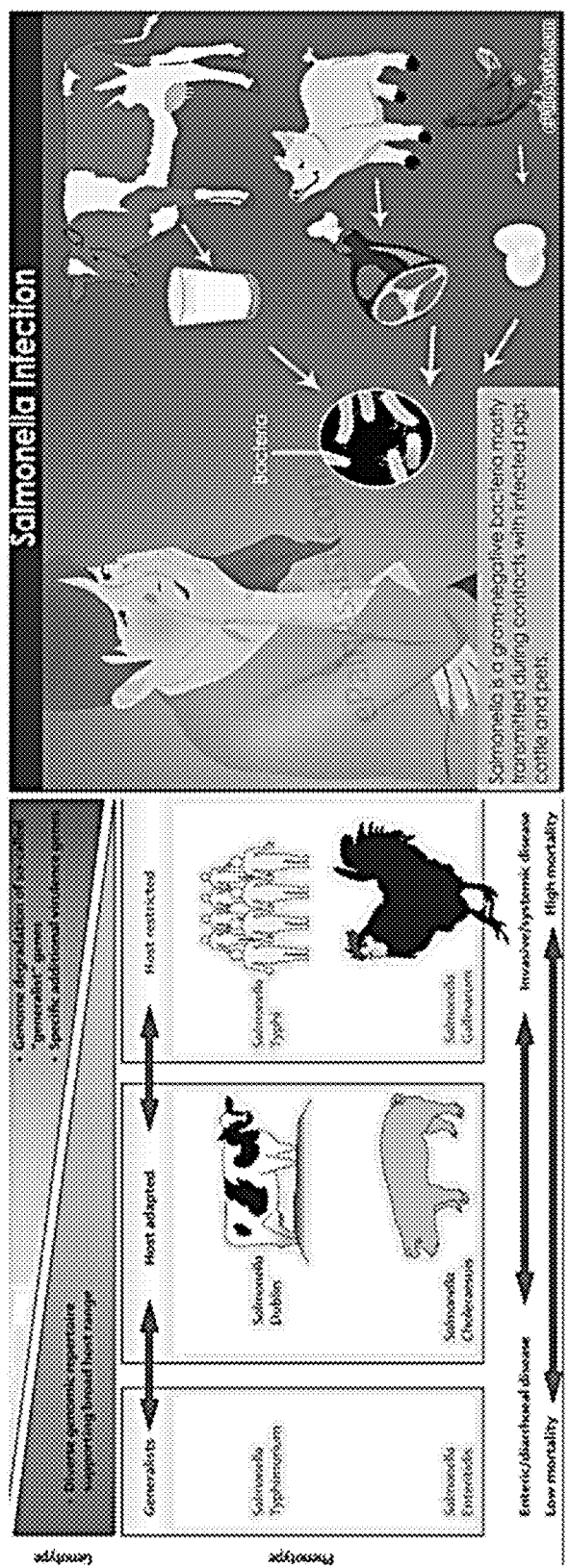
FIG. 2 depicts aspects of *Salmonella* infection and food poisoning. Figure is taken from http://thelancet.com/journals/lancet/article/PIIS0140-6736 (11)61752-2/fulltext and https://www.epainassist.com/abdominal-pain/stomach/food-poisoning.

Specific embodiments of the disclosure are described below. It will be appreciated that these embodiments are illustrative and not restrictive.

DETAILED DESCRIPTION OF INVENTION

The present disclosure relates to a method for the prevention and/or treatment of an infectious disease in an animal, wherein the method comprises administering a berberine alkaloid or an acceptable salt thereof to said animal.

In the methods (and animal feeds: dosing regimens and uses) disclosed herein: the animal is preferably human. The animal is preferably non-human. Preferably, the non-human animal is a food producing animal. The food producing animal is preferably selected from a chicken or a pig. Preferably, the animal is an aquatic animal. The aquatic animal is preferably finfish. Preferably, the aquatic animal is shellfish. Shellfish are preferably selected from crustaceans or molluscs. Preferably, crustaceans are selected from the group comprising crabs, crayfish, lobsters, prawns, and shrimp. Molluscs are preferably selected from the group comprising clams, mussels, oysters, scallops and winkles. Preferably, the animal is a mammal. The mammal preferably is a human, horse, dog, cat, sheep, cattle, pig or primate. Preferably, the animal is a bird. The bird is preferably chickens, geese, turkeys or ducks.

Spotty Liver Disease

Preferably, the infectious disease is a disease of the liver or an intestinal disease. Preferably, the infectious disease is an intestinal disease. The liver disease is preferably Spotty Liver Disease and the animal is a chicken. Preferably, the chicken is an egg-laying chicken. The Spotty Liver Disease is preferably caused by bacteria from the genus *Campylobacter*. Preferably, the *Campylobacter* is antibiotic resistant.

Salmonellosis

Preferably, the infectious disease is associated with food poisoning. The food poisoning is preferably *Salmonellosis*. Preferably, the *Salmonellosis* is caused by an antibiotic resistant strain of *Salmonella*.

Campylobacteriosis

Preferably, the infectious disease is Campylobacteriosis. The Campylobacteriosis is preferably caused by an antibiotic resistant strain of *Campylobacter*.

Infectious disease where causative agent is *E. coli*: Swine Diarrhoea Scour

Preferably, the infectious disease is caused by *E. coli*.

Of all the diseases in the sucking piglet, diarrhoea is the most common and probably the most important. In some outbreaks it is responsible for high morbidity and mortality. In a well-run herd there should be less than 3% of litters at any one time requiring treatment and piglet mortality from diarrhoea should be less than 0.5%. However, in severe outbreaks levels of mortality can rise to 7% or more and in individual untreated litters up to 100%. The main bacterial cause is *E. coli*. Scour in the piglet can occur at any age during sucking but there are often two peak periods, before 5 days and between 7 and 14 days.

The infectious disease is preferably diarrhoea and the animal is a pig. Preferably, the infectious disease is scour and the animal is a pig. The infectious disease is preferably dysentery and the animal is a pig.

Preferably, the infectious disease is caused by an antibiotic-resistant strain of *E. coli*.

Swine Dysentery Associated with *Brachyspira*

Swine Dysentery (SD) is caused by a spirochaetal bacterium called *Brachyspira* including *Brachyspira hyodysenteriae*, *Brachyspira piloscoli* and *Brachyspira hampsonii*. This organism causes a severe inflammation of the large intestine with a bloody mucous diarrhoea. The high cost of the disease is associated with morbidity, mortality, depression of growth and feed conversion efficiency, and costs of continual in-feed medication.

Preferably, the infectious disease is caused by bacteria from the genus *Brachyspira*. The infectious disease is preferably dysentery and the animal is a pig. Preferably, the infectious disease is caused by an antibiotic-resistant strain of *Brachyspira*.

The infectious disease is preferably caused by bacteria from the genus *Lawsonia*. Preferably, the infectious disease is caused by an antibiotic-resistant bacterial strain from the genus *Lawsonia*. The infectious disease is preferably caused by *Lawsonia intracellularis*.

Swine Ileitis Associated *Lawsonia intracellularis*

Ileitis comprises a group of conditions involving pathological changes in the small intestine associated with the bacterium *Lawsonia intracellularis*. The disease takes four different forms. The first form, porcine intestinal adenopathy (PIA), is an abnormal proliferation of the cells that line the intestines. PIA can develop into the three other forms, which are rarer: necrotic enteritis (NE), where the proliferated cells of the small intestine die and slough off with a gross thickening of the small intestine (hosepipe gut); regional ileitis (RI), inflammation of the terminal part of the small intestine and proliferative haemorrhagic enteropathy (PHE) or "bloody gut" where there is massive bleeding into the small intestine. PHE is the most common form of ileitis in growing pigs. PHE is more common in 60-kg pigs and gilts.

Preferably, the infectious disease is represented by a group of conditions selected from: porcine intestinal adenopathy, necrotic enteritis, regional ileitis and proliferative haemorrhagic enteropathy and the animal is a pig.

Infectious Disease where *Eimeria* is Causative Agent

Preferably, the infectious disease is caused by a parasite from the genus *Eimeria*. The parasite is preferably selected from *E. maxima, E. acervuline*, and *E. brunette*. Preferably, the infectious disease is caused by an antibiotic-resistant parasite from the genus *Eimeria*. The antibiotic-resistant parasite is preferably selected from an *E. maxima, E. acervuline*, and *E. brunette* antibiotic-resistant bacterial strain. Preferably, the infectious disease is Coccidiosis and the animal is a chicken.

Infectious Disease where *Clostridium* is Causative Agent

Preferably, the infectious disease is caused by bacteria from the genus *Clostridium*. The bacteria are preferably selected from the group consisting of: *Clostridium difficile* and *Clostridium perfringens*.

Preferably, the bacteria are *C. difficile*. The infectious disease is preferably diarrhoea and the animal is human. Preferably, the infectious disease is colitis and the animal is human.

*C. perfringens* and Necrotic Enteritis in Chickens

Preferably, the infectious disease is caused by bacteria from the genus *Clostridium*, wherein the bacteria are *C. perfringens*. The infectious disease is caused by antibiotic-resistant bacteria from the genus *Clostridium*, wherein the antibiotic-resistant bacteria are antibiotic-resistant *C. perfringens*.

The infectious disease is preferably Necrotic enteritis and the animal is a chicken. Preferably, the Necrotic enteritis is caused by a *C. perfringens* type A strain. The *C. perfringens* type A strain is preferably *C. perfringens* type A strain EHE-NE36. Preferably, the *C. perfringens* type A strain is *C. perfringens* type A strain EHE-NE18. The Necrotic enteritis is preferably caused by a *C. perfringens* type C strain.

Preferably, the administration occurs via the feed or water of the chicken. The feed is preferably in the form of a crumble or a pellet.

Preferably, the berberine alkaloid is administered in the feed of the chicken at a dose of 0.001 g/kg to 2.0 g/kg of feed. The berberine alkaloid is preferably administered in the feed at a dose of 0.003 g/kg to 0.3 g/kg of feed. The berberine alkaloid is preferably administered in the water of the chicken at a dose of 0.001 g/L to 1 g/L of water.

Preferably, the lesion score is decreased and/or the fecal oocyst count is reduced. Preferably, the lesion score is decreased. Preferably, the fecal oocyst count is reduced. There is preferably a reduction in morbidity. Preferably, there is a reduction in mortality. There is preferably a reduction in FCR. Preferably, there is an increase in average daily weight gain.

Feed Safety and Residue Levels

Human and animal drugs and animal feed additives are highly regulated for safety reasons. In Australia, the Therapeutic Goods Administration (TGA) is responsible for regulating therapeutic goods for human use while the Australian Pesticides and Veterinary Medicines Authority (APMVA) is responsible for the assessment and registration of pesticides and veterinary medicines. In the US, the Food and Drug Administration (FDA) is responsible for the approval of human and animal drugs and feed additives which are governed by the Federal Food, Drug, and Cosmetic Act (FD&C Act).

The FD&C Act requires that compounds intended for use in food-producing animals are shown to be safe and that food produced from animals exposed to these compounds is shown to be safe for consumption by people. In particular, the use in food-producing animals of any compound found to induce cancer when ingested by people or animal is prohibited by statute (21 CFR Part 500, Subpart E—Regulation of carcinogenic compounds used in food-producing animals) unless certain conditions are met (the so-called "Diethylstilbestrol (DES) Proviso"). Under the DES proviso use of a suspected carcinogenic compound is not prohibited if it can be determined by prescribed methods of examination that "no residue" of that compound will be found in the food produced from food-producing animals under conditions of use reasonably certain to be followed in practice.

Despite the safety of berberine alkaloids as evidenced by, for example, their wide use as dietary supplements for humans, berberine has come under suspicion that it is a carcinogenic agent, even though, berberine, itself, has anti-cancer activity (Ma, W.: Zhu, M.: Zhang, D.: Yang, L.: Yang, T.: Li, X.; and Zhang, Y. "Berberine inhibits the proliferation and migration of breast cancer ZR-75-30 cells by targeting Ephrin-B2" *Phytomedicine* 2017, 25:45-51). Thus, if the FDA decides that berberine should be regulated as a carcinogenic compound, US statue prohibits the use of berberine in food-producing animals unless the "no residue" DES proviso applies.

The term "no residue" refers to any residue remaining in the edible tissues that is so low that it presents an insignificant risk of cancer to consumers. More specifically, an insignificant risk of cancer is defined as a 1 in 1 million increase in risk.

A "safe" residue level of berberine, as used herein, is one that poses an insignificant risk of disease, particularly cancer.

Preferably, there is a low residue level of the berberine alkaloid in the animal after the treatment period. There is preferably a safe residue level of the berberine alkaloid in the animal after the treatment period.

Preferably, there is a safe residue level of the berberine alkaloid in the muscle tissue of the chicken after the treatment period. The residue level is at least below about 13 ng of the berberine alkaloid per g of muscle tissue Preferably, the residue level is about 10 ng of the berberine alkaloid per g of muscle tissue. The residue level is preferably about 5 ng/g.

Preferably, the berberine alkaloid has been administered in the feed of the chicken at a rate of about 0.3 g/kg. The residue levels of the berberine alkaloid in the muscle tissue of the chicken are preferably as follows:
  about 6.1 ng/g in the muscle tissue in the breast of the chicken;
  about 5.5 ng/g in the muscle tissue in the lower leg of the chicken; and
  about 11.6 ng/g in the muscle tissue in the upper leg of the chicken.

Preferably, the berberine alkaloid has been administered in the feed of the chicken at a dose of less than about less than 0.1 g/kg.

Preferably, the berberine alkaloid has been administered in the feed of the chicken at a dose of about 0.03 g/kg. 35. The residue levels of the berberine alkaloid in the muscle tissue of the chicken are preferably as follows:
  below 2 ng/g in the muscle tissue in the breast of the chicken;
  below 2 ng/g in the muscle tissue in the lower leg of the chicken; and
  below 2 ng/g in the muscle tissue in the upper leg of the chicken.

Preferably, there is a low residue level of the berberine alkaloid in the muscle tissue of the animal after the treatment period and a washout period. There is preferably a safe residue level of the berberine alkaloid in the muscle tissue of the animal after the treatment period and a washout period.

Preferably, there is a safe residue level of the berberine alkaloid in the muscle tissue of the chicken after the treatment period and a washout period.

Preferably, the washout period is a period between 1 and 2 weeks. The washout period is preferably selected from a period between 1 day and 14 days; between 1 day and 7 days; between 1 day and 4 days; and between 1 day and 2 days. Preferably, the washout period is a period selected from 1 day, 2 days, 4 days, 7 days and 14 days.

Preferably, after a washout period of 1 day the residue levels of the berberine alkaloid in the muscle tissue of the chicken are as follows:
  about 5.7 ng/g in the muscle tissue in the breast of the chicken;
  about 3.2 ng/g in the muscle tissue in the lower leg of the chicken; and
  about 6.0 ng/g in the muscle tissue in the upper leg of the chicken.

Preferably, after a washout period of 2 days the residue levels of the berberine alkaloid in the muscle tissue of the chicken are as follows:
  about 3.6 ng/g in the muscle tissue in the breast of the chicken;
  about 3.1 ng/g in the muscle tissue in the lower leg of the chicken; and
  about 4.5 ng/g in the muscle tissue in the upper leg of the chicken.

Preferably, after a washout period of 4, 7 and 14 days, the residue levels of the berberine alkaloid in the muscle tissue of the chicken are below 2 ng/g.

Preferably, the berberine alkaloid has been administered in the feed of the chicken at a dose of about 0.3 g/kg.

The level of residue is preferably at least below 13 ng of the berberine alkaloid per g of muscle tissue. The level of residue is preferably about 10 ng of the berberine alkaloid per g of muscle tissue. Preferably, the level of residue is about 5 ng/g.

Preferably, the berberine alkaloid has been administered in the feed of the chicken at a dose of about greater than 0.1 g/kg.

Preferably, there is a low residue level of the berberine alkaloid in the liver and muscle tissue of the animal after the treatment period. Preferably, there is a safe residue level of the berberine alkaloid in the liver and muscle tissue of the animal after the treatment period.

Preferably, there is a safe residue level of the berberine alkaloid in the liver and muscle tissue of the chicken after the treatment period. The residue levels of the berberine alkaloid in the liver and muscle tissue of the chicken are preferably below 2 ng/g. Preferably, the berberine alkaloid has been administered in the feed of the chicken at a dose of about 0.03 g/kg.

Preferably, there is a low residue level of the berberine alkaloid in the liver and muscle tissue of the animal after the treatment period and a washout period. Preferably, there is a safe residue level of the berberine alkaloid in the liver and muscle tissue of the animal after the treatment period and a washout period.

Preferably, there is a safe residue level of the berberine alkaloid in the liver and muscle tissue of the chicken after the treatment period and a washout period. The washout period is preferably a period between 1 week and 2 weeks.

Preferably, the washout period is a period selected from between 1 day and 14 days; between 1 day and 7 days; 1 day and 4 days; and between 1 day and 2 days. The washout period is preferably a period selected from 1 day, 2 days, 4 days, 7 days and 14 days.

Preferably, after a washout period of 1 day the residue levels of the berberine alkaloid in the muscle tissue of the chicken are as follows:
 about 5.7 ng/g in the muscle tissue in the breast of the chicken;
 about 3.2 ng/g in the muscle tissue in the lower leg of the chicken; and
 about 6.0 ng/g in the muscle tissue in the upper leg of the chicken,
 and a residue level of the berberine alkaloid in the liver tissue of the chicken of about 8.0 ng/g.

Preferably, after a washout period of 7 days the residue levels of the berberine alkaloid in the muscle tissue in the breast, lower leg and upper leg of the chicken are below 2 ng/g and the residue level of the berberine alkaloid in the liver tissue of the chicken is about 6.5 ng/g.

Preferably, after a washout period of 14 days the residue levels of the berberine alkaloid in the muscle tissue in the breast, lower leg and upper leg of the chicken are below 2 ng/g and the residue level of the berberine alkaloid in the liver tissue of the chicken is about 3.0 ng/g.

Preferably, the berberine alkaloid has been administered in the feed of the chicken at a dose of about 0.3 g/kg.

Preferably, there is a low residue level of the berberine alkaloid in the liver and muscle tissue of the animal after the treatment period. Preferably, there is a safe residue level of the berberine alkaloid in the liver and muscle tissue of the animal after the treatment period.

Preferably, there is a safe residue level of the berberine alkaloid in the liver and muscle tissue of the chicken after the treatment period. The residue levels of the berberine alkaloid in the liver tissue and muscle tissue in the breast, lower leg and upper leg of the chicken are preferably below 2 ng/g. Preferably, the berberine alkaloid has been administered in the feed of the chicken at a dose of about 0.03 g/kg.

Preferably, there is a safe residue level of the berberine alkaloid in the liver tissue of the chicken after the treatment period and a washout period. The washout period is preferably a period selected from between 1 week and 2 weeks. Preferably, the washout period is a period selected from between 1 day and 14 days; between 1 day and 7 days; between 1 day and 4 days; and between 1 day and 2 days. The washout period is preferably a period selected from 1 day, 2 days, 4 days, 7 days and 14 days.

Preferably, after a washout period of 1 day the residue level of the berberine alkaloid in the liver tissue of the chicken is about 8.0 ng/g. After a washout period of 7 days the residue level of the berberine alkaloid in the liver tissue of the chicken is preferably about 6.5 ng/g. Preferably, after a washout period of 14 days the residue level of the berberine alkaloid in the liver tissue of the chicken is about 3.0 ng/g. The berberine alkaloid has preferably been administered in the feed of the chicken at a dose of about 0.3 g/kg.

Preferably, the treatment period is 35 days.

A "Residue study" is described elsewhere. The residue level of a berberine alkaloid may be determined by experiment. An example protocol for determining the residue level of a berberine alkaloid in animal tissue using LC-MS/MS is as follows:
 Samples of muscle from breast, leg and thigh, and liver and kidney were excised from each bird after euthanasia. A known weight of tissue (approximately 1 g) was homogenized in 2 mL water. Samples were centrifuged and a known volume of the supernatant was removed for analysis of berberine by LC-MS/MS to provide the residue level of berberine in muscle tissue (ng of berberine per g of muscle tissue).

Administration of Berberine Formulations

Preferably, the berberine alkaloid is berberine hemisulfate. The berberine alkaloid is preferably berberine chloride.

Preferably, the method further comprises an additive that masks the bitter flavour of the berberine alkaloid or acceptable salt.

Berberine

Berberine is an isoquinoline alkaloid extracted from *Rhizoma coptidis*, *Phellodendri chinensis* cortex, and other herbs. According to the Chinese Pharmacopoeia, the berberine content of *Rhizoma coptidis*, *Phellodendri chinensis* and *Phellodendron amurense* and *Berberidis radix* are 5.5%, 3.0%, 0.6% and 0.6% respectively. *Rhizoma coptidis* (Huanglian in Chinese) belongs to family Ranunculaceae and contains three main Coptis species: *Coptis chinensis* (Weilian in Chinese), *Coptis deltoidea* (Yalian in Chinese), and *Coptis teeta* (Yunlian in Chinese). *Rhizoma coptidis* is harvested in autumn and sliced after the removing the fibrous roots. Those with bright yellow sections and very bitter taste are considered of good quality. The bitter taste of berberine (and other berberine alkaloids as disclosed herein) makes taste-masking/palatability an important issue to consider when formulating berberine alkaloids for administration to animal subjects.

Figure 4:
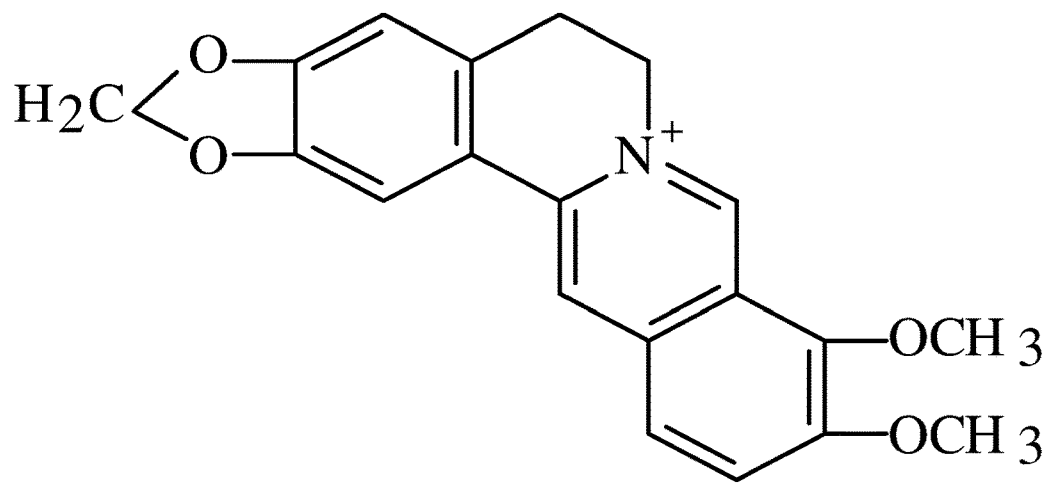
FIG. 4 depicts the molecular structure of berberine quaternary ammonium cation; berberine chloride and berberine hemisulfate.
Figure 4:
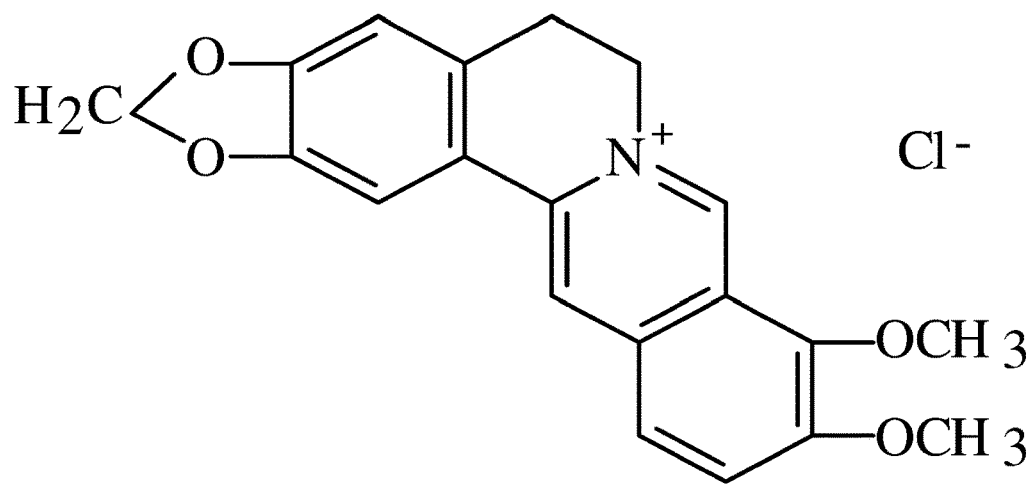
Figure 4:
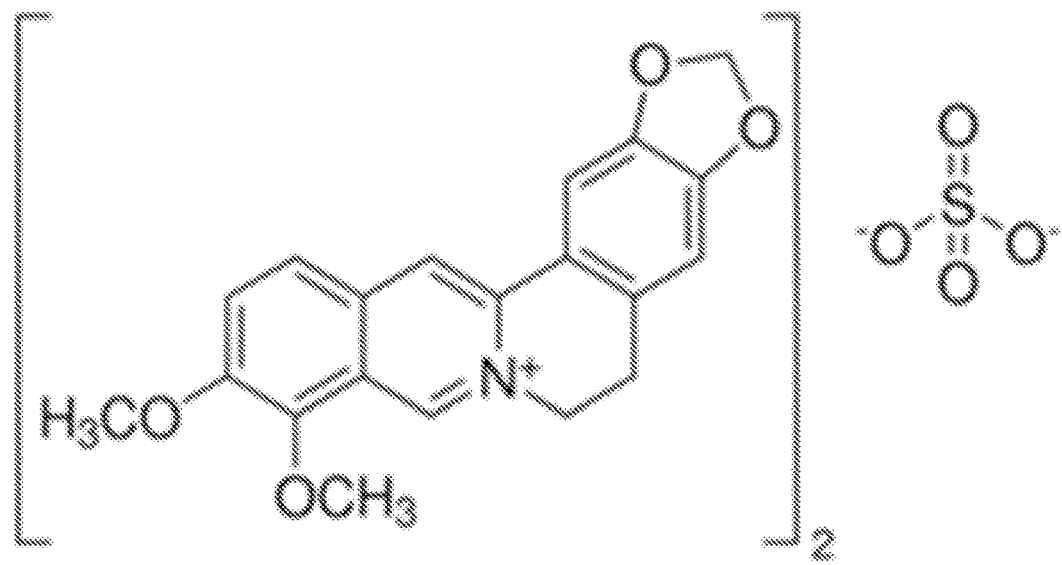

Berberine is a yellow powder. The chloride salt is slightly soluble in cold water, but freely soluble in boiling water. It is practically insoluble in cold ethanol. The hemisulfate salt is soluble in about 30 parts water, slightly soluble in ethanol. Berberine is a quaternary ammonium cation with molecular formula of $C_{20}H_{18}NO_4^+$ and molecular weight of 336.36. FIG. 4 depicts the molecular structure of the berberine ammonium cation, berberine chloride salt, and berberine hemisulfate salt.

Berberine may be administered in any form acceptable for enteral administration. Suitable non-limiting forms for enteral administration include tablets, capsules, paste, granules, chewable wafers, gel, oral liquid, injectable liquid, medicated water and medicated feed, and suppositories. However with food producing animals where economic interests are important, the preferred method of administering berberine is via a feed additive in the form of granules, or a medicated feed. It may also be administered via the drinking water of an animal subject by mixing water with a suitable solution or suspension of berberine.

The present disclosure also contemplates the provision of granules and liquid formulations that can be added to food and water which make the formulations disclosed herein more palatable to, for example, food-producing animal subjects. For example, a palatable berberine alkaloid formulation may comprise berberine and an acceptable excipient which is suitable for forming a granular product. The acceptable excipient which is suitable for forming a granular product is, for example, cornstarch or polyvinylpyrollidone (PVP). In one example, the liquid formulation is a liquid concentrate.

There are also many compounds which share similar structures and characteristics to berberine including the protoberberines: berberrubine, coreximine, tetrahydropalmatine, jatrorrhizine, 13-hydroxy berberine chloride, coralyne chloride, 7,8-dihydro-13-methylberberine, fibrauretin (palmatine), and 13-benzylberberine. The protoberberines, together with berberine, are suitable for the compositions/ methods/uses of the invention and are referred to in the specification as "berberine alkaloids".

Fibrauretin (Palmatine)

Fibrauretin or palmatine is a bitter tasting alkaloid extracted from *Fibauera recisa* Pierre. According to the Chinese Pharmacopoeia, *Fibrauera recisa* Pierre consists of no less than 2.0% fibrauretin. Another source is *Coptidis rhizoma*, the rhizome of *Coptis chinensis* Franch, *Coptis deltoidea* and *Coptis teeta* Wall. *Coptidiz rhizoma* consists of no less than 1.5% fibrauretin.

Figure 13:
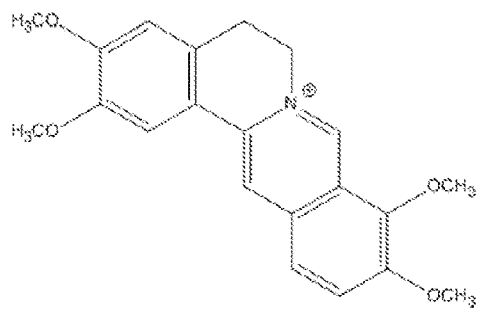
FIG. 13 depicts the molecular structures and names of representative compounds referred to in the disclosure.
Figure 13:
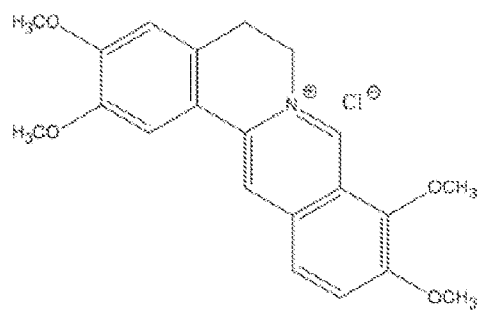
Figure 13:
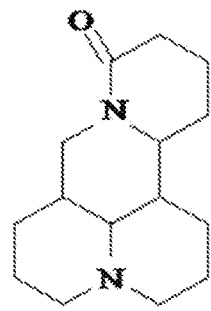
Figure 13:
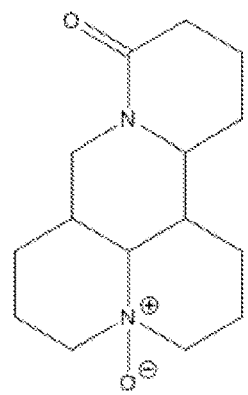
Figure 13:
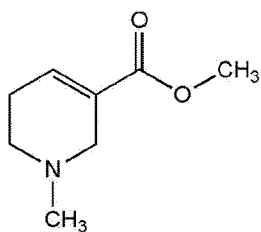
Figure 13:
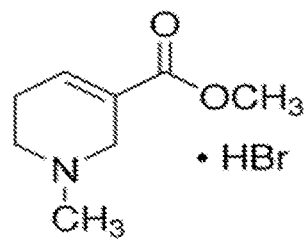
Figure 13:
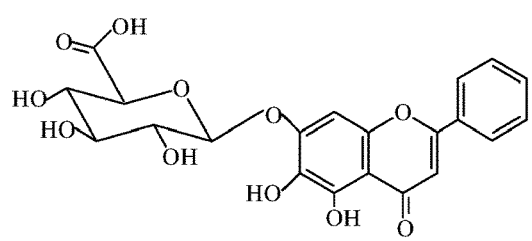
Figure 13:
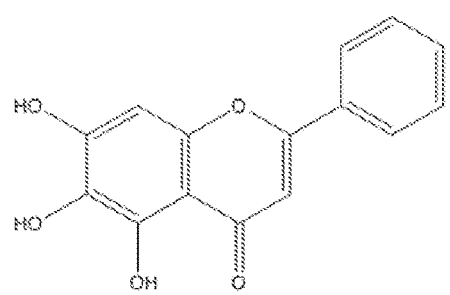

Palmatine chloride is a yellow solid, which is soluble in hot water, sparingly soluble in water, and slightly soluble in ethanol. Its melting point is 196-198° C. Its molecular formula is $C_{21}H_{22}NO_4Cl$ with a molecular weight of 387.86. The molecular structure of the palmatine quaternary ammonium cation and the structure of the chloride salt are set out in FIG. 13.

The total effective amount or dose of the antimicrobial compound in the prepared feed may range from 0.001 g/kg to 2 g/kg. Example amounts of the total amount of antimicrobial compound in the prepared feed are: 0.001 g/kg (0.0001%), 0.003 g/kg (0.0003%), 0.01 g/kg (0.001%), 0.03 g/kg (0.003%), 0.1 g/kg (0.01%), 0.3 g/kg (0.03%), 1.0 g/kg (0.1%) and 2 g/kg (0.2%).

The present disclosure also relates to an animal feed comprising a berberine alkaloid and an animal foodstuff, wherein the berberine alkaloid is in an amount of about 0.001% to 1% w/w of the animal foodstuff.

The amount of the berberine alkaloid in the foodstuff may range from 0.001 g/kg to 2 g/kg i.e., 0.001% to 0.2% w/w. Example amounts of the berberine alkaloid in the foodstuff are: 0.001 g/kg (0.0001%), 0.003 g/kg (0.0003%), 0.01 g/kg (0.001%), 0.03 g/kg (0.003%), 0.1 g/kg (0.01%), 0.3 g/kg (0.03%), 1.0 g/kg (0.1%) and 2.0 g/kg (0.2%).

The feed is preferably in the form of a crumble; pellet; or in an aqueous form.

The present disclosure also relates to a dosing regimen comprising administering a berberine alkaloid, or an animal feed as disclosed herein to an animal, wherein the berberine alkaloid, or the composition or animal feed is administered for 1 to 6 weeks and in an amount effective to prevent and/or treat an infectious disease in an animal.

Preferably, the berberine alkaloid or animal feed is administered for 1, 2, 3, 4, 5 or 6 weeks. Preferably, the berberine alkaloid, or animal feed is administered for 1 to 6; 2 to 5; or between 3 to 4 weeks.

Preferably, the berberine alkaloid is administered at a concentration of about 0.6 g/L in-water or about 1.2 g/kg in-feed. The amount of the berberine alkaloid in the feed may range from 0.001 g/kg to 2 g/kg i.e., 0.0001% to 0.2% w/w. Example amounts of the berberine alkaloid or acceptable salt in the foodstuff are: 0.001 g/kg (0.0001%), 0.003 g/kg (0.0003%), 0.01 g/kg (0.0001%), 0.03 g/kg (0.0003%), 0.1 g/kg (0.01%), 0.3 g/kg (0.03%), 1.0 g/kg (0.1%), and 2 g/kg (0.2%).

The disclosure also relates to a method for the reduction of feed conversion ratio in a food-producing animal, wherein the method comprises the step of administering a berberine alkaloid to the food-producing animal.

Preferably, the food-producing animal is free of disease. The food-producing animal is preferably diseased. Preferably, the food-producing animal is selected from a chicken or a pig. The food-producing animal is preferably a chicken.

The disclosure also relates to a method for preventing or treating an infectious disease in an animal comprising administering an animal feed disclosed herein.

The disclosure also relates to a method for preventing or treating an infectious intestinal disease in an animal comprising administering an animal feed disclosed herein.

The disclosure also relates to a method for preventing or treating an infectious disease caused by *Eimeria* in an animal comprising administering an animal feed disclosed herein.

Preferably, the infectious disease is caused by an antibiotic-resistant parasite from the genus *Eimeria*. The infectious disease is preferably Coccidiosis and the animal is a chicken.

Preferably, the infectious disease is Necrotic enteritis and the animal is a chicken.

The present disclosure also relates to use of a berberine alkaloid in the preparation of a medicament for the prevention and/or treatment of:
- an infectious disease in an animal;
- an infectious intestinal disease in an animal;
- an infectious disease caused by *Eimeria* in an animal; or
- an infectious disease caused by bacteria from the genus *Clostridium*, wherein the bacteria are *C. perfringens*.

The present disclosure also relates to use of a berberine alkaloid in the prevention and/or treatment of:
- an infectious disease in an animal;
- an infectious intestinal disease in an animal;
- an infectious disease caused by *Eimeria* in an animal; or
- an infectious disease caused by bacteria from the genus *Clostridium*, wherein the bacteria are *C. perfringens*.

The present disclosure also relates to a berberine alkaloid for use in the prevention and/or treatment of:
- an infectious disease in an animal;
- an infectious intestinal disease in an animal;
- an infectious disease caused by *Eimeria* in an animal; or
- an infectious disease caused by bacteria from the genus *Clostridium*, wherein the bacteria are *C. perfringens*.

Development of formulations, dosages and regimens for preventing or treating infectious disease in an animal is described in the below studies.

Formulation and Palatability Study

A study to determine feed palatability and bird productivity following administration of four IRP001 formulations to broiler chickens.

Study Design—On receipt, two hundred and forty (240) day-old commercial broiler chickens were divided evenly in individual floor pens and allowed to acclimatise for 7 days. On Day 7, birds were weighed and sequentially allocated as they present to sixteen (16) groups, each of 15 birds. Feed intake, water intake, weight gain and mortality are used as outcome parameters.

Investigational Veterinary Products (IVPs)

TABLE 1

IVPs for formulation and palatability study

| Name | Composition | Dose Level (g/kg)* |
|---|---|---|
| IRP001 Chloride Masked | 30% IRP001 | 2.7, 5.3 and 10.7 |
| IRP001 Sulfate Masked | 10% IRP001 | 8.0, 16.0 and 32.0 |
| IRP001 Chloride Unmasked | 100% IRP001 | 0.4, 0.8, and 1.6 |
| IRP001 Sulfate Unmasked | 100% IRP001 | 0.4, 0.8 and 1.6 |

*Doses are based on fixed concentrations of IRP001 in-feed

Study animals are dosed according to the treatment regime detailed in Table 2 below. Medicated feed is provided to chickens in the relevant treatments ad lib as their sole source of feed with potable water also provided ad lib.

TABLE 2

Treatment Regime

| Group | Formulation | IVP conc. (g/kg) | Route | Trt. Days | No. Animals |
|---|---|---|---|---|---|
| 1 | Nil | — | — | — | 15 |
| 2 | Nil | — | — | — | 15 |
| 3 | Nil | — | — | — | 15 |
| 4 | Nil | — | — | — | 15 |
| 5 | IVP Cl (masked) | 2.7 | In-feed | 7-21 | 15 |
| 6 | IVP Cl (masked) | 5.3 | In-feed | 7-21 | 15 |
| 7 | IVP Cl (masked) | 10.7 | In-feed | 7-21 | 15 |
| 8 | IVP S (masked) | 8.0 | In-feed | 7-21 | 15 |
| 9 | IVP S (masked) | 16.0 | In-feed | 7-21 | 15 |
| 10 | IVP S (masked) | 32.0 | In-feed | 7-21 | 15 |
| 11 | IVP Cl (unmasked) | 0.4 | In-feed | 7-21 | 15 |
| 12 | IVP Cl (unmasked) | 0.8 | In-feed | 7-21 | 15 |
| 13 | IVP Cl (unmasked) | 1.6 | In-feed | 7-21 | 15 |
| 14 | IVP S (unmasked) | 0.4 | In-feed | 7-21 | 15 |
| 15 | IVP S (unmasked) | 0.8 | In-feed | 7-21 | 15 |
| 16 | IVP S (unmasked) | 1.6 | In-feed | 7-21 | 15 |

TABLE 3

Schedule of Events

| Approx. Study Day | Event |
|---|---|
| Pre-study | Receipt of formulation. Receipt of Animal Ethics approval |
| 0 | Broiler chicks hatched. Chicks transported and placed into floor pens. Commence twice daily health monitoring. |
| 1-6 | Acclimatisation - monitor well-being twice daily, water and feed intake. |
| 7 | Trial conduct - monitor well-being twice daily, ad-lib water and feed intake by treatment group. |
| 14 | Weigh all birds. Determine water and feed intake. |
| 21 | Weigh all birds. Determine water and feed intake. Euthanize all birds for visual gross pathological scoring and collection of residue samples from selected birds. |
| 22 | Reporting |

From the above, food and water intake and body weight of animals (and organs after euthanisation) can be recorded. The average weight gain, average daily weight gain over the treatment period can be calculated as well as feed conversion ratio (FCR). Performance of animals can be evaluated by these parameters. Also, food and water intake parameters can provide an indication of medication palatability whereas weight gain and feed conversion ratio (FCR) parameters can provide the antibiotic effect of the IVP i.e. the extent the IVP is promoting growth.

Feed Conversion Efficiency Study

A study to determine the feed conversion efficiency and tissue residues of IRP001 when administered via feed to commercial broiler chickens. Residues with a wash-out period of 1 week are also explored.

Investigational Veterinary Products (IVP)

TABLE 4

IVP for feed conversion efficiency study

| Name | Composition | Dose Level (g/kg) |
|---|---|---|
| IRP001 chloride | 100% IRP001 chloride | 1.0, 0.1, 0.03 and 0.01 |

TABLE 5

Treatment regime

| Group | Bird type | Treatment | IVP conc. In feed (g/kg) | Sacrifice Day | Trt. In-feed days | No. Animals |
|---|---|---|---|---|---|---|
| 1 | Broiler | — | — | 42 | — | 12 or 13 |
| 2 | Broiler | — | — | 42 | — | 12 or 13 |
| 3 | Broiler | IVP | 1.0 | 42 | 2-28 | 12 or 13 |
| 4 | Broiler | IVP | 1.0 | 42 | 2-35 | 12 or 13 |
| 5 | Broiler | IVP | 1.0 | 42 | 2-42 | 12 or 13 |
| 6 | Broiler | IVP | 0.1 | 42 | 2-28 | 12 or 13 |
| 7 | Broiler | IVP | 0.1 | 42 | 2-35 | 12 or 13 |
| 8 | Broiler | IVP | 0.1 | 42 | 2-42 | 12 or 13 |
| 9 | Broiler | IVP | 0.03 | 42 | 2-28 | 12 or 13 |
| 10 | Broiler | IVP | 0.03 | 42 | 2-35 | 12 or 13 |
| 11 | Broiler | IVP | 0.03 | 42 | 2-42 | 12 or 13 |
| 12 | Broiler | IVP | 0.01 | 42 | 2-28 | 12 or 13 |
| 13 | Broiler | IVP | 0.01 | 42 | 2-35 | 12 or 13 |
| 14 | Broiler | IVP | 0.01 | 42 | 2-42 | 12 or 13 |

TABLE 6

Schedule of events

| Approx. Study Day | Event |
|---|---|
| Pre-study | Receipt of formulation. Receipt of Animal Ethics approval |
| 0 | Broiler chicks hatched. Broiler chicks transported and placed into temperature controlled floor pens. Birds weighed (by treatment group). Commence twice daily health observations. |
| 0-42 | Weigh daily feed added and calculate daily feed intake by treatment group. Measure daily water volume and calculate daily water intake by treatment group. |
| 7, 14, 21, 28, 35 & 42 | Weigh all birds - Groups 1 through Group 14 inclusive. Record individual birds bodyweight. |
| 42 | Weigh all birds - Groups 1 through 14 inclusive. Euthanise, conduct individual clinical examination and gross visual pathological assessment on each bird. Collect tissues and intestinal biota samples from all Group 1 through Group 14 birds. Liver, kidney, breast muscle (1) and leg (2) [upper and lower thigh] collected and stored frozen (<10 degrees Celsius). |
| 2-28 | Provide medicated feed to Groups 3, 6, 9 and 12 birds. |
| 2-35 | Provide medicated feed to Groups 4, 7, 10 and 13 birds. |
| 2-42 | Provide medicated feed to Groups 5, 8, 11 and 14 birds. |

The residue level of IRP0001 after observing a wash-out period of 1 week is determined by experiment as follows:

Samples of muscle from breast, leg and thigh, and liver and kidney are excised from each bird after euthanasia. A known weight of tissue (approximately 1 g) is homogenized in 2 mL water. Samples are centrifuged and a known volume of the supernatant is removed for analysis of IRP001 by LC-MS/MS to provide the residue level of berberine in muscle tissue (ng of berberine per g of muscle tissue).

Efficacy Study of IRP001 Against Industry Standard Zinc Bacitracin

Determination of the efficacy in prevention or treatment of Necrotic Enteritis by administration of IRP001 including investigation of dose response, feed conversion rate, tissue residues and safety. IRP001 is administered via feed to broiler chickens artificially challenged with pathogenic strains of *Eimeria* spp. and *Clostridium Perfringens* utilizing a proven experimental model. Current industry standard treatment, Zinc Bacitracin, is used for efficacy and FCR comparison.

Study Design (Necrotic Enteritis challenge)—Commercial broiler chickens housed in isolators, are infected orally at 9 days of age with 5,000 attenuated vaccine strain sporulated oocysts each of *E. maxima* and *E. acervuline* and 2,500 sporulated oocysts of *E. brunetti* in 1 mL of 1% (w/v) sterile saline.

Six days following oocyst challenge (Days 15), a known pathogenic strain of *Clostridium Perfringens* is administered (type A strain NE18), i.t. (~8.0 log 10 cfu/chicken). Two birds per group from all 42 groups are sacrificed at Day 17 to define lesion score.

Feed intake, weight gain, mortality and NE lesion scores at autopsy are used as outcome parameters.

Investigational Veterinary Product (IVP)—IRP001

TABLE 7

IVP and dose level for efficacy study of IRP001 against industry standard Zinc Bacitracin

| Name | Composition | Dose Level (g/kg) |
|---|---|---|
| IRP001 | 100% IRP001 | 1.0, 0.3, 0.1, 0.03 |
| Zinc Bacitracin | Industry standard | Industry standard |

TABLE 8

Challenge and Treatment Regime

| Grp. | Bird type | Start day | In-feed (g/kg) | Eimeria challenge | CP challenge | Evaluation Days | No. Animals |
|---|---|---|---|---|---|---|---|
| 1 | Broiler | 1 | Nil | Nil | Nil | 17 & 35 | 10 |
| 2 | Broiler | 1 | Nil | Nil | Nil | 17 & 35 | 10 |
| 3 | Broiler | 1 | Nil | Nil | Nil | 17 & 35 | 10 |
| 4 | Broiler | 1 | Nil | Nil | Nil | 17 & 35 | 10 |
| 5 | Broiler | 1 | Nil | Nil | Nil | 17 & 35 | 10 |
| 6 | Broiler | 1 | Nil | Nil | Nil | 17 & 35 | 10 |
| 7 | Broiler | 1 | Nil | Day 9 | Day 15 | 17 & 35 | 10 |
| 8 | Broiler | 1 | Nil | Day 9 | Day 15 | 17 & 35 | 10 |
| 9 | Broiler | 1 | Nil | Day 9 | Day 15 | 17 & 35 | 10 |
| 10 | Broiler | 1 | Nil | Day 9 | Day 15 | 17 & 35 | 10 |
| 11 | Broiler | 1 | Nil | Day 9 | Day 15 | 17 & 35 | 10 |
| 12 | Broiler | 1 | Nil | Day 9 | Day 15 | 17 & 35 | 10 |
| 13 | Broiler | 1 | 1.0 | Day 9 | Day 15 | 17 & 35 | 10 |
| 14 | Broiler | 1 | 1.0 | Day 9 | Day 15 | 17 & 35 | 10 |
| 15 | Broiler | 1 | 1.0 | Day 9 | Day 15 | 17 & 35 | 10 |
| 16 | Broiler | 1 | 1.0 | Day 9 | Day 15 | 17 & 35 | 10 |
| 17 | Broiler | 1 | 1.0 | Day 9 | Day 15 | 17 & 35 | 10 |
| 18 | Broiler | 1 | 1.0 | Day 9 | Day 15 | 17 & 35 | 10 |
| 19 | Broiler | 1 | 0.3 | Day 9 | Day 15 | 17 & 35 | 10 |
| 20 | Broiler | 1 | 0.3 | Day 9 | Day 15 | 17 & 35 | 10 |
| 21 | Broiler | 1 | 0.3 | Day 9 | Day 15 | 17 & 35 | 10 |
| 22 | Broiler | 1 | 0.3 | Day 9 | Day 15 | 17 & 35 | 10 |
| 23 | Broiler | 1 | 0.3 | Day 9 | Day 15 | 17 & 35 | 10 |
| 24 | Broiler | 1 | 0.3 | Day 9 | Day 15 | 17 & 35 | 10 |
| 25 | Broiler | 1 | 0.1 | Day 9 | Day 15 | 17 & 35 | 10 |
| 26 | Broiler | 1 | 0.1 | Day 9 | Day 15 | 17 & 35 | 10 |
| 27 | Broiler | 1 | 0.1 | Day 9 | Day 15 | 17 & 35 | 10 |
| 28 | Broiler | 1 | 0.1 | Day 9 | Day 15 | 17 & 35 | 10 |
| 29 | Broiler | 1 | 0.1 | Day 9 | Day 15 | 17 & 35 | 10 |
| 30 | Broiler | 1 | 0.1 | Day 9 | Day 15 | 17 & 35 | 10 |
| 31 | Broiler | 1 | 0.03 | Day 9 | Day 15 | 17 & 35 | 10 |
| 32 | Broiler | 1 | 0.03 | Day 9 | Day 15 | 17 & 35 | 10 |
| 33 | Broiler | 1 | 0.03 | Day 9 | Day 15 | 17 & 35 | 10 |
| 34 | Broiler | 1 | 0.03 | Day 9 | Day 15 | 17 & 35 | 10 |
| 35 | Broiler | 1 | 0.03 | Day 9 | Day 15 | 17 & 35 | 10 |
| 36 | Broiler | 1 | 0.03 | Day 9 | Day 15 | 17 & 35 | 10 |
| 37 | Broiler | 1 | Zn Bac | Day 9 | Day 15 | 17 & 35 | 10 |
| 38 | Broiler | 1 | Zn Bac | Day 9 | Day 15 | 17 & 35 | 10 |
| 39 | Broiler | 1 | Zn Bac | Day 9 | Day 15 | 17 & 35 | 10 |
| 40 | Broiler | 1 | Zn Bac | Day 9 | Day 15 | 17 & 35 | 10 |
| 41 | Broiler | 1 | Zn Bac | Day 9 | Day 15 | 17 & 35 | 10 |
| 42 | Broiler | 1 | Zn Bac | Day 9 | Day 15 | 17 & 35 | 10 |

TABLE 9

Schedule of Events

| Approx. Study Day | Event |
|---|---|
| Pre-study | Receipt of formulation. Receipt of Animal Ethics approval |
| 0 | Broiler chicks hatched. Broiler chicks transported and placed into study pens. |
| 1 | Commence medicated feeding - all Groups. |
| 1-35 | Twice daily observation - all Groups. |
| 7, 14, 21, 28, and 35 | Weigh all birds and record individual weights for feed conversion calculation. Determine any residual feed remaining in feeders on each of the weigh days. |
| 9 | *Eimeria* spp. Challenge - Groups 7 to 42 inclusive. |
| 15 | *Clostridium perfringens* challenge - Groups 7 to 42 inclusive. |
| 17 | Sacrifice and autopsy 2 birds per group, score intestinal lesions - all Groups. |
| 35 | Sacrifice, weigh and autopsy remaining 8 birds per group, collect gut scrapings and selected tissue samples from 4 birds per group - all Groups. |

The residue level of IRP0001 can be determined by experiment as follows:

Samples of muscle from breast, leg and thigh, and liver and kidney are excised from each bird after euthanasia. A known weight of tissue (approximately 1 g) is homogenized in 2 mL water. Samples are centrifuged and a known volume of the supernatant is removed for analysis of IRP001 by LC-MS/MS to provide the residue level of berberine in muscle tissue (ng of berberine per g of muscle tissue).

Dose Rate Study

The study objective is to evaluate the efficacy of three dose rates of IRP001 in-feed against a mixed moderate coccidiosis challenge (*Eimeria* spp.) in commercial meat chickens and to assess any occurrence of Necrotic Enteritis or non-specific enteritis. Safety data along with tissue residue data is to be obtained.

Study Design (*Eimeria* challenge)—Commercial broiler chickens housed in pens, are infected 14 days of age (Day 14) with wild-type *Eimeria* oocysts: approximately 12,000 *E. tenella*, 40,000 *E. acervuline* and as many *E. maxima* oocysts as possible per bird.

Seven days following oocyst challenge (Days 21), four birds per group are randomly selected from each trial pen and humanely euthanized.

General gut health (enteritis) and lesion scores at Day 21 and at autopsy are to be assessed. Feed intake, weight gain and mortality are to be used as outcome parameters. Feed conversion ratio is calculated over each time period.

Investigational Veterinary Product (IVP)—IRP001

TABLE 10

IVP and control for dose rate study

| Name | Composition | Dose Level (g/kg) |
|---|---|---|
| IRP001 | 100% IRP001 | 1.0, 0.3, and 0.1 |
| Salinomycin | Industry standard | 60 ppm |
| Salinomycin + Zinc Bacitracin | Industry standard | 60 ppm + 50 ppm |

TABLE 11

Treatment and challenge regime

| Grp. | Bird type | In-feed (g/kg) | Eimeria challenge | Evaluation Day | No. Animals |
|---|---|---|---|---|---|
| 1 | Broiler | Nil | Nil | 21 | 36 |
| 2 | Broiler | Nil | Nil | 21 | 36 |
| 3 | Broiler | Nil | Nil | 21 | 36 |
| 4 | Broiler | Nil | Nil | 21 | 36 |
| 5 | Broiler | Nil | Nil | 21 | 36 |
| 6 | Broiler | Nil | Nil | 21 | 36 |
| 7 | Broiler | 1.0 | Day 14 | 21 | 36 |
| 8 | Broiler | 1.0 | Day 14 | 21 | 36 |
| 9 | Broiler | 1.0 | Day 14 | 21 | 36 |
| 10 | Broiler | 1.0 | Day 14 | 21 | 36 |
| 11 | Broiler | 1.0 | Day 14 | 21 | 36 |
| 12 | Broiler | 1.0 | Day 14 | 21 | 36 |
| 13 | Broiler | 0.3 | Day 14 | 21 | 36 |
| 14 | Broiler | 0.3 | Day 14 | 21 | 36 |
| 15 | Broiler | 0.3 | Day 14 | 21 | 36 |
| 16 | Broiler | 0.3 | Day 14 | 21 | 36 |
| 17 | Broiler | 0.3 | Day 14 | 21 | 36 |
| 18 | Broiler | 0.3 | Day 14 | 21 | 36 |
| 19 | Broiler | 0.1 | Day 14 | 21 | 36 |
| 20 | Broiler | 0.1 | Day 14 | 21 | 36 |
| 21 | Broiler | 0.1 | Day 14 | 21 | 36 |
| 22 | Broiler | 0.1 | Day 14 | 21 | 36 |
| 23 | Broiler | 0.1 | Day 14 | 21 | 36 |
| 24 | Broiler | 0.1 | Day 14 | 21 | 36 |
| 25 | Broiler | Salin. | Day 14 | 21 | 36 |
| 26 | Broiler | Salin. | Day 14 | 21 | 36 |
| 27 | Broiler | Salin. | Day 14 | 21 | 36 |
| 28 | Broiler | Salin. | Day 14 | 21 | 36 |
| 29 | Broiler | Salin. | Day 14 | 21 | 36 |
| 30 | Broiler | Salin. | Day 14 | 21 | 36 |
| 31 | Broiler | Salin. + Zn B | Day 14 | 21 | 36 |
| 32 | Broiler | Salin. + Zn B | Day 14 | 21 | 36 |
| 33 | Broiler | Salin. + Zn B | Day 14 | 21 | 36 |
| 34 | Broiler | Salin. + Zn B | Day 14 | 21 | 36 |
| 35 | Broiler | Salin. + Zn B | Day 14 | 21 | 36 |
| 36 | Broiler | Salin. + Zn B | Day 14 | 21 | 36 |
| 37 | Broiler | — | Seeder | — | 50 |
| 38 | Broiler | — | Seeder | — | 50 |

TABLE 12

Schedule of events

| Approx. Study Day | Event |
|---|---|
| Pre-study | Receipt of formulation. Receipt of Animal Ethics approval Field samples of *coccidial* oocysts (*Eimeria* species from chickens) are obtained in 2% potassium chromate. |
| −20 | Thirty 1-day-old meat chickens obtained and placed in battery brooder cages at trial facility at 10 chicks per cage. Commence unmedicated ration. |
| −11 | Sporulated oocysts administered by gavage. |
| −6 | Birds are euthanized and intestinal tracts removed and placed into 2% potassium chromate at 4 degrees Celsius. |
| −1 | Oocysts sporulated and examined under microscope and counted. |
| 0 | Broiler chicks hatched (Ross). Broiler chicks randomized into trial facility and randomized into each of 30 floor pens, placed at 36 chicks per pen. |
| 0, 14, 21, 28 and 42 | Birds are weighed on a pen basis. |
| 1-14 | Commence appropriate medicated feed (Starter ration) - all Groups. |
| 1-42 | Twice daily observation - all Groups. |
| 6 | The birds in the seeder pens are given oocyst inoculum by individual gavage (approximately 0.5 mL per bird) using a stepper pipette. |
| 12, 13 and 14 | Litter in the seeder pens is lightly raked |
| 14 | Top 2-3cm of the litter in the seeder pens collected and mixed together and weighed. Total litter weight is divided into 30 and that amount of litter distributed into each of the trial pens. Four subsamples of the mixed litter are collected and oocysts counts are performed. |
| 14, 21, 28 and 42 | Feed consumptions are measured. Feed conversion ratios are calculated over each time period. |
| 15-28 | Commence appropriate medicated feed (Grower ration) - all Groups. |
| 21 | Four birds randomly selected from each trial pen are humanely euthanized and their intestines and caeca scored for coccidiosis lesions in four gut segments (upper, mid and lower intestine and caeca) and lesions typical of *Eimeria* species noted. General gut quality (looking for enteritis) is also visually assessed. Four individual faecal samples per pen are collected and evaluated for oocyst count. |
| 29-42 | Commence appropriate medicated feed (Finisher ration) - all Groups |
| 42 | All surviving birds are euthanized and their carcasses disposed of. |

The residue level of IRP0001 can be determined by experiment as follows:

Samples of muscle from breast, leg and thigh, and liver and kidney are excised from each bird after euthanasia. A known weight of tissue (approximately 1 g) is homogenized in 2 mL water. Samples are centrifuged and a known volume of the supernatant is removed for analysis of IRP001 by LC-MS/MS to provide the residue level of berberine in muscle tissue (ng of berberine per g of muscle tissue).

Residue Study

This study and protocol aim to determine the residue depletion profile for a naturally occurring IVP administered at the maximum label dose rate through quantification of the marker tissue residue in broiler chickens treated via feed administration over a full production cycle.

BACKGROUND

Antimicrobials are used extensively for animal husbandry purposes for the control and prevention of potentially lethal outbreaks of diseases in the intensive livestock industry. Some see this as a cause for the development of resistant microbes, with government regulators now implementing directives in controlling the use of these antimicrobial agents.

The Inventors have identified several naturally occurring compounds which can be used as natural antibiotics to replace the current antibiotics used in food producing animals, such as poultry and pig.

Candidate formulations undergo testing to meet the regulatory standards as required, for example, by the Australian Pesticides & Veterinary Medicines Authority (APVMA) and US Food and Drug Administration (FDA). In this regard, determination of the residue depletion profiles of animal health treatments is an essential part of the product development process. This allows government regulatory authorities to set appropriate with-holding periods (WHPs) to protect both human health and agricultural trade.

IRP001 has been selected as a candidate IVP as it is well established to be safe and non-toxic. Poultry have been selected as the target animal species due to widespread reliance on antimicrobials in the chicken industry to prevent or treat a number of diseases caused by enteric pathogens. These clinically significant enteric pathogens may potentially respond to IRP001.

Compliance

This tissue residue depletion study is to be conducted according to the agreed protocol utilizing SOPs and good scientific practice.

Study Design a. Experimental Unit: Both the experimental and observational unit will be the individual animal. The statistical unit will be the treatment group.

b. Animal Model: Feed intake, daily water consumption, weight change, mortality and marker residue in tissues will be used as outcome parameters.

c. Inclusion Criteria: Animals will be selected for the study if they meet the criteria outlined in section 10 below.

d. Exclusion and Removal Criteria: Animals that, on receipt, are debilitated, suffering from disease, injury, or otherwise unsuitable for inclusion in the study, in the opinion of the Investigator, will be excluded.

Subsequent to selection, animals that may be deemed unsuitable for continuation in the study will only be removed with the documented concurrence of the Sponsor or Investigator. The reason for any removal will be fully documented and justified in the raw data and Study Report. Any animal that is removed from the study will receive appropriate veterinary care.

e. Allocation: Broiler Chicks: On receival the one hundred and eighty (180) broiler chicks that meet the inclusion criteria shall be sequentially allocated as they are removed from the transport container to eighteen (18) individual treatment groups, each of ten (10) birds. The method of allocation and randomisation will be described in the raw data and Study Report.

f. Blinding: Not applicable.

Investigational Veterinary Product (IVP)

All formulation details including batch number, expiry date, receipt and usage are recorded.

a. Investigational Veterinary Product: IRP001 Cl as 100% IRP001 Cl.

b. Source: The IVP will be supplied by the Sponsor.

c. Storage: The IVP shall be stored at ambient temperature in a temperature designated area.

The storage location and conditions of the IVP are recorded.

d. Safety: A SDS or its equivalent (if available) is provided by the Sponsor.

e. Assays: A Certificate of Analysis (if available) is provided for the IVP.

f. Drug Disposal: The disposal of all remaining IVP is recorded.

Treatment a. Dose Calculation: Doses are based on fixed concentrations of IRP001 Cl in feed (0.03 or 0.1 g/kg IRP001 Cl).

b. Dose Preparation: Powdered IRP001 Cl are incorporated with raw commercial feed ingredients then thoroughly mixed in, for example a "concrete mixer" type apparatus, to provide the final concentrations in feed as outlined.

c. Method of Dose Administration: Study animals are dosed according to the treatment regime detailed in Table 1 below. Medicated feed will be provided to chickens in the relevant treatments ad libitum as their sole source of feed.

TABLE 13

Treatment regime-feed conversion ratio

| Grp. | Bird type | Treatment | IVP concentration in feed g/kg | Euth*. (Day) | Trt. In feed Days | No. Animals |
| --- | --- | --- | --- | --- | --- | --- |
| 1 | Broiler | IVP | 0.03 | 35 | 0-35 | 10 |
| 2 | Broiler | IVP | 0.03 | 36 | 0-35 | 10 |
| 3 | Broiler | IVP | 0.03 | 37 | 0-35 | 10 |
| 4 | Broiler | IVP | 0.03 | 39 | 0-35 | 10 |
| 5 | Broiler | IVP | 0.03 | 42 | 0-35 | 10 |
| 6 | Broiler | IVP | 0.03 | 42 | 0-28** | 10 |
| 7 | Broiler | IVP | 0.3 | 35 | 0-35 | 10 |
| 8 | Broiler | IVP | 0.3 | 36 | 0-35 | 10 |
| 9 | Broiler | IVP | 0.3 | 37 | 0-35 | 10 |
| 10 | Broiler | IVP | 0.3 | 39 | 0-35 | 10 |
| 11 | Broiler | IVP | 0.3 | 42 | 0-35 | 10 |
| 12 | Broiler | IVP | 0.3 | 42 | 0-28** | 10 |
| 13 | Broiler | IVP | Control | 35 | 0-35 | 10 |
| 14 | Broiler | IVP | Control | 36 | 0-35 | 10 |
| 15 | Broiler | IVP | Control | 37 | 0-35 | 10 |
| 16 | Broiler | IVP | Control | 39 | 0-35 | 10 |
| 17 | Broiler | IVP | Control | 42 | 0-35 | 10 |
| 18 | Broiler | IVP | Control | 42 | 0-28** | 10 |

*Euthanasia

**Note:

Medicated feed is withdrawn from Groups 6 and 12 on Day 28 to allow a 14 day washout period for these groups.

Schedule of Events

TABLE 14

Schedule of events

| Approx. Study Day | Event |
| --- | --- |
| Pre-study | Receipt of formulation. Receipt of Animal Ethics Committee approval. |

TABLE 14-continued

Schedule of events

| Approx. Study Day | Event |
|---|---|
| 0 | Broiler chicks hatched. Broiler chicks transported and placed into temperature controlled floor pens. Birds weighed (by treatment group). Commence twice daily health observations. |
| Days 0-49 | Weigh daily feed added and calculate daily feed intake by treatment group. Measure daily water volume and calculate daily water intake by treatment group. |
| 7, 14, 21, 28 and 35 | Weigh all birds - Groups 1 through Group 18 inclusive. Record individual bird bodyweight. |
| Day 28 | Groups 6 and 12. Cease medicated feed thus allowing 14 day washout period when sacrificed at Day 42. |
| Day 35 | Weigh all birds - Groups 1 through Group 18 inclusive. Withdraw medicated feed from all groups. |
| 9.00am | At the point of medicated feed withdrawal euthanise, conduct individual clinical examination and gross visual pathological assessment on the six heaviest birds in Groups 1, 7 and 13. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 36 | Euthanise, conduct individual clinical examination and gross visual pathological assessment on the six heaviest birds in Groups 2, 8 and 14. Collect tissues - liver, |
| 9.00am | kidney, breast muscle (1) leg muscle (2) [upper and lower thigh] and skin (feathers removed, intact with any subcutaneous fat). Store frozen duplicate samples of tissues (<10 degrees Celsius). |
| Day 37 | Euthanise, conduct individual clinical examination and gross visual pathological assessment on the six heaviest birds in Groups 3, 9 and 15. Collect tissues - liver, |
| 9.00am | kidney, breast muscle (1) leg muscle (2) [upper and lower thigh] and skin (feathers removed, intact with any subcutaneous fat). Store frozen duplicate samples of tissues (<10 degrees Celsius). |
| Day 39 | Euthanise, conduct individual clinical examination and gross visual pathological assessment on the six heaviest birds in Groups 4, 10 and 16. Collect tissues - liver, |
| 9.00am | kidney, breast muscle (1) leg muscle (2) [upper and lower thigh] and skin (feathers removed, intact with any subcutaneous fat). Store frozen duplicate samples of tissues (<10 degrees Celsius). |
| Day 42 | Euthanise, conduct individual clinical examination and gross visual pathological assessment on the six heaviest birds in Groups 5, 11 and 17. Collect tissues - liver, |
| 9.00am | kidney, breast muscle (1) leg muscle (2) [upper and lower thigh] and skin (feathers removed, intact with any subcutaneous fat). Store frozen duplicate samples of tissues (<10 degrees Celsius). |
| Day 42 | Euthanise, conduct individual clinical examination and gross visual pathological assessment on the six heaviest birds in Groups 6, 12 and 18. Collect tissues - liver, |
| 9.00am | kidney, breast muscle (1) leg muscle (2) [upper and lower thigh] and skin (feathers removed, intact with any subcutaneous fat). Store frozen duplicate samples of tissues (<10 degrees Celsius). |

Test System

Animal details are recorded in the raw data. That is: Species, broiler chickens; Number, 180; Source, commercial (one batch of 90); Age, one day old.

Animal Management a. Animal Welfare: Study animals are managed similarly and with due regard for their welfare. Study animals are observed according to Animal Ethics Committee (AEC) requirements and a "Record of Animal Care" is completed.

b. Health Management: Any routine prophylactic treatments are given as soon as possible, if necessary, and recorded (product name, batch number, expiry date, dose, route and date(s) of administration).

The study animals are observed twice daily according to the standard operating protocol (SOP) in place commencing on Day 0. Any health problem that requires further examination are recorded.

All health problems and adverse events must be reported to the Investigator within one working day. Any adverse event characterised by the Investigator as product related, results in death, is life-threatening, involves a large number of animals, or is a human adverse event, must be recorded and reported to the Sponsor and AEC within one working day.

Normal veterinary care and procedures may be performed and are described in the raw data. Concurrent medications may be administered for standard management practice and humane reasons, with prior approval from the Investigator, and Sponsor (if relevant). No treatments similar to the IVP are administered. All concurrent medications are recorded giving identity of materials used (product name, batch number and expiry date), animal ID(s), the reason for use, route of administration, dose and the date(s) administered, and are included in the raw data (Trial Log) and the Study Report.

If an injury or illness results in euthanasia or death of a study animal, this should be recorded and a post-mortem conducted, if possible, by a veterinarian. A "Post Mortem Report", including the probable cause of death, is included in the raw data.

All health problems, adverse events and animal mortality, including their relationship to treatment, are included in the Study Report.

c. Housing: Chickens are kept in purpose built chicken floor pens by treatment group in two separate and discrete controlled environment rooms at an approved animal facility. One room houses all unmedicated Groups 13 to 18 inclusive birds with the second room housing all medicated birds—Groups 1 to 12 inclusive. Each pen has a floor space of approx. 1.5 m². Chickens are raised on litter according to normal commercial practice.

There are 18 floor pens, 10 chickens per pen up to Day 49. The maximum chicken weight of each pen at study conclusion is well below the recommended maximum of 40 kg/m² for meat chickens in the Australian Code of Practice.

Note-birds in Groups 13 to 18 inclusive (untreated control animals) are maintained in a similar, but physically separate isolation room to medicated Groups 1 to 12 birds thus ensuring no cross contamination during the study.

d. Experimental diets: A formulated commercial starter then grower ration is fed throughout the study. A copy of a feed bag label, or equivalent, showing feed composition, is included in the raw data.

e. Feed and Water Intake: Weigh and record daily feed added and calculate daily feed intake by treatment group. Measure and record daily water volume and calculate daily water intake by treatment group.

f. Animal Disposal: Study animals are humanely euthanised according to AEC approval and recorded at the intervals as outlined in the Schedule of Events (Table 14).

Study Procedures a. Trial Log: All scheduled and unscheduled events during the study are recorded.

Assessment of Effects a. Body Weights: Chickens are weighed on Days 0 (Group weight) and 7, 14, 21, 28 and 35 days—individual animal weights are recorded. Weigh scales are checked pre- and post-weighing with calibrated test weights and recorded. Body weights at study termination are compared between groups to determine treatment effects (if any).

b. Examinations: Individual clinical examinations are performed on euthanasia at the time of gross pathology and tissue collection. Clinical examinations are recorded. Digital still images may be recorded as appropriate.

c. Observations: Birds are inspected twice daily for general well-being, typically prior to 8 am of a morning, and after 4 μm of an afternoon. Thus a typical interval between observations would be 9 hours during the day, and 15 hours overnight. Birds showing abnormal clinical signs are recorded, observed closely and euthanized if deemed to be suffering significantly (e.g. marked depression with low likelihood of recovery) by the Investigator.

d. Necropsy Examinations: All birds are euthanized and necropsied between Days 35 and 49 as per schedule—Table 14.

e. Gross Pathology: All chickens from all Group 1 through 18 are necropsied and examined for gross visual pathological changes which are described and scored as appropriate by individual bird.

f. Tissue Residue Analysis: Duplicate representative samples of liver, kidney, breast muscle (1), leg muscle (2) [upper and lower thigh] and entire skin with fat intact will be collected and stored frozen (<10 degrees Celsius) from the six (6) heaviest birds in each group (Groups 1 to 18 inclusive) as per schedule, table 1 for subsequent marker residue analysis. Groups 13 to 18 birds shall be sacrificed at Day 35 as untreated control birds with tissues collected for tissue assay requirements.

Samples will be labelled with adhesive labels listing the study number, animal ID, time point, date, sample type and replicate.

For residue analysis, samples are thawed and a known weight of tissue (approximately 1 g) homogenized in 2 ml water. Samples are centrifuged and a known volume of the supernatant removed for analysis by LC-MS/MS.

TABLE 15

| | | Analytical matrix | | | | | |
|---|---|---|---|---|---|---|---|
| Sacrifice Time (Days) | Group | IRP001 HCl (Marker residue) | | | | | |
| | | Liver | Kidney | Breast Muscle | Upper leg Muscle | Lower leg Muscle | Skin (entire) |
| 0 | 1 | ☑ | ☑ | ☑ | ☑ | ☑ | ☑ |
| 1 | 2 | ☑ | ☑ | ☑ | ☑ | ☑ | ☑ |
| 2 | 3 | ☑ | ☑ | ☑ | ☑ | ☑ | ☑ |
| 4 | 4 | ☑ | ☑ | ☑ | ☑ | ☑ | ☑ |
| 7 | 5 | ☑ | ☑ | ☑ | ☑ | ☑ | ☑ |
| 14 | 6 | ☑ | ☑ | ☑ | ☑ | ☑ | ☑ |
| 0 | 7 | ☑ | ☑ | ☑ | ☑ | ☑ | ☑ |
| 1 | 8 | ☑ | ☑ | ☑ | ☑ | ☑ | ☑ |
| 2 | 9 | ☑ | ☑ | ☑ | ☑ | ☑ | ☑ |
| 4 | 10 | ☑ | ☑ | ☑ | ☑ | ☑ | ☑ |
| 7 | 11 | ☑ | ☑ | ☑ | ☑ | ☑ | ☑ |
| 14 | 12 | ☑ | ☑ | ☑ | ☑ | ☑ | ☑ |
| 0 | 13 | ☑[a] | ☑[a] | ☑[a] | ☑[a] | ☑[a] | ☑[a] |
| 1 | 14 | ☑[a] | ☑[a] | ☑[a] | ☑[a] | ☑[a] | ☑[a] |
| 2 | 15 | ☑[a] | ☑[a] | ☑[a] | ☑[a] | ☑[a] | ☑[a] |
| 4 | 16 | ☑[a] | ☑[a] | ☑[a] | ☑[a] | ☑[a] | ☑[a] |
| 7 | 17 | ☑[a] | ☑[a] | ☑[a] | ☑[a] | ☑[a] | ☑[a] |
| 14 | 18 | ☑[a] | ☑[a] | ☑[a] | ☑[a] | ☑[a] | ☑[a] |
| Total | | 31 | 31 | 21 | 46 | 46 | 175 |

[a] To be analysed if required for assay validation and verification.

g. Sample Storage, Transfer & Disposal: Sample storage, transfer and disposal are recorded. Replicate 1 tissue samples are shipped frozen on wet ice to the Analytical Laboratory at times outlined in Section 10. Samples are transferred according to the standard operating protocol (SOP) with an accompanying temperature data logger and frozen water vial. Replicate 2 tissue samples are retained frozen for a period of 6 months after the last sample collection time-point. Beyond that point they may be discarded at the study site's discretion unless specifically requested not to by the Sponsor's Representative.

Statistical Analysis

Methods are documented in the Study Report.

Data Records

Protocol specifications are to supersede facility SOPs. Study forms may be added or amended as required during the study without the need for a Protocol Amendment or Deviation.

a. Protocol Approval: The Protocol is approved and signed by all relevant personnel (see page 1) prior to study start.

b. Amendments/Deviations: An amendment is a change or modification of the Protocol made prior to execution of the changed or modified task. Amendments must state the reason for the change and have documented authorisation from the Sponsor. The amendment must be signed by the Investigator, and the Sponsor.

Deviations from this Protocol or applicable SOPs are to be documented, signed and dated by the Investigator at the time the deviation(s) are identified. An assessment on the impact on the overall outcome or integrity of the study will be made. Deviations must be communicated to the Sponsor as soon as practically possible.

All Protocol amendments and deviations are recorded accordingly and numbered sequentially based on the date of occurrence or date of identification.

c. Notes to File: Notes to File are recorded accordingly to clarify events or circumstances that may not otherwise be apparent from the raw data. Notes to File must be communicated to the Sponsor as soon as practically possible.

d. Change of Study Personnel: Change of the study Investigator, or other responsible study personnel, is to be recorded accordingly.

e. Raw Data: All original raw data pages are paginated, identified with the study number and signed and dated by the person making the observation and by the person recording the information.

f. Communication Log: The Investigator maintains copies of all correspondence relating to the study. Any telephone conversations that result in a change in the documentation, design, conduct, or reporting of the study, are recorded.

g. Permits: The study detailed in this Protocol is to be covered by government agency permit (for example an APVMA small trial permit).

Study Report

A Study Report is prepared by the Investigator, or designee. Data listings of each variable measured us included. The study Investigator's Compliance Statement is included in the Study Report. The original signed Study report with raw data and Statistical Report appended is submitted to the Sponsor and archived.

*Salmonella* and *Campylobacter* Studies

The present disclosure also contemplates the prevention or treatment of infectious disease caused by *Salmonella* or *Campylobacter*. Studies for investigating the effectiveness of berberine alkaloids or berberine alkaloid compositions in preventing or treating disease caused by *Salmonella* or *Campylobacter* infection are described below. The studies are modelled on published protocols: Alali, W. Q et al. "Effect of essential oil compound on shedding and colonization of *Salmonella* enteric serovar heidelberg in broilers", *Poultry Science*, 2013, 92:836-841; Berghaus, R. et al. "Enumeration of *Salmonella* and *Campylobacter* in environmental farm samples and processing plant carcass rinses from commercial broiler chicken flocks", *Appl. Environ. Microbiol.* 2013, 1-37; Cochran, W. G., and G. M. Cox, *Experimental Design.* 2$^{nd}$ Ed. John Wiley & Sons, New York, NY. Pages 582-583, 1992 (Cochran and Cox, 1992).

*Salmonella* Study

The objective of this study is to evaluate the effectiveness of IVPs as a means to control *Salmonella heidelberg* in broiler birds.

Experimental Design

In this twelve (12) pen study, six hundred (600) chicks are assigned to three (3) treatment groups, with four (4) replicate blocks, and allocated into groups of fifty (50) birds per pen.

Treatment groups are assigned to pens using randomized complete block design (Cochran and Cox, 1992). Treatment groups are as follows:

1. No Treatment—*Salmonella heidelberg* Challenge Control
2. Treatment 1—*Salmonella heidelberg* Challenge
3. Treatment 2—*Salmonella heidelberg* Challenge The study begins when birds are placed (day-of-hatch; DOT 0), at which time birds are allocated to experimental pens. Only healthy appearing birds are allocated for study use and final number and disposition of all birds not allocated are documented. No birds are replaced during the course of the study. Bird weights (kg) by pen are recorded at study initiation (DOT 0), DOT 35, and termination (DOT 42).

Materials and Methods

BIRDS. Six hundred (600) day-of-hatch Ross×Ross straight-run broiler chicks are obtained. Birds receive routine vaccinations (HVTSB1) and breeder flock number information is recorded. All birds are vaccinated with a commercial coccidiosis vaccine at recommended dose.

HOUSING AND ENVIRONMENTAL CONTROL. At study initiation, fifty (50) broiler chicks will be allocated to twelve (12) floor pens measuring 5×10 (1.00 ft$^2$/bird stocking density) in a modified conventional poultry house with solid-sides and dirt floors. The facility is fan-cooled. Thermostatically controlled gas heaters are the primary heat source. Supplemental heat lamps (one [1] lamp per pen) provide heat (when needed). Birds are raised under ambient humidity and are provided a lighting program as per the primary breeder recommendations. At placement, each pen contains approximately four (4) inches of fresh pine shavings. Litter is not replaced during the study course. Each pen contains one (1) tube feeder and one (1) bell drinker resulting in a fifty (50) bird/feeder and drinker ratio.

FEED AND WATERING METHOD. ad libitum.

DIETS. Rations are fed as follows: starter DOT 0 through DOT 14, grower DOT 14 through DOT 35, and finisher DOT 35 to DOT 42. Diets are fed as crumbles (starter feed) or pellets (grower and finisher). Feed formulations for this study consist of unmedicated commercial-type broiler starter, grower, and finisher diets compounded with appropriate feedstuffs, calculated analyses to meet or exceed NRC standards, and no antibiotics are added to any feed unless specifically stated as a treatment protocol component. Experimental treatment feeds are prepared from a basal starter feed with quantities of all basal feed and test articles used to prepare treatment batches documented. To assure uniform distribution of all test articles treatment feeds are mixed and pelleted in a California Pellet Mill at 80° C. (with pellet temperature recorded). After mixing is completed feed is distributed among pens of designated treatment groups. Test article(s) are stored in a SPRG climate controlled storage area. All diets, formulations, and other feed information are documented.

FEED CHANGES. Birds receive treatment-appropriate feed from DOT 0 to DOT 42. Rations are changed from starter to grower on DOT 14 and from grower to finisher on DOT 35. At that time all previous feed is removed from each pen, individually weighed, and replaced with finisher feed. On DOT 42 all non-consumed finisher feed is removed from pens, individually weighed, and discarded.

SALMONELLA INOCULATION. On DOT 0 twenty-five (25) chicks per pen (50% seeders) are tagged, color-coded (for identification), and orally dosed (gavaged) with a 107 CFU nalidixic acid-resistant Salmonella heidelberg.

SALMONELLA SAMPLING. Bootsocks swab samples are collected for Salmonella environmental contamination determination from all pens DOT 14 and DOT 42. Gloves are changed between completion of each swab to reduce potential sample cross contamination. A pre-moistened boot-sock swab (Solar Biologicals, Inc., Cat #BT SW-001) is removed from sterile bag, placed onto foot covered with a clean new plastic boot, the perimeter and interior of pen walked, boot sock removed, and placed into sterile bag labeled with pen number. After repeating the procedure for each pen, samples are appropriately stored and then submitted for Salmonella analysis.

CECAL SALMONELLA CULTURES. Cecal sampling is completed on DOT 42. On DOT 42 ten (10) horizontal-exposed (non-tagged) birds are taken from each individual pen, euthanized (by cervical dislocation), and the ceca of each bird is aseptically removed. After removal the cecal sample is placed in one (1) sterile plastic sample bag (Fisher Scientific), labeled, stored on ice, and submitted for Salmonella analysis.

SALMONELLA ISOLATION AND IDENTIFICATION. All samples submitted for Salmonella isolation and identification (bootsock swabs and/or ceca) are stored on ice in sterile Whirl Pack bags prior to analysis. Upon arrival tetrothionate broth is added to bootsock swab samples while cecae are weighed, sterile saline added, and the sample stomachered. A one (1) mL aliquot is removed for MPN analysis, a 10× tetrothionate broth (Difco) solution added, and samples are incubated overnight at 41.5° C. A loopful of sample is struck onto xylose lysine tergitol-4 agar (XLT-4, Difco) plates which are incubated overnight at 37° C. Up to 3 (three) black colonies are selected and confirmed as Salmonella positives using Poly-O Salmonella Specific Antiserum (MiraVista, Indianapolis, IN). (Berghaus et al., 2013; Alali et al., 2013)

SALMONELLA ENUMERATION PROCEDURE (MPN METHOD). For all ten (10) horizontal-exposed (non-tagged) and five (5) direct challenged (tagged) samples, a one (1) ml sample of stomachered peptone broth is transferred to three (3) adjacent wells in the first row of a 96-well two (2) ml deep block. A 0.1 ml aliquot of sample is transferred to 0.9 ml of tetrothionate broth in the second row, repeat process for remaining rows (to produce five (5) ten-fold dilutions), and incubate blocks (24 hours at 42° C.) (Table 16). Transfer one (1) µl of each well onto XLT-4 agar (containing nalidixic acid) with a pin-tool replicator, incubate plates (37° C. for 24 hours), record final dilution of each sample, and enter in MPN calculator (to determine sample MPN). Suspect Salmonella isolates are confirmed by Poly-O Salmonella Specific Antiserum (MiraVista, Indianapolis, IN). (Berghaus et al., 2013; Alali et al., 2013).

TABLE 16

Salmonella enumeration

|  |  | 1 | 2 | 3 | 4 | 5 | 6 | 7 | 8 | 9 | 10 | 11 | 12 |  |
|---|---|---|---|---|---|---|---|---|---|---|---|---|---|---|
| Sample 1 | A | ○ | ○ | ○ | ○ | ○ | ○ | ○ | ○ | ○ | ○ | ○ | ○ | Sample 3 |
|  | B | ○ | ○ | ○ | ○ | ○ | ○ | ○ | ○ | ○ | ○ | ○ | ○ | Sample 4 |
|  | C | ○ | ○ | ○ | ○ | ○ | ○ | ○ | ○ | ○ | ○ | ○ | ○ |  |
| Sample 2 | D | ○ | ○ | ○ | ○ | ○ | ○ | ○ | ○ | ○ | ○ | ○ | ○ |  |
|  | E | ○ | ○ | ○ | ○ | ○ | ○ | ○ | ○ | ○ | ○ | ○ | ○ | Sample 5 |
|  | F | ○ | ○ | ○ | ○ | ○ | ○ | ○ | ○ | ○ | ○ | ○ | ○ |  |
| Sample 3 | G | ○ | ○ | ○ | ○ | ○ | ○ | ○ | ○ | ○ | ○ | ○ | ○ |  |
|  | H | ○ | ○ | ○ | ○ | ○ | ○ | ○ | ○ | ○ | ○ | ○ | ○ | Negative Control |

DISEASE & COCCIDIA CONTROL. All birds are vaccinated at one (1) day of age by spray cabinet with a USDA-approved coccidian vaccine. No concomitant drug therapy is used during the study. To prevent cross-contamination, plastic disposable boots are worn when entering pens and changed between each pen.

BIRD IDENTIFICATION. The pen is the unit of measure. Pen security will prevent bird migration.

MONITORING. All birds are monitored for general flock condition, temperature, lighting, water, feed, litter condition, and unanticipated house conditions/events. Findings are documented twice daily during the regular working hours (one [1] observation recorded on final study day). One (1) observation is recorded Saturday, Sunday, and observed holidays.

MORTALITY. Pens are checked daily for mortality. Birds are culled only to relieve suffering. The date and removal weight (kg) are recorded for any bird culled (or found dead), gross necropsy is performed on all culled (or dead) birds, and the following information recorded: gender and probable cause of death.

BIRD AND FEED DISPOSITION. All birds, mortalities and remaining feeds (including mixer flushes) are disposed of by appropriate and ethical methods.

SOURCE DATA CONTROL AND HANDLING. Data is recorded in indelible ink with legible entries, each source data sheet signed (or initialed), and dated by individual recording entry. All source data errors (and/or changes) are initialed, dated, and a brief explanation statement or error code written directly on the form.

DATA MANAGEMENT. Data management and statistical analysis of weight gain, feed consumption, feed conversion, and Salmonella results are performed.

Calendar of Events

TABLE 17

*Salmonella study calendar of events*

| DOT DATE | GENERAL DESCRIPTION OF EVENTS |
|---|---|
| 0 | ⇒ Weigh and issue starter feed |
|  | ⇒ Pick up chicks from hatchery |
|  | ⇒ Group into sets of three (3) with four (4) replicates per treatment group |
|  | ⇒ Spray vaccinate with a commercial broiler coccidiosis vaccine |
|  | ⇒ Weigh birds by pen and place in appropriate pens |
|  | ⇒ Tag (and dye) twenty-five (25) birds per pen for identification and orally gavage with a $10^7$ CFU per chick of a nalidixic acid-resistant *Salmonella heidlberg* |
| 14 | ⇒ Collect bootsock swab samples from all pens |
|  | ⇒ Weigh and discard all nan-consumed starter feed and replace with grower feed |
| 35 | ⇒ Weigh and discard all non-consumed grower feed and replace with finisher feed |
|  | ⇒ Weigh birds by pen |
| 42 | ⇒ Collect bootsock swab samples from all pens |
|  | ⇒ Weigh birds by pen |
|  | ⇒ Weigh and discard all non-consumed grower feed |
|  | ⇒ Collect ceca samples (ten [10] horizontal-exposed [nontagged] and five [5] direct-exposed [tagged] birds per pen) from all study pens |
|  | ⇒ Terminate trial |

*Campylobacter* Study

The study is to determine the efficacy of Investigational Veterinary Products (IVPs) to reduce *Campylobacter jejuni* shed (horizontal transmission) and colonization in broiler ceca.

Experimental Design

One hundred twenty (120) day of age (non-SPF) commercial broilers are received. Five (5) birds are euthanized by cervical dislocation and their ceca are cultured for *C. jejuni*. The remaining selected one hundred five (105) birds are randomized into three (3) groups in one isolation room subdivided into one-thirds, with thirty-five birds per group. Experimental variables are shown below. All birds are fed a broiler starter crumble diet with treatment as specified below.

NUMBER OF ROOMS—1 Subdivided into 3 bird spaces
TOTAL NUMBER OF CHICKS—120
NUMBER OF CHICKS IMMEDIATELY EUTHANIZED—05
NUMBER OF BIRDS TO BE SUBDIVIDED INTO TREATMENT GROUPS—105 TREATMENT GROUPS—3
REPLICATE BLOCKS—N/A
BIRDS PER ROOM SUBDIVISION—35
TREATMENT GROUPS
  1. No Treatment—*Campylobacter jejuni* Challenge
  2. Treatment 1—*Campylobacter jejuni* Challenge
  3. Treatment 2—*Campylobacter jejuni* challenge Materials and Methods BIRDS. One hundred ten (110) day-of-hatch Ross 708 male broiler chicks are obtained. Birds are sexed, receive routine vaccinations (HVTSB1), and breeder flock number information is recorded. Birds receive one (1) dose of a commercially approved Coccidia vaccine one (1) day of age according to manufacturer recommendations.

HOUSING AND ENVIRONMENTAL CONTROL. At study initiation, one hundred five (105) day-of-hatch Ross 708 male broiler chicks are allocated to one (1) isolation room. The room is subdivided into three (3) equal bird spaces. Thirty-five (35) chicks per space are placed in each room. Each room measures 13.4'×15.7' (approximately 2.0 $foot^2$ stocking density). The isolation room environment is controlled by an independent HEPA filtration system and heat pump unit with one (1) heat lamp providing supplemental heat during brooding. Birds are reared under ambient humidity. At placement, each pen contains approximately four (4) inches of kiln-dried bagged fresh pine shavings. Litter is not replaced during the course of this study. Each space contains one (1) tube feeder and one (1) bell drinker (35 bird/feeder and drinker ratio). Birds are provided lighting twenty-four (24) hours per day.

FEED AND WATERING METHOD. ad libitum.

DIETS. Birds are fed a broiler starter diet throughout the study. An unmedicated commercial-type broiler starter diet compounded with appropriate feedstuffs with calculated analyses to meet or exceed NRC standards, and the addition of no antibiotics any feed unless specifically stated as a treatment protocol component is formulated. Feed is prepared from a basal starter feed. After mixing is completed, feed is distributed among pens of designated treatment groups. Test article(s) are stored in a climate controlled area. All diets and formulations and feeds are documented.

FEED CHANGES. Birds receive starter feed from DOT 0 to DOT35.

METHOD OF *CAMPYLOBACTER JEJUNI* ADMINISTRATION: On DOT 14, 35 birds per treatment are orally gavaged with 0.1 ml of *Campylobacter jejuni* JB strain broth containing approximately $10^6$ CFU/ml (chick dose of approximately $10^5$ CFU/ml).

*CAMPYLOBACTER* COLONIZATION EVALUATION: On DOT 0 five (5) birds are cultured for *Campylobacter jejuni* prevalence: DOT 35, thirty-three (33) birds per treatment are euthanized by cervical dislocation. The ceca of each bird is aseptically removed and placed into sterile plastic sampling bags (Fisher Scientific) for *Campylobacter* isolation analysis. All samples are stored on ice prior to *Campylobacter* analysis.

*CAMPYLOBACTER* ENUMERATION PROCEDURE: *CAMPYLOBACTER* ENUMERATION PROCEDURE (DIRECT COUNT). For each sample a one (1) ml sample of stomachered Bolton broth will be transferred to three (3)

adjacent wells in the first row of a 96-well two (2) ml deep block. A 0.1 ml aliquot of sample is transferred to 0.9 ml of Bolton broth in the second row, process is repeated for remaining rows (producing twelve (12) ten-fold dilutions), and then 0.1 ml from each well will be spread-plated onto Campy Cefex Agar (Table 18). Plates are incubated (42° C. for 24 hours) in the presence of *Campylobacter* gas, final dilution of each sample recorded. Suspect *Campylobacter* isolates are confirmed by gram stain.

TABLE 18

*Campylobacter* enumeration

|  |  | 1 | 2 | 3 | 4 | 5 | 6 | 7 | 8 | 9 | 10 | 11 | 12 |  |
|---|---|---|---|---|---|---|---|---|---|---|---|---|---|---|
| Sample 1 | A | ○ | ○ | ○ | ○ | ○ | ○ | ○ | ○ | ○ | ○ | ○ | ○ | Sample 3 |
|  | B | ○ | ○ | ○ | ○ | ○ | ○ | ○ | ○ | ○ | ○ | ○ | ○ | Sample 4 |
|  | C | ○ | ○ | ○ | ○ | ○ | ○ | ○ | ○ | ○ | ○ | ○ | ○ |  |
| Sample 2 | D | ○ | ○ | ○ | ○ | ○ | ○ | ○ | ○ | ○ | ○ | ○ | ○ |  |
|  | E | ○ | ○ | ○ | ○ | ○ | ○ | ○ | ○ | ○ | ○ | ○ | ○ | Sample 5 |
|  | F | ○ | ○ | ○ | ○ | ○ | ○ | ○ | ○ | ○ | ○ | ○ | ○ |  |
| Sample 3 | G | ○ | ○ | ○ | ○ | ○ | ○ | ○ | ○ | ○ | ○ | ○ | ○ |  |
|  | H | ○ | ○ | ○ | ○ | ○ | ○ | ○ | ○ | ○ | ○ | ○ | ○ | Negative Control |

DISEASE CONTROL. No concomitant drug therapy will be used during the study. To prevent cross-contamination, plastic disposable boots will be worn when entering rooms and changed between each room.

BIRD IDENTIFICATION. The room is the unit of measure. Room security prevents bird migration.

MONITORING. All birds are monitored for general flock condition, temperature, lighting, water, feed, litter condition, and unanticipated house conditions/events. Findings are documented twice daily during the regular working hours (one [1] observation recorded Day 35). One (1) observation will be recorded Saturday, Sunday, and observed holidays.

MORTALITY. Rooms are checked daily for mortality. Birds are culled only to relieve suffering. The date and removal weight (kg) is recorded for any bird culled (or found dead), gross necropsy is performed on all culled (or dead) birds, and the following information is recorded: gender, and probable cause of death.

BIRD AND FEED DISPOSITION. All birds, mortalities and remaining feeds (including mixer flushes) are disposed of by appropriate methods.

SOURCE DATA CONTROL AND HANDLING. Data is recorded in indelible ink with legible entries, each source data sheet signed (or initialed), and dated by individual recording entry. All source data errors (and/or changes) are initialed, dated, and a brief explanation statement or error code written directly on the form.

DATA MANAGEMENT. Data management and statistical analysis of weight gain, feed consumption, feed conversion, and *Campylobacter* results are performed.

Calendar of Events

TABLE 19

*Campylobacter* calendar of events

| DOT DATE | GENERAL DESCRIPTION OF EVENTS |
|---|---|
| 0 | ⇒ Issue and weigh starter feed |
|  | ⇒ Pick up 110 mate broiler chicks from hatchery |
|  | ⇒ Coccidia vaccinate (one [1] dose per chick) |
|  | ⇒ Necropsy five (5) for *C. jejuni* presence |
|  | ⇒ Group into sets of three (3) with 35 chicks per group |
| 14 | ⇒ Gavage each bird in ail rooms with *Campylobacter jejuni* isolate JB Strain at 0.1 ml/chick of CFU/ml (approximately $10^5$ CFU/chick) |
| 35 | ⇒ Collect ceca samples from 33 birds per section of room of all treatment groups for *C. jejuni* enumeration |
|  | ⇒ Terminate trial |

EXAMPLES

Necrotic Enteritis

Necrotic Enteritis is an intestinal gut infection found in food-producing animals such as poultry. First described by Parish in 1961, it is caused in poultry by the bacteria, Clostridium perfringens and may present as acute clinical disease or subclinical disease. Although Clostridium perfringens is recognized as the etiological agent of Necrotic Enteritis, other contributing factors are usually required to predispose the animals to disease. It is accepted that Necrotic Enteritis is a multi-factorial disease process, with numerous risk factors including Eimeria infection, removal of antibiotic-growth promoters, environmental and management conditions, physiological stress and immunosuppression, and nature and form of diet.

A potentially fatal disease, Necrotic Enteritis can cause flock mortality rates up to 1% per day for several consecutive days during the last weeks of the rearing period, with total cumulative mortalities rising to 30-50%. In the subclinical form, damage to the intestinal mucosa leads to decreased digestion and absorption, reduced weight gain and increased feed conversion ratio, resulting in reduction of commercial performance. It is this manifestation of the disease that reportedly causes the greatest economic losses in the poultry production industry. In addition, Clostridium perfringens in poultry constitutes a risk for transmission to humans through the food chain, with Clostridium perfringens being one of the frequently isolated bacterial pathogens in foodborne disease outbreaks in humans.

Necrotic Enteritis was previously controlled by well-known antibacterial drugs such as virginiamycin, bacitracin, and so on. The banning of antibiotic use in food-producing animals in more and more countries has resulted in Necrotic Enteritis emerging as a serious threat to animal and public health.

Clostridium perfringens, is a gram positive, anaerobic bacteria found in soil, dust, faeces, feed, poultry litter and intestinal contents. It is extremely prolific and is able to produce various toxins and enzymes. Clostridium perfringens strains are classified into five toxinotypes (A, B, C, D and E), based on the production of four toxins (a, B, & and 1). It has been proposed that Necrotic Enteritis is caused by type A and to a lesser extent type C, with type A strains producing chromosomal-encoded alpha toxin, while type C strains produce alpha toxins along with beta toxins.

Alpha toxin is a phospholipase C sphingomyelinase that hydrolyzes phospholipids and promotes membrane disorganization, inducing synthesis of mediators such as leukotrienes, thromboxane, platelet-agglutinating factor and prostacyclin. These mediators cause blood vessel contraction, platelet aggregation and myocardial dysfunction, leading to acute death. The beta toxin induces hemorrhagic necrosis of the intestinal mucosa although the exact mechanism is not yet known. The pathology of Necrotic Enteritis is being re-evaluated along with a search for other virulence factors. Recently, there has been evidence suggesting that alpha toxin may not have the major role in the pathogenesis of Necrotic Enteritis that has been proposed, with studies reporting an impaired ability to cause the disease using non wild-type alpha toxin. The evidence suggests that the molecules in Clostridium perfringens culture supernatant, when infused into the gut, reproduced disease-like pathology. Recent evidence also suggests that the NetB toxin from Clostridium perfringens may play a key role in Necrotic Enteritis pathogenesis.

Clostridium perfringens is found naturally at low levels in the gut, but disturbances to normal intestinal microflora may cause rapid proliferation of the bacteria, resulting in the development of Necrotic Enteritis. Chickens are most commonly affected at 2 to 6 weeks old, however Necrotic Enteritis may occur in birds 7 to 16 weeks old or even up to 6 months.

The disease is characterized clinically by a sudden increase in flock mortality, often without premonitory signs, although wet litter is sometimes an early indicator. Clinical signs can include depression, dehydration, somnolence, ruffled feathers, diarrhoea and decreased feed consumption though clinical illness before death is of short duration so reduction of body weight gain is not apparent. Macroscopical lesions can be found in the small intestine; the duodenum, jejunum and ileum become thin-walled, friable, dilated and filled with gas. In addition, mucosal surfaces are covered with a grey-brown to yellow-green diphteric membrane or pseudomembrane. Lesions may also be found in other organs, as well as atrophy of erythrocytes and bursa. The subclinical form of Necrotic Enteritis is considerably less recognizable and sick birds that respond to treatment with an antibiotic analogue are often deemed to have had the disease. Wet litter generally precipitates immediate antibiotic therapy in poultry farms despite wet litter not always clostridial in origin. In addition, mild necrosis of the intestinal mucosa was reported in subclinical Necrotic Enteritis. Example 1 describes the use of berberine sulfate (IRP001 sulfate) in the prevention or treatment of Necrotic Enteritis.

Example 1

A pilot study to determine the dose response, efficacy, and safety of IRP001 sulfate when administered prophylactically (orally via feed) and therapeutically (orally via drinking water) to specific pathogen free chickens artificially challenged with Clostridium Perfringens utilizing proven experimental models.

Materials and Methods

Study Design (Necrotic Enteritis challenge)—Commercial broiler chickens housed in isolators, were infected orally at 9 days of age with 5,000 attenuated vaccine strain sporulated oocysts each of E. maxima and E. acervuline and 2,500 sporulated oocysts of E. brunetti in 1 mL of 1% (w/v) sterile saline.

Five and six days following oocyst challenge (Days 14 and 15), a known pathogenic strain of Clostridium Perfringens was administered (type A strain EHE-NE36, CSIRO Livestock Industries, Geelong, Australia), i.t. (~8.0 log 10 cfu/chicken). All NE cohort birds sacrificed and autopsied at Day 16. NE lesion scores and mortality at autopsy are used as outcome parameters and are shown in Table 22 and Table 23 below. Feed and water intake and weight gain are also measured.

Investigational Veterinary Product (IVP)—IRP001 Berberine Hemisulfate Salt (IRP001 Sulfate)

TABLE 20

Challenge and Treatment Regime

| Grp. | Bird type | Challenge details | Treatment | IRP001 sulfate conc. | Route | Trt. Days | No. Animals |
|---|---|---|---|---|---|---|---|
| 1 | Broiler | Nil | Nil | — | — | — | 15 |
| 2 | Broiler | Nil | Nil | — | — | — | 15 |
| 3 | Broiler | Nil | IVP | 1.0 g/L | In-water | 1-16 | 15 |
| 4 | Broiler | Nil | IVP | 1.0 g/L | In-water | 1-16 | 15 |
| 5 | Broiler | NE | Nil | — | — | 1-16 | 15 |
| 6 | Broiler | NE | Nil | — | — | 1-16 | 15 |
| 7 | Broiler | NE | IVP | 0.1 g/L | In-water | 1-16 | 15 |
| 8 | Broiler | NE | IVP | 0.1 g/L | In-water | 1-16 | 15 |
| 9 | Broiler | NE | IVP | 1.0 g/L | In-water | 1-16 | 15 |
| 10 | Broiler | NE | IVP | 1.0 g/L | In-water | 1-16 | 15 |
| 11 | Broiler | NE | IVP | 0.1 g/kg | In-water | 1-16 | 15 |
| 12 | Broiler | NE | IVP | 1.0 g/kg | In-water | 1-16 | 15 |

TABLE 21

Schedule of Events

| Approx. Study Day | Event |
|---|---|
| Pre-study | Receipt of formulation. Receipt of Animal Ethics Committee approval |
| 0 | Broiler chicks hatched. Chicks transported and placed into positive pressure isolators |
| 9 | NE challenge (Groups 5-12) chicks inoculated with mixed *Eimeria* spp. orally |
| 14 | NE challenge (Groups 5-12) chicks challenged with CP orally |
| 15 | Groups 1-12 chicks euthanized for NE lesion scoring. Selected tissues collected for histological examination and residue analysis |

Results

TABLE 22

Summary data for median lesion scores

| Group | 1, 2 | 3, 4 | 5, 6 | 7, 8 | 9, 10 | 11 | 12 |
|---|---|---|---|---|---|---|---|
| Bird type | Broiler | Broiler | Broiler | Broiler | Broiler | Broiler | Broiler |
| Challenge Details | Nil | Nil | NE | NE | NE | NE | NE |
| Trt, | Nil | IVP | Nil | IVP | IVP | IVP | IVP |
| IVP conc. | — | 1.0 g/L | — | 0.1 g/L | 1.0 g/L | 0.2 g/kg | 2.0 g/kg |
| Route | — | In-water | — | In-water | In-water | In-feed | In-feed |
| No. Days Trt. | — | 16 | — | 16 | 16 | 16 | 16 |
| No. Birds | 30 | 30 | 30 | 30 | 30 | 15 | 15 |
| No. birds Autopsied | 29 | 24 | 30 | 28 | 24 | 11 | 15 |
| Median Lesion Scores | | | | | | | |
| Duodenal Lesion Score (0 absent to 4 severe) | 0 | 0 | 4 | 4 | 1 | 4 | 1 |
| Jejunal Lesion Score (0 absent to 4 severe) | 0 | 0 | 4 | 4 | 1 | 4 | 1 |
| Ilial Lesion Score (0 absent to 4 severe) | 0 | 0 | 4 | 4 | 1 | 4 | 1 |

TABLE 23

Broiler mortalities prior to autopsy

| Group | Treatment/Challenge | Isolator | Mortalities | No. Birds | Mortality % |
|---|---|---|---|---|---|
| 1 | 13, 14 Nil Challenge, | 15 | 0 | 14 | 0% |
| 2 | Nil IVP | 12 | 0 | 15 | 0% |
|  | Mean |  | 0 | 29 | 0% |
| 3 | 15, 16 Nil Challenge, | 10 | 0 | 10 | 0% |
| 4 | IVP water 1.0 g/L | 4 | 0 | 15 | 0% |
|  | Mean |  | 0 | 25 | 0% |
| 5 | 17, 18 Necrotic Enteritis, | 1 | 15 | 15 | 100% |
| 6 | Nil IVP | 7 | 10 | 15 | 67% |
|  | Mean |  | 25 | 30 | 83% |
| 7 | 19, 20 Necrotic Enteritis, | 6 | 12 | 13 | 92% |
| 8 | IVP water 0.1 g/L | 11 | 10 | 15 | 67% |
|  | Mean |  | 22 | 28 | 79% |
| 9 | 21, 22 Necrotic Enteritis, | 2 | 0 | 9 | 0% |
| 10 | IVP water 1.0 g/L | 8 | 0 | 16 | 0% |
|  | Mean |  | 0 | 25 | 0% |
| 11 | 23 Necrotic Enteritis, IVP feed 0.2 g/kg | 9 | 9 | 11 | 82% |
| 12 | 24 Necrotic Enteritis, IVP feed 2 g/kg | 3 | 2 | 15 | 13% |

Figure 5:
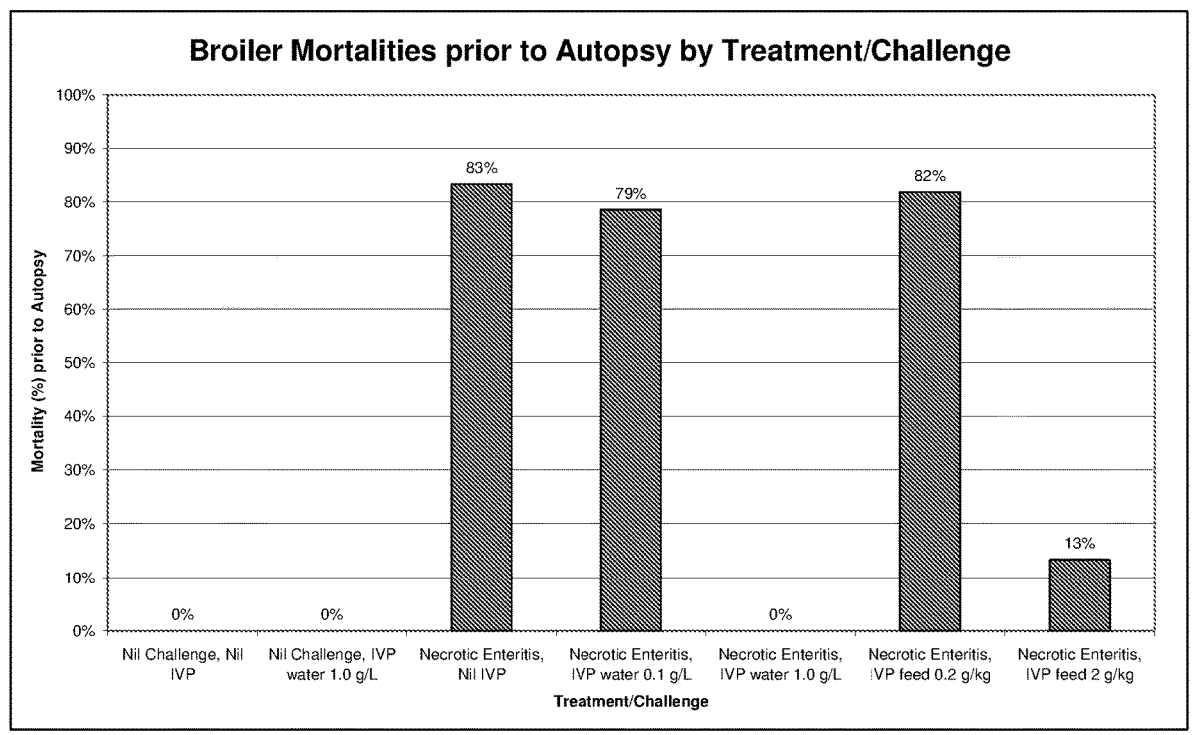
FIG. 5 to FIG. 12 depict the results of the Necrotic Enteritis pilot study in chickens described in Example 1.
Figure 6:
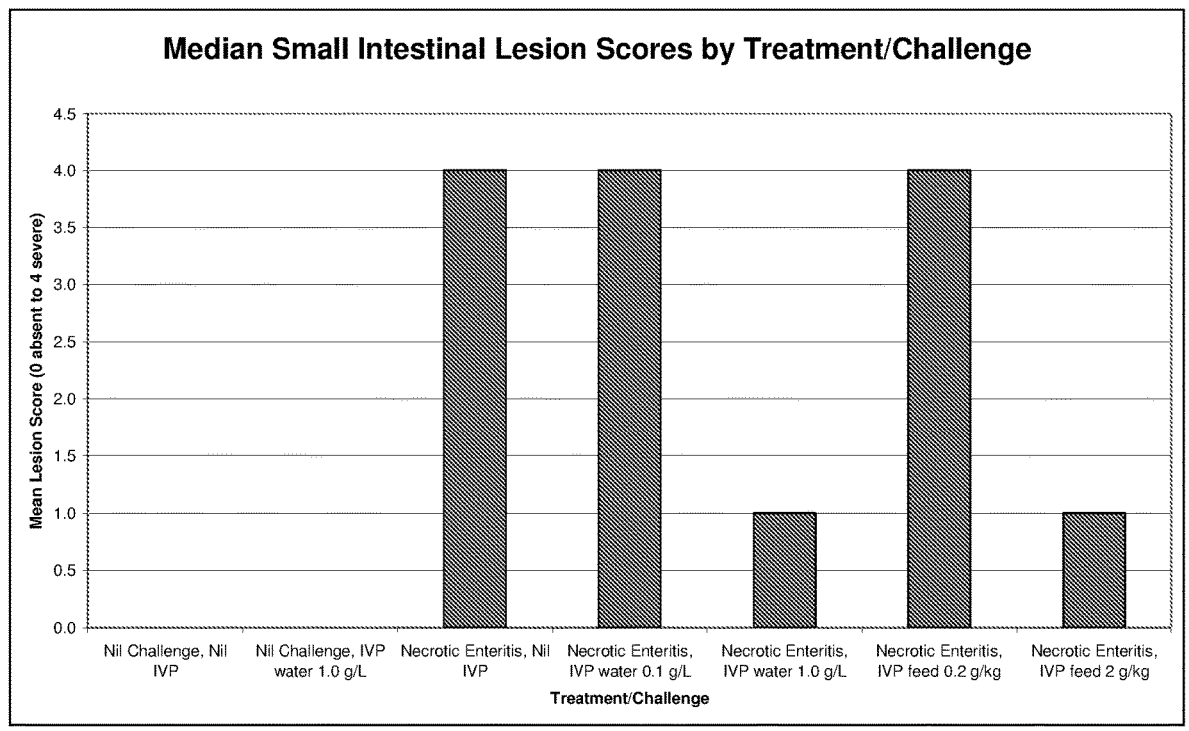
Figure 7:
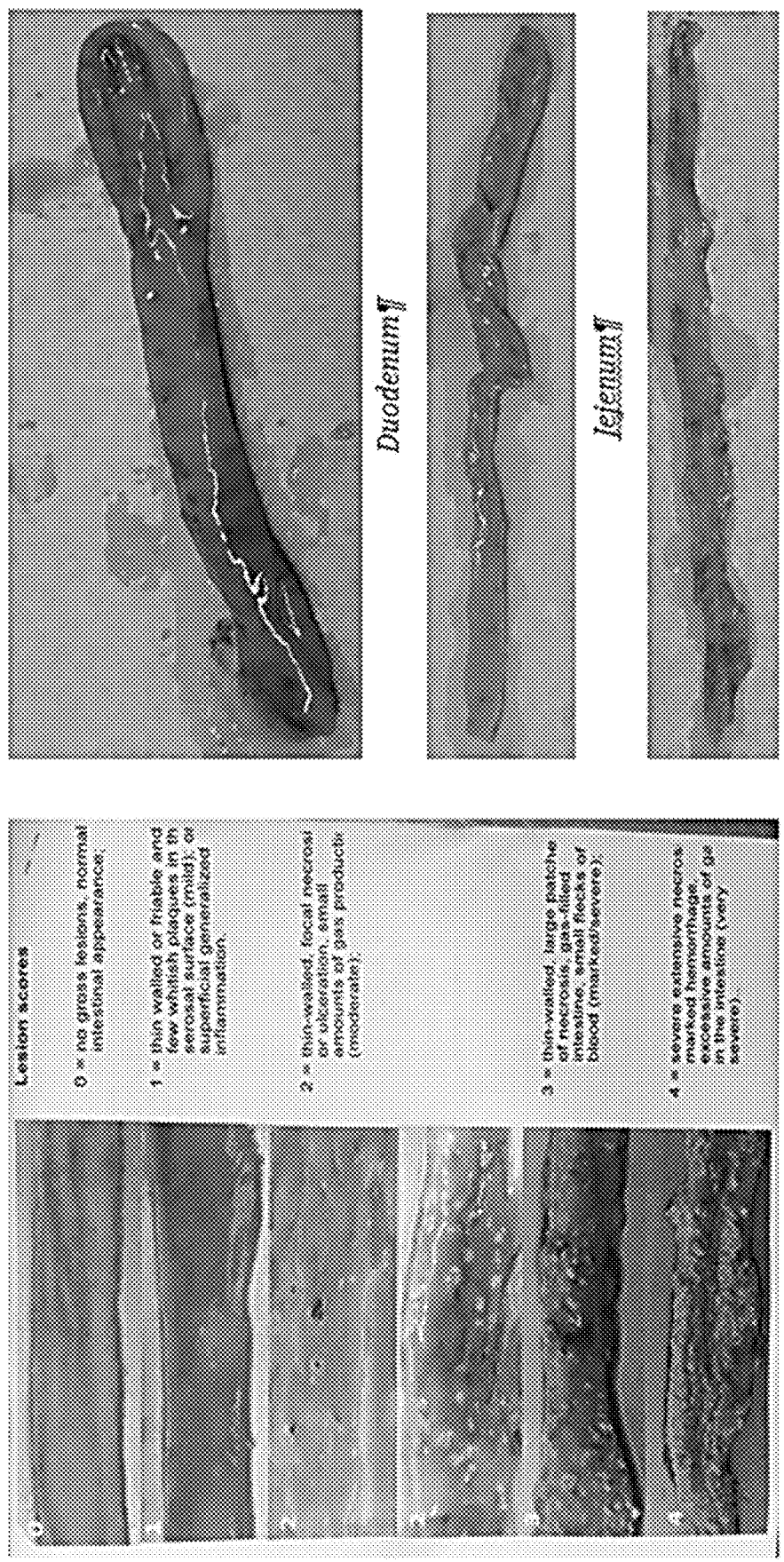
Figure 8:
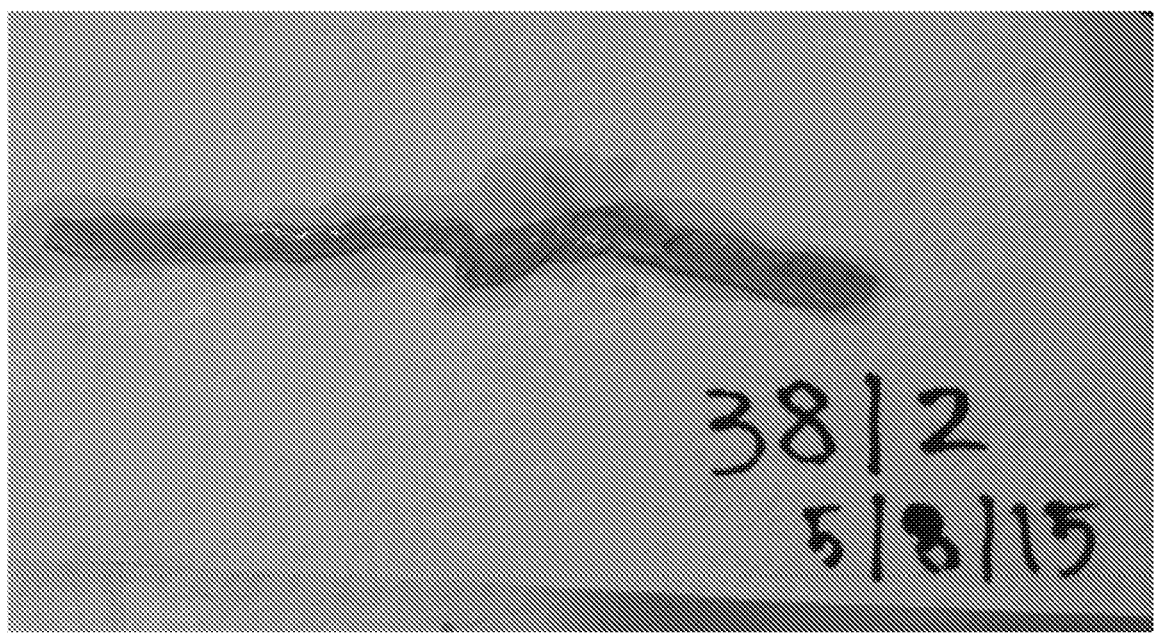
Figure 9:
Figure 10:
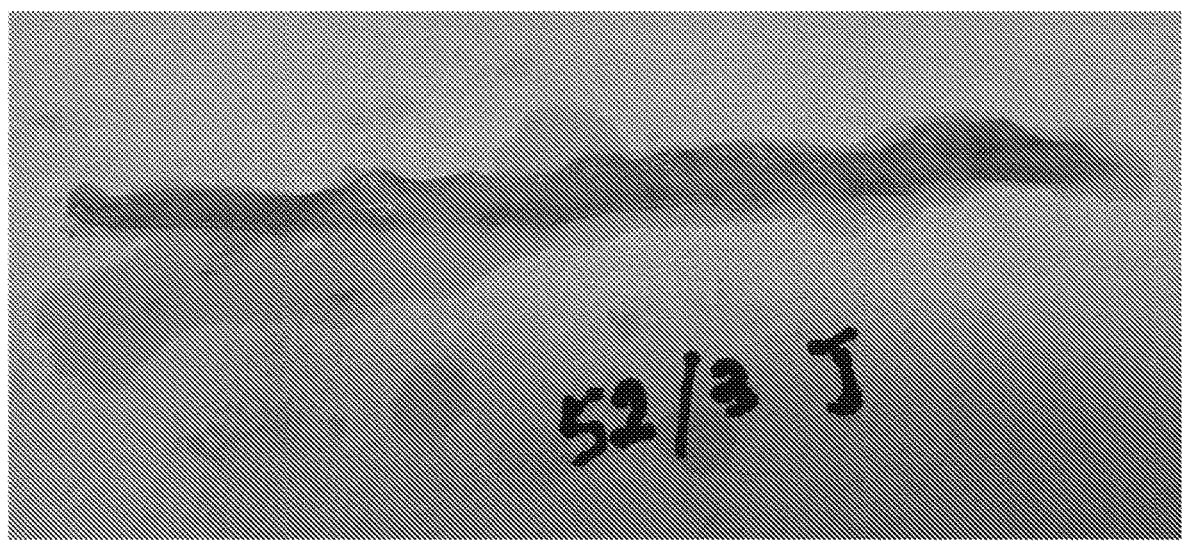
Figure 11:
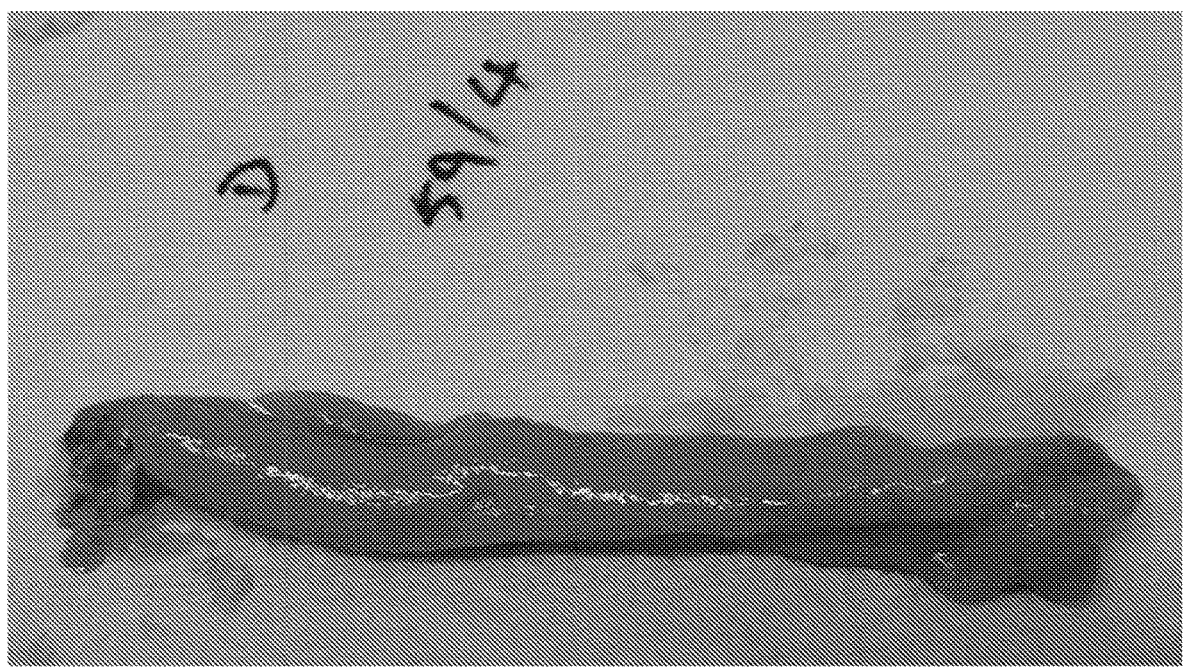
Figure 12:
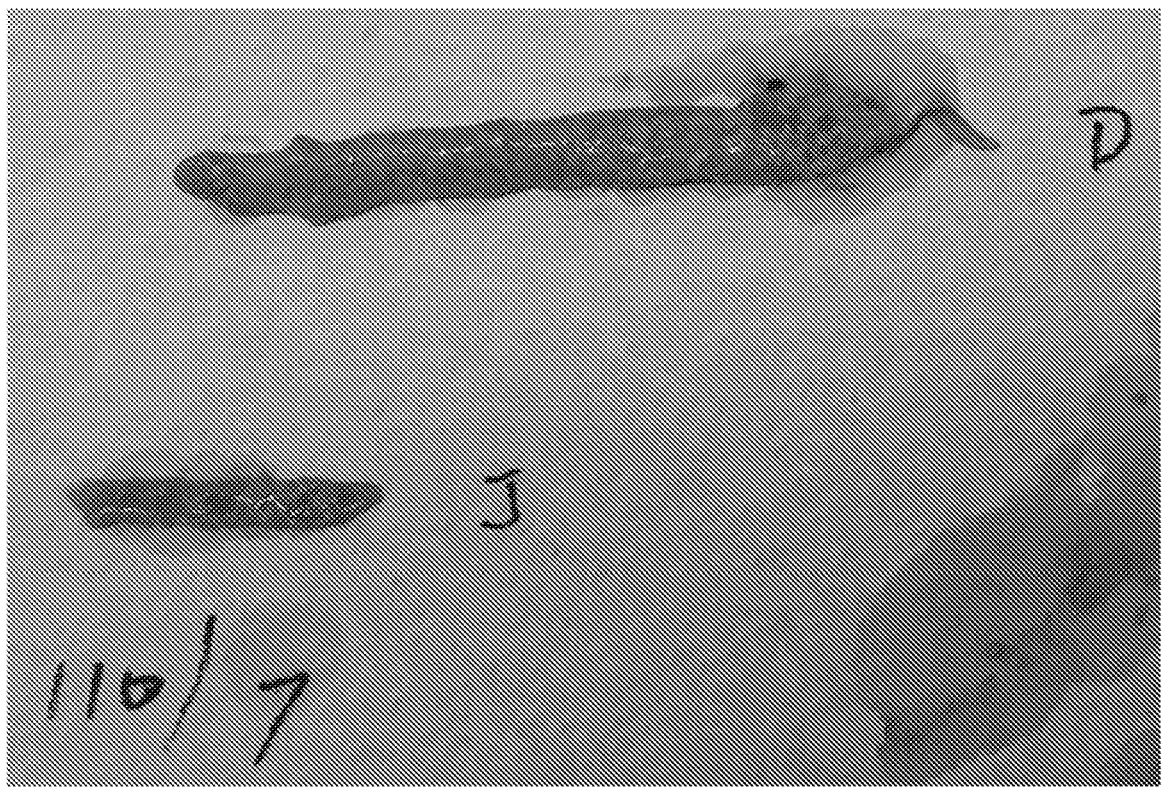

Inclusion of IRP001 sulfate at either 1.0 g/L in-water or 2.0 g/kg in-feed resulted in a significant reduction in mortalities in the NE challenged broilers, relative to both the nil-treatment groups and the groups treated with either 0.1 g/L in-water or 0.2 g/kg in-feed (See FIG. 5). Mortalities in the nil-treatment, 0.1 g/L water and 0.2 g/kg in-feed groups were not significantly different in the NE challenged broilers.

Morbidity was also reduced. Inclusion of IRP001 sulfate at either 1.0 g/L in-water or 2.0 g/kg in-feed resulted in a substantial reduction in small intestinal lesion scores, relative to the nil treatment groups, in broilers challenged with NE (See FIGS. 6 to 12). Conversely, inclusion of IRP001 at either 0.1 g/L in-water or 0.2 g/kg in-feed resulted in no reduction in median lesion scores relative to nil-treatment in the NE challenged broilers.

Example 2

A follow-up study to determine the feed palatability, feed and water consumption and bird productivity following incorporation of a single formulation of IRP001 hemisulfate salt (unmasked) when offered to broiler chickens in-feed or in-water. The study explores the optimal treatment regime in terms of treatment start date.

Materials and Methods

Study Design

Phase 1: On receipt, two hundred and seventy (270) day-old commercial broiler chickens were allocated sequentially as they are received into sixteen (16) individual floor pens, each of 16 or 17 birds, on Day 0.

Phase 2: On receipt, the ninety (90) day-old commercial broiler chickens were allocated sequentially as they are received into four (4) individual floor pens, each of 22 or 23 birds, on Day 22.

Feed intake, water intake, weight gain and mortality were used as outcome parameters.

Investigational Veterinary Products (IVP)

TABLE 24

IVP for Example 2

| Name | Composition | Dose Level |
|---|---|---|
| IRP001 Sulfate | 100% IRP001 sulfate | 1.0 g per L in water 2.0 g per kg of feed |

TABLE 25

Phase 1 - Day-old chicks received day 0

| Group | Formulation | IVP conc. in-feed (g/kg) | IVP conc. In-water (g/L) | Trt. Days | Sacrifice Day |
|---|---|---|---|---|---|
| 1 | Nil | — | — | — | 42 |
| 2 | Nil | — | — | — | 42 |
| 3 | IVP | — | 1 | 0-21 | 21 |
| 4 | IVP | — | 1 | 0-21 | 21 |
| 5 | IVP | — | 1 | 1-21 | 21 |
| 6 | IVP | — | 1 | 1-21 | 21 |
| 7 | IVP | — | 1 | 2-21 | 21 |
| 8 | IVP | — | 1 | 2-21 | 21 |
| 9 | IVP | — | 1 | 3-21 | 21 |
| 10 | IVP | — | 1 | 3-21 | 21 |
| 11 | IVP | — | 1 | 4-21 | 21 |
| 12 | IVP | — | 1 | 4-21 | 21 |
| 13 | IVP | — | 1 | 5-21 | 21 |
| 14 | IVP | — | 1 | 5-21 | 21 |
| 15 | IVP | — | 1 | 6-21 | 42 |
| 16 | IVP | — | 1 | 6-21 | 42 |

TABLE 26

Phase 2 - Day-old chicks received day 22

| Group | Formulation | IVP conc. in-feed (g/kg) | IVP conc. In-water (g/L) | Trt. Days | Sacrifice Day |
|---|---|---|---|---|---|
| 17 | Nil | — | — | — | 42 |
| 18 | Nil | — | — | — | 42 |
| 19 | IVP | 2 | — | 25-42 | 42 |
| 20 | IVP | 2 | — | 25-42 | 42 |

TABLE 27

Schedule of Events

| Approx. Study Day | Event |
|---|---|
| Pre-study | Receipt of formulation. Receipt of Animal Ethics Committee approval |
| 0 | Commence Phase 1. 270 Broiler chicks hatched. Broiler chickens transported and placed into floor pens. Commence twice daily health monitoring, water and feed records. Weigh all chickens on group pen basis. Allocate to treatment groups and pens. Commence medicated water Groups 3 and 4. |
| 1-41 | Continue twice daily health monitoring, water and feed records. |
| 1 | Commence medicated water Groups 5 and 6. |
| 2 | Commence medicated water Groups 7 and 8. |
| 3 | Commence medicated water Groups 9 and 10. |
| 4 | Commence medicated water Groups 11 and 12. |
| 5 | Commence medicated water Groups 13 and 14. |
| 6 | Commence medicated water Groups 15 and 16. |
| 7, 14, 21, 28 & 35 | Weigh all chickens |
| 21 | Sacrifice Groups 3 to 14 inclusive, note gross pathology changes. Collect range of tissue samples from 4 selected birds in each of Groups 4 and 14. Store frozen. |
| 22 | Commence Phase 2. 90 Broiler chicks hatched. Broiler chicks transported and placed into floor pens. Commence twice daily health monitoring, water and feed records. Allocate to treatment groups and pens. |
| 25 | Commence medicated feed Groups 19 and 20. |
| 42 | Sacrifice Groups 1, 2, 15, 16, 17, 18, 19 and 20 animals. Note gross pathology changes (Closely monitor and compare muscle colour of each chicken particularly looking for any colouration associated with prolonged IRP001 treatment.) Retain frozen selected muscle tissue representative of colouration if present. Collect range of tissue samples from 4 selected birds in Groups 16 and 20. |

Results

Individual daily feed intake and individual daily water intake data by pen and then by treatment group were calculated for Phases 1 and 2 (and for the entire trial for the birds in Group/Pen 2, 15 and 16 that continue through both Phases) using figures for total feed and water provided each day to each pen divided by the number of birds in each pen. Where errors in weighing, feeding/watering or recording (or other unexplained losses of feed and water) had occurred means were adjusted by using the mean value for the same pen on the 1-2 days either side of the apparent error. Similarly, group mean bodyweights were calculated for Phase 1 using total weight/total no. birds for Day 0 and individual weights from Days 7, 14, 21, 28, 35 and 42. Total (individual) feed consumed was calculated per treatment and feed conversion ratios per treatment calculated using the expression: total (individual) feed/total (individual) weight gain.

Individual daily feed intake and individual daily water intake were statistically compared by treatment within each phase and between Pens 2 and 15/16 over both phases using a linear model:—

(Parameter)~Treatment+Day+Pen+Treatment:Day and Tibco SPOTFIRE S+ 8.2 (2010). 'Day' was included in the model to allow for changes over time, 'Pen' as each treatment consisted of 2 pens while an interaction term 'Treatment:Day' was included to allow for treatment x time effects. Model suitability was confirmed by inspection of residual plots; in all instances the statistical model was appropriate.

Phase 1:

TABLE 28

Phase 1 summary data

| Group-Pen | Treatment | 0 | Day 7 | 14 | 22 | Gain (kg) | Total Feed (kg) | FCR |
|---|---|---|---|---|---|---|---|---|
| 1, 2 | Untreated P1 | 42.3 | 131.8 | 303.9 | 747.4 | 0.705 | 1.089 | 1.54 |
| 3, 4 | Day 0-21 | 43.2 | 118.1 | 291.9 | 653.6 | 0.610 | 0.908 | 1.49 |
| 5, 6 | Day 1-21 | 42.4 | 125.8 | 309.0 | 720.7 | 0.678 | 1.019 | 1.50 |
| 7, 8 | Day 2-21 | 44.6 | 132.0 | 315.4 | 719.4 | 0.675 | 0.977 | 1.45 |
| 9, 10 | Day 3-21 | 42.4 | 118.6 | 295.1 | 695.7 | 0.653 | 0.939 | 1.44 |
| 11, 12 | Day 4-21 | 41.8 | 138.8 | 320.3 | 758.2 | 0.716 | 1.046 | 1.46 |
| 13, 14 | Day 5-21 | 44.3 | 135.3 | 316.8 | 724.7 | 0.680 | 1.010 | 1.48 |
| 15, 16 | Day 6-21 (42) | 43.8 | 139.1 | 325.2 | 767.2 | 0.723 | 1.016 | 1.40 |

Feed intake: 'Treatment' was significant, 'Day' was highly significant, 'Pen' was not significant. However, no significant differences (at p<0.05) were observed on individual pair-wise comparisons of treatments.

Water intake: 'Treatment' was significant, 'Day' was highly significant. A number of pairwise comparisons of treatment were significant, however results were not conclusive. A moderate trend did appear to exist such that groups receiving the test treatment (which was unmasked in the drinking water) for longer periods drank less water than groups treated for shorter periods and the untreated control groups (See FIG. 13).

Bodyweight: 'Treatment' was significant, 'Day' was highly significant, 'Pen' was not significant. However, no significant differences (at $p<0.05$) were observed on individual pair-wise comparisons of treatments.

Within Phase 1, unmasked treatment via drinking water over varying periods therefore did not appear to affect either feed intake or bodyweight, although treated birds tended to drink less water.

Phase 2:

TABLE 29

Phase 2 summary data

| Group-Pen | Treatment | Day (kg) 28 | 35 | 42 | Gain (kg) | Feed (kg) | FCR |
|---|---|---|---|---|---|---|---|
| 2 | Untreated P1 | 1.05 | 1.55 | 2.18 | 2.137 | 4.169 | 1.95 |
| 15, 16 | D6-21 (42) | 1.16 | 1.66 | 2.39 | 2.346 | 3.841 | 1.64 |
|  |  |  | (g) |  |  | (kg) |  |
| 17, 18 | Untreated P2 | 113.4 | 277.6 | 628.0 | 0.515 | 0.805 | 1.56 |
| 19, 20 | Day 25-42FEED | 112.4 | 273.6 | 614.9 | 0.502 | 0.783 | 1.56 |

Feed intake: 'Treatment and 'Pen' were not significant although 'Day was highly significant. However, no significant differences (at $p<0.05$) were observed on pair-wise comparison of the 2 treatments.

Figure 14:
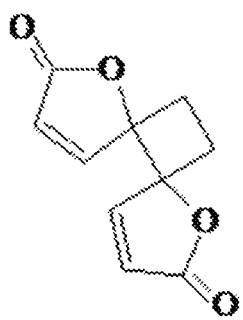
FIG. 14 depicts the molecular structures and names of further representative compounds of the invention.
Figure 14:
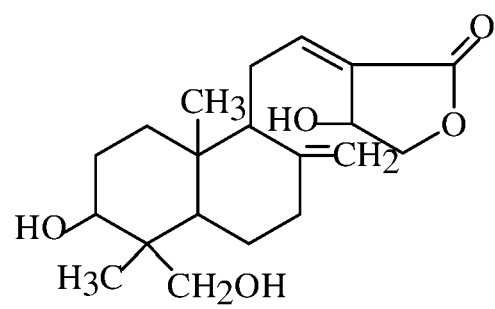
Figure 14:
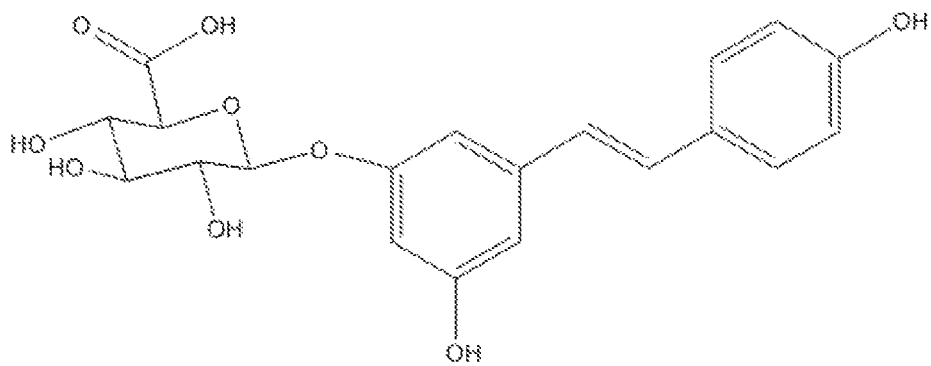

Water intake: 'Treatment was highly significant, "Day was highly significant. A significant difference was observed on pair-wise comparison of the 2 treatments, with treated birds (who received treatment in-feed) drinking more water (see FIG. 14).

Bodyweight: "Treatment' and 'Pen' were not significant (although as expected 'Day' was). No significant differences (at $p<0.05$) were observed on pair-wise comparisons of the 2 treatments.

Within Phase 2 treatments (in-feed) did not appear to affect either feed intake or bodyweight, while treated birds tended to drink more water (in contrast to Phase 1 where they tended to drink less water when the unmasked treatment was applied in the drinking water).

Phase 1+2 (Group-Pen 2 Untreated Vs 15/16, Treated In-Water Day 6-42):

Feed intake: While 'Treatment' was not significant in the overall model (and 'Day' was highly significant) there was a significant difference (at $p<0.05$) on pair-wise comparison of the 2treatments, with untreated birds eating ~0.14 kg more feed over the total trial than untreated birds.

Water intake: 'Treatment was highly significant, 'Day 'was highly significant. A significant difference (at $p<0.05$) was observed on pair-wise comparison of the 2 treatments, with untreated birds drinking more water over the total trial than untreated birds.

Bodyweight: While 'Treatment was significant in the model (and, as expected 'Day 'was highly significant) no significant difference (at $p<0.05$) was observed on pair-wise comparisons of the 2 treatments.

Figure 15:
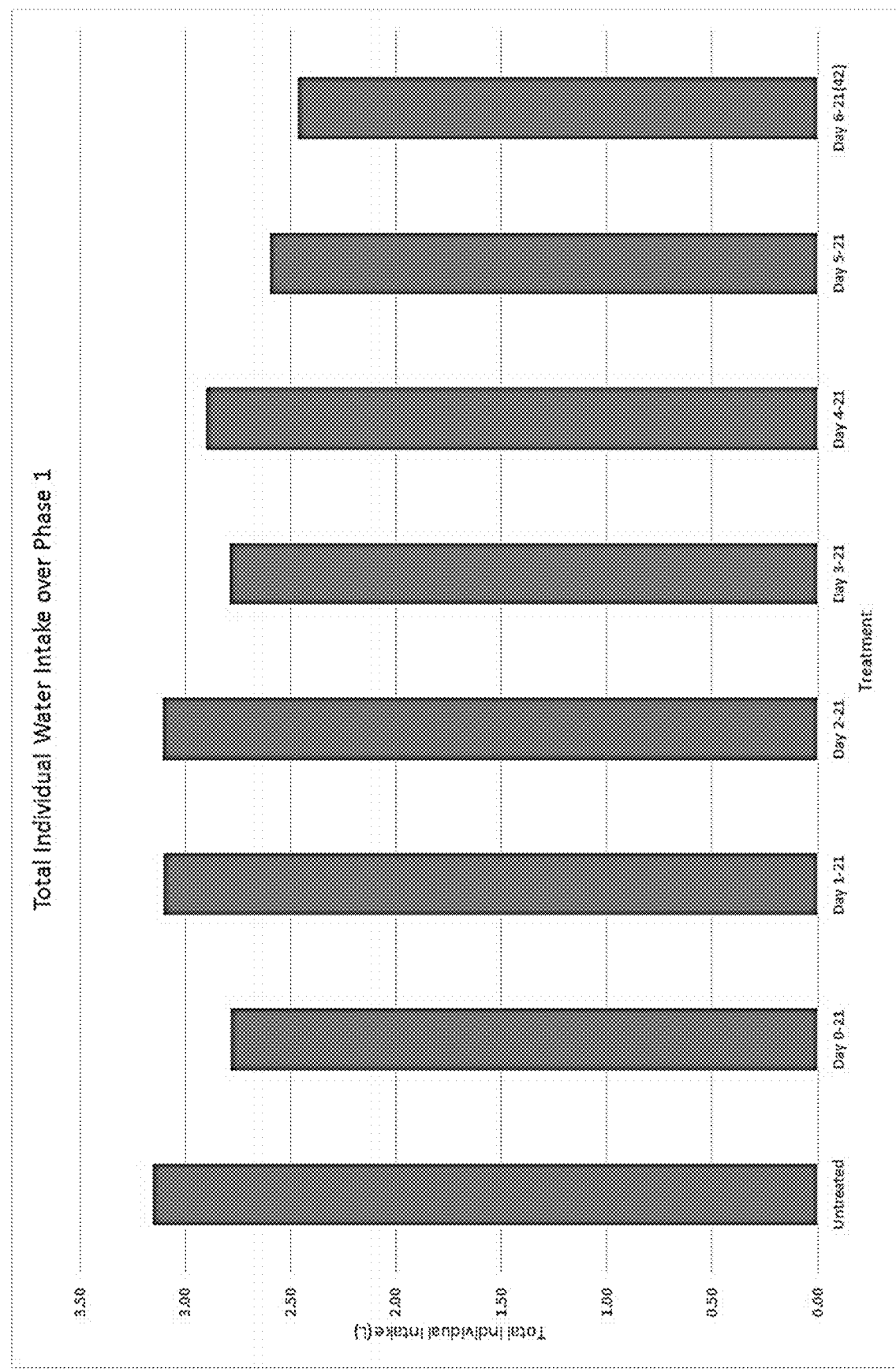
FIG. 15 depicts total individual water intake (Phase 1) for the Necrotic Enteritis pilot study described in Example 2.
Figure 16:
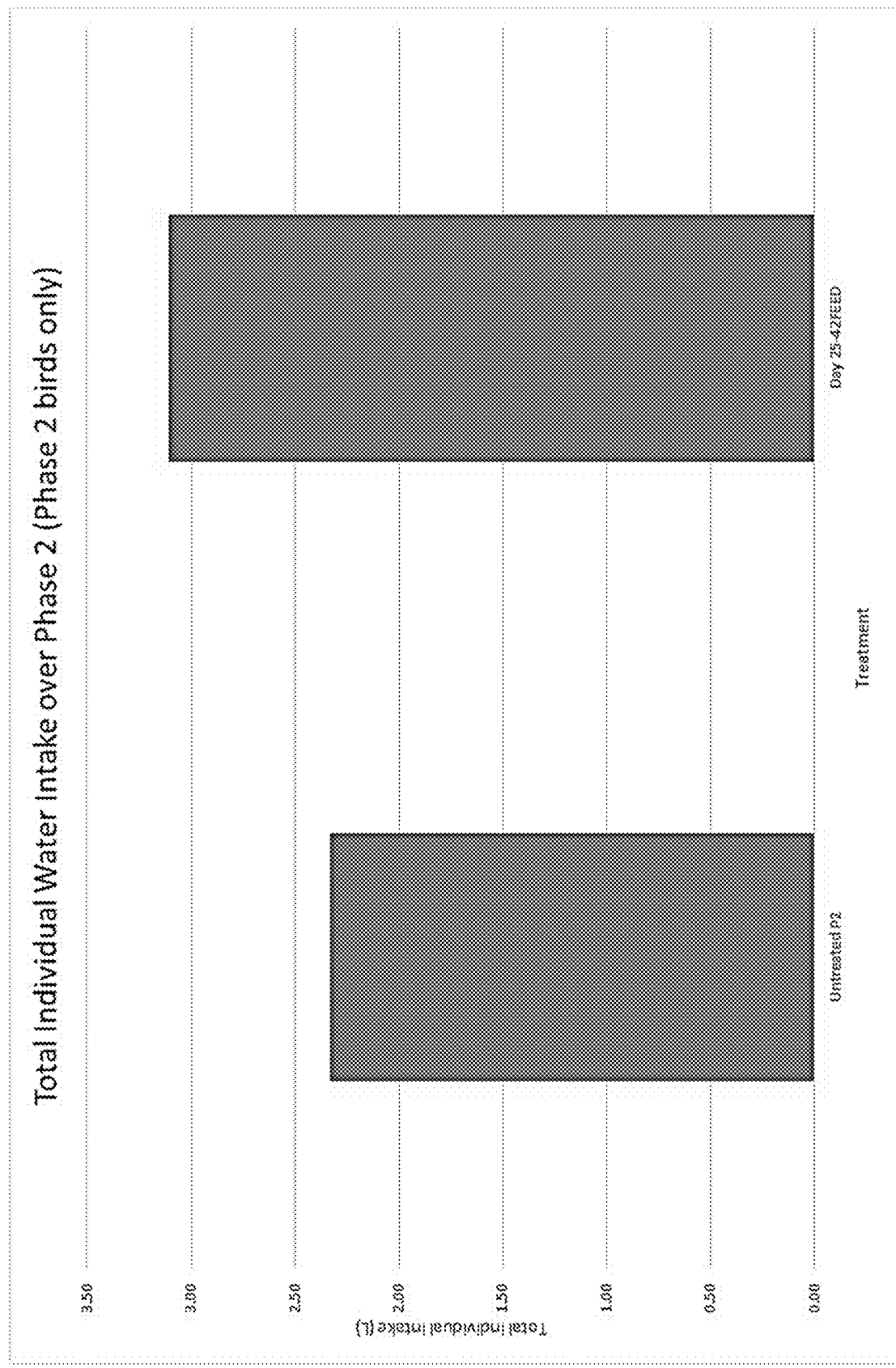
FIG. 16 depicts total individual water intake (Phase 2) for the Necrotic Enteritis pilot study described in Example 2.
Figure 17:
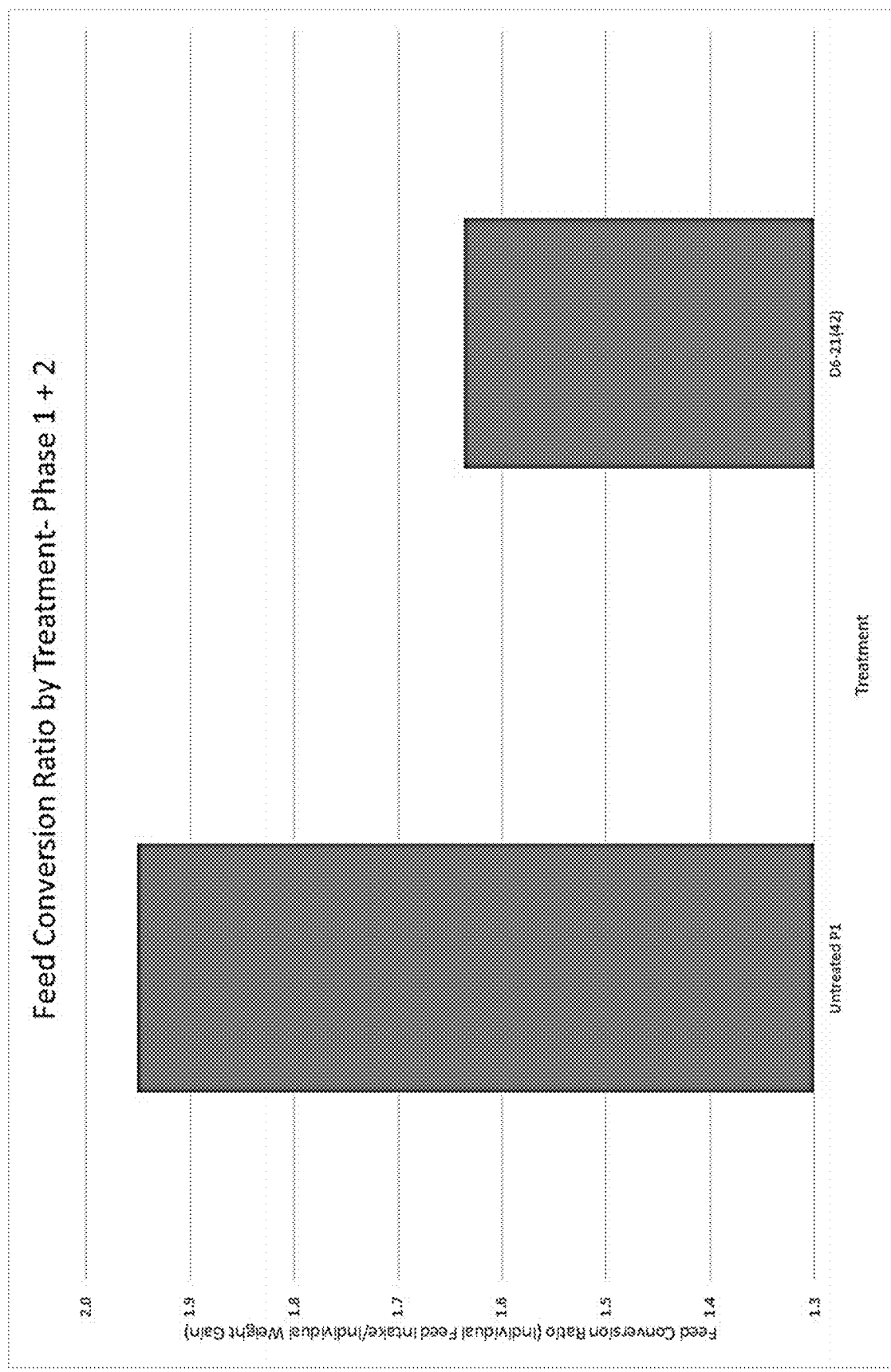
FIG. 17 depicts feed conversion ratio (Phase 1 and 2) for the Necrotic Enteritis pilot study described in Example 2.

When the combination of significantly higher feed intake and similar (non-significantly different) bodyweights were both take into account via feed conversation ratios, there appeared to be moderate advantages to treatment over Days 6-42 relative to no treatment (See FIG. 15). Treated birds consumed 3.84 kg of feed and gained 2.35 kg (FCR of 1.6 kg feed: 1 kg gain) while untreated birds consumed 4.17 kg of feed and gained 2.14 kg (FCR of 1.95 kg feed: 1 kg gain).

Example 3

To evaluate the efficacy of three dose rates of the IVP, berberine chloride, in feed against a mixed moderate coccidiosis challenge in commercial meat chickens and to assess any occurrence of Necrotic Enteritis or non-specific enteritis. The study provides a scoping project on the most likely effective dose rate of the IVP for broiler chickens and evaluate the likely success in control of coccidiosis and subsequent necrotic enteritis compared with an industry standard.

Materials and Methods

Field samples of coccidial oocysts (*Eimeria* species from broiler and layer chicken sources) were obtained, transported to a laboratory where they were filtered, sporulated, sanitized and stored. The *Eimeria* species present were identified by PCR and oocysts counted. These were propagated through naïve chicks to produce a number sufficient for the challenge inoculum for the seeder birds. Thirty 1-day-old meat chickens were obtained from a commercial hatchery and placed in battery brooder cages at the trial facility, 10 chicks per cage. These were fed an unmedicated ration and sporulated oocysts were administered by gavage at day 7. At day 13, birds were euthanized and their intestinal tracts removed. Upper and lower small intestine and caeca were separated and placed into 2% potassium dichromate, left for 3-5 days at 4° C. and then scraped to remove the mucosa. This was passed through a coarse sieve into fresh potassium dichromate solution. The oocysts therein were sporulated, examined under a microscope and counted and the species identified by PCR.

Figure 18:
FIG. 18 depicts the pen set up with day old chicks for the study described in Example 3.

One thousand, one hundred and eighty (1180) 1-day-old Ross 308 chickens were obtained from a commercial hatchery, vaccinated against Infectious Bronchitis and Newcastle Disease at the hatchery. The chicks were transported to the trial facility and randomized into each of 30 floor pens, placed at 36 chicks per pen (FIG. 18). Pens were reduced to half normal size by a divider providing 3.5 m² floor space per pen. This was intended to provide a final bird density of approximately 30 kg/m². A further two full size pens had 50 birds placed per pen (these acted as seeders for the coccidiosis challenge).

Feeds were based on a suitable, balanced basal ration formulation (Starter, Grower and Finisher). Products were added to each of the basal rations as follows (Table 30).

TABLE 30

Treatment groups/feeds

| Treatment No. | Inclusion |
|---|---|
| 1 | Basal rations only - negative control |
| 2 | IVP 0.3 g/kg |
| 3 | IVP 0.1 g/kg |
| 4 | IVP 0.03 g/kg |
| 5 | Salinomycin 60 ppm |
| 6 | Salinomycin 60 ppm plus zinc bacitracin 50 ppm |

Pens were allocated a feed on a randomized complete block basis. Feeds were provided to each pen at 0.7 kg per bird Starter (approximately days 0-14), 1.2 kg per bird Grower (approximately days 15-28) and Finisher feed thereafter until termination (day 42). Seeder bird pens received ration #1 (unmedicated).

Figure 19:
FIG. 19 depicts the litter collected from seeder pens at day 14 of the study described in Example 3.
Figure 20:
FIG. 20 depicts the 400 grams of litter allocated per pen at day 14 of the study described in Example 3.

On day 6, the birds in the seeder pens were given the oocyst inoculum by individual gavage (approximately 0.5 mL per bird) using a stepper pipette. Three separate samples of sporulated oocysts from various chicken farm sources were used-given to approximately one third of the birds in each seeder pen. The litter in the seeder pens was lightly raked on days 12, 13 and 14. On day 14 the top 2-3 cm of the litter in the seeder pens was collected and mixed well together and weighed (FIG. 19). The total weight of the litter was divided by 30 and that amount of litter distributed into each of the trial pens (each pen received 400 gm of mixed seeded litter—FIG. 20).

Four subsamples of the mixed litter will be collected and oocysts counts were performed by suspending 7 gm of litter in 75 mL of saturated sucrose and counting the total number of oocysts visible in a Whitlock Universal counting chamber under 100× magnification.

Birds were weighed on a pen basis on days 0, 14, 21, 28 and 42. Feed consumption was measured on days 14, 21, 28 and 42. Feed conversion ratios (FCR) were calculated over each time period and corrected for bird loss and removal.

Any bird which died or was culled was recorded and weighed and examined at necropsy, paying particular attention to the intestinal tract for lesions consistent with coccidiosis or enteritis. Sex was recorded.

On day 21, four birds were randomly selected from each trial pen, humanely euthanized and their intestines and caeca scored for coccidiosis lesions in four gut segments (upper, mid and lower intestine and caeca) and lesions typical of *Eimeria* species noted. General gut quality (looking for enteritis) was also visually assessed at that point.

Four individual faecal samples per pen were collected and pooled on day 21 and evaluated for oocyst count.

At day 42, all surviving birds were euthanized and their carcasses disposed of by contaminated waste collection (not to go for slaughter for human consumption).

Results

Table 31 shows the identity of *Eimeria* species included in the inoclula given to the seeder birds, as determined by PCR at Birling Avian laboratories. This PCR is qualitative only but relative abundance of each species can be estimated (shown with increasing numbers of "+" signs if more abundant).

TABLE 31

Eimeria species detected in challenge inocula for seeder birds

| Sample origin | Oocysts/ mL | E. tenella | E. necatrix | E. maxima | E. acervulina | E. brunetti | E. praecox | E. mitis |
|---|---|---|---|---|---|---|---|---|
| Layers | 7,500 | + | + | ++ | + | ++ | ND | ND |
| Broilers | 12,000 | ++ | ++ | ++ | ++ | ND | ND | ND |
| Broilers | 12,000 | + | ++ | ++ | ++ | ++ | ND | ND |

+, ++ indication of relative amount present;

ND = not deleted

Table 32 outlines the counts of oocysts per gram of mixed litter samples (samples counted in quadruplicate) derived from the seeder pens 7 days post inoculation. Visible size of the oocysts can be assessed but species cannot be accurately determined. The level of sporulation can be judged in this technique.

TABLE 32

Oocyst counts on mixed litter samples from seeder birds used as challenge to each pen

| Sample No. | Mean oocyst/ gm litter | % large[1] oocysts | % medium[2] oocysts | % small[3] oocysts |
|---|---|---|---|---|
| 1 | 22,928 | 3.0 | 39.5 | 57.9 |
| 2 | 14,143 | 0 | 30.3 | 69.7 |
| 3 | 11,750 | 11.1 | 29.8 | 59.0 |
| 4 | 14,109 | 16.4 | 36.9 | 47.6 |
| Mean | 15,733 | 7.6 | 34.1 | 58.6 |

[1]Large oocysts typical of *E. maxima* or *E. brunetti*

[2]Medium oocysts typical of *E. tenella, E. necatrix* or *E. praecox*

[3]Small oocysts typical of *E. acervulina* or *E. mitis*

Based on the oocyst counts shown in Table 32, each pen received approximately 6.3 million oocysts in the distributed seeded litter on day 14.

Oocysts of sizes typical of several species of *Eimeria* were seen during counting of the challenge seeded litter (percentages estimated in Table 32). However, only the small oocysts seemed to be sporulated, with very few of the other sizes showing signs of sporulation at the time of litter spreading.

Figure 21:
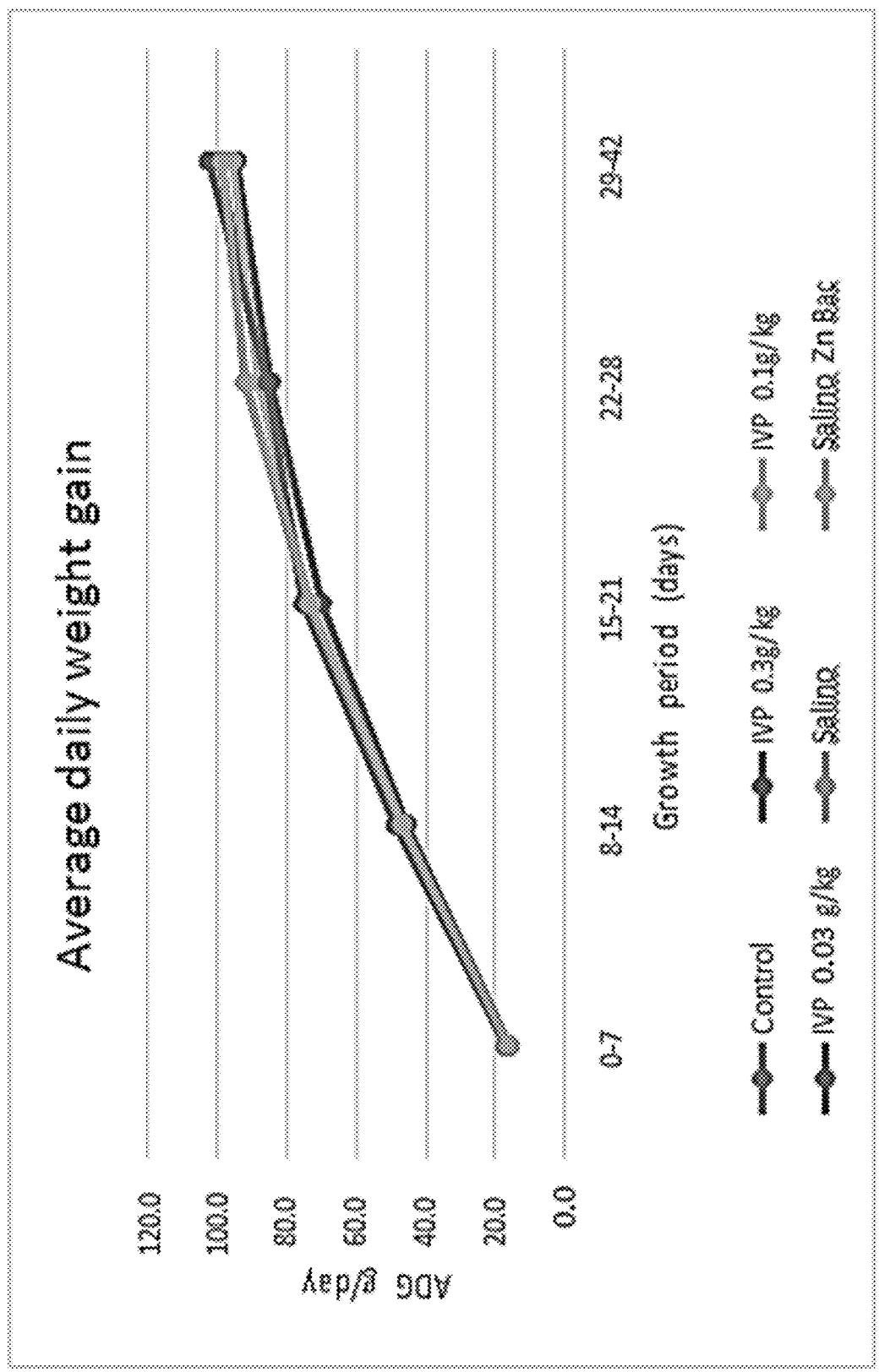
FIG. 21 is a graph of the average daily weight gain of birds in the study described in Example 3 by treatment group: Average Daily Gain (ADG) (g/day) on y-axis versus growth period (days) on x-axis. Treatment group 1 (control): Treatment group 2 (IVP 0.30 g/kg); Treatment group 3 (IVP 0.10 g/kg); Treatment group 4 (IVP 0.03 g/kg); Treatment group 5 (Salinomycin (Salino) 60 ppm); Treatment group 6 (Salinomycin+Zn Bacitracin 50 ppm (Salino Zn Bac)).

Table 33 shows mean weights at each weighing time and Table 34 shows the mean weight gain in each period. FIG. 21 shows average daily gain in weight by treatment.

TABLE 33

Mean live weights (gm) at each age

| Treatment/feed | 0 days | 7 days | 14 days | 21 days | 28 days | 42 days |
|---|---|---|---|---|---|---|
| Negative Control | 41 | 163 | 457$^A$ | 982$^{AB}$ | 1591$^A$ | 2983$^A$ |
| IVP 0.30 g/kg | 41 | 154 | 432$^B$ | 923$^C$ | 1517$^B$ | 2840$^B$ |
| IVP 0.10 g/kg | 41 | 163 | 456$^A$ | 972$^{AB}$ | 1590$^A$ | 2932$^A$ |
| IVP 0.03 g/kg | 41 | 160 | 461$^A$ | 989$^A$ | 1590$^A$ | 3026$^A$ |
| Salinomycin 60 ppm | 41 | 157 | 446$^{AB}$ | 963$^{AB}$ | 1608$^A$ | 2991$^A$ |
| Salinomycin + Zn Bacitracin | 41 | 156 | 443$^{AB}$ | 955$^B$ | 1599$^A$ | 2976$^A$ |
| P = | 0.42 | 0.08 | 0.006 | 0.0002 | 0.036 | 0.059 |

$^{A,B,C}$-means with different superscripts differ significantly (P <0.05), ANOVA, separated using Duncan's Multiple Range test.

TABLE 34

Weight gain by period

Mean Weight Gain (gm) over each period (days)

| Treatment/feed | 0-7 | 8-14 | 15-21 | 22-28 | 29-42 |
|---|---|---|---|---|---|
| Negative | 122 | 335$^A$ | 525$^A$ | 608 | 1393 |
| IVP 0.30 g/kg | 113 | 320$^C$ | 491$^B$ | 593 | 1324 |
| IVP 0.10 g/kg | 121 | 334$^A$ | 517$^A$ | 618 | 1341 |
| IVP 0.03 g/kg | 119 | 343$^A$ | 528$^A$ | 600 | 1436 |
| Salinomycin 60 ppm | 116 | 330$^{BC}$ | 517$^A$ | 645 | 1384 |
| Salinomycin + Zn Bacitracin | 115 | 327$^{BC}$ | 512$^A$ | 644 | 1377 |
| P = | 0.08 | 0.01 | 0.001 | 0.14 | 0.14 |

$^{A,B,C}$-means with different superscripts differ significantly (P <0.05), ANOVA, separated using Duncan's Multiple Range test.

Weights at 14 days had shown significant divergence with treatments with birds receiving 0.3 g/kg IRP having significantly lower weights than the negative control and both of the lower IRP dose rates. Both feeds containing salinomycin were intermediate at 14 days. This trend was becoming obvious at 7 days but not significantly at that age. This was also reflected in weight gain over these periods. By 21 days the mean weight of birds in the 0.3 g/kg IVP treatment group was significantly lower than any other treatment. IVP at 0.03 g/kg at 21 days had the highest numerical mean weight and was significantly greater than the salinomycin+bacitracin group and 0.3 g/kg IRP group. Birds receiving IVP 0.3 g/kg remained significantly lighter than all other groups to the end of the experiment, although rate of gain after day 21 did not differ between the groups. The coccidosis challenge experienced did not significantly decrease growth rate in the negative controls compared with treated groups.

Figure 22:
FIG. 22 depicts a comparison between control finisher and the IVP used in Example 3, Treatment Group 2 (dose of IVP 0.30 g/kg).
Figure 23:
FIG. 23 depicts faeces at 42 days from birds from Treatment Group 2 (dose of IVP 0.30 g/kg), Example 3.

The IVP 0.3 g/kg group had significantly lighter weights than the control and lower IVP dose groups from 14 days onwards. This group (feed #2) consumed less feed over the trial than any other group and much less feed than the two other groups treated with the IVP (Table 35). The feed for this group was bright yellow in colour (FIG. 22) and by 42 days there were undigested feed particles visible in the faeces of these birds (FIG. 23). The slower growth rate with the IVP 0.3 g/kg dose can be seen in FIG. 21. Birds always appeared healthy.

The coccidiosis challenge did not depress the growth rate of the negative control group during the week of challenge (15-21 days).

Growth rates of the lower IVP dose groups and the salinomycin and salinomycin+bacitracin groups were statistically similar to the control group throughout the experiment.

Table 35 shows feed intake per bird and Table 36 shows feed conversion ratios (FCR=feed:gain ratio) corrected for bird losses.

Feed intake for birds receiving IVP at 0.3 g/kg over days 0-14 and 0-21 and for both feeds containing salinomycin over days 0-21 had significantly lower feed intake per bird than the controls. IVP at 0.1 g/kg and 0.03 g/kg had similar feed intake to the controls. No significant feed intake differences were seen thereafter.

TABLE 35

Feed intake per bird

Feed per bird (g/bird) over period (days)

| Feed | 0-14 | 0-21 | 0-28 | 0-42 |
|---|---|---|---|---|
| Neg control | 514$^A$ | 1277$^A$ | 2072 | 4489 |
| IVP 0.3 g/kg | 485$^B$ | 1186$^B$ | 1957 | 4121 |
| IVP 0.1 g/kg | 513$^A$ | 1227$^{AB}$ | 2037 | 4247 |
| IVP 0.03 g/kg | 512$^A$ | 1240$^{AB}$ | 2049 | 4305 |
| Salino | 497$^{AB}$ | 1193$^B$ | 2074 | 4298 |
| Salino + Zn Bacitracin | 498$^{AB}$ | 1195$^B$ | 2007 | 4129 |

$^{A,B}$means with different superscripts differ significantly (P < 0.05)

FCR (corrected for bird losses and removals) only showed significant variation after the entire trial period (over days 0-42). Both feeds containing salinomycin (#5 & #6) had significantly better FCR than the controls and the feed which also contained bacitracin (#6) had significantly better FCR than the IVP 0.1 g/kg group (#3). The minor differences in sex ratio determined between groups did not have a significant effect on bird performance (not shown).

TABLE 36

FCR corrected for mortality

| Feed | FCR 0-14 | FCR 0-21 | FCR 0-28 | FCR 0-42 |
|---|---|---|---|---|
| Negative Control | 1.123 | 1.299 | 1.474 | 1.607$^A$ |
| IVP 0.30 g/kg | 1.120 | 1.285 | 1.470 | 1.560$^{ABC}$ |

TABLE 36-continued

| | FCR corrected for mortality | | | |
|---|---|---|---|---|
| Feed | FCR 0-14 | FCR 0-21 | FCR 0-28 | FCR 0-42 |
| IVP 0.10 g/kg | 1.125 | 1.256 | 1.467 | 1.599$^{AB}$ |
| IVP 0.03 g/kg | 1.103 | 1.250 | 1.486 | 1.563$^{ABC}$ |
| Salinomycin 60 ppm | 1.113 | 1.238 | 1.470 | 1.546$^{BC}$ |
| Salinomycin + Zn Bacitracin | 1.116 | 1.246 | 1.448 | 1.527$^{C}$ |
| P= | 0.75 | 0.18 | 0.60 | 0.008 |

$^{A,B,C}$means with different superscripts differ significantly (P < 0.05), ANOVA, separated using Duncan's Multiple Range test.

Table 37 shows the results of coccidial lesions cores at day 21 (7 days post exposure to contaminated litter).

TABLE 37

Coccidiosis lesion scores

| | Mean Coccidiosis Lesion Scores (maximum 4 in each region) by gut region day 21 | | | | |
|---|---|---|---|---|---|
| Feed | Duodenum | Jejunum | Ileum | Caeca | Total |
| Negative Control | 2.25$^{A}$ | 1.05$^{A}$ | 0.00 | 0.00 | 3.30$^{A}$ |
| IVP 0.30 g/kg | 1.35$^{ABC}$ | 0.30$^{B}$ | 0.00 | 0.10 | 1.75$^{B}$ |
| IVP 0.10 g/kg | 1.85$^{AB}$ | 1.25$^{A}$ | 0.05 | 0.00 | 3.15$^{A}$ |
| IVP 0.03 g/kg | 1.90$^{AB}$ | 0.45$^{B}$ | 0.00 | 0.05 | 2.40$^{AB}$ |
| Salinomycin 60 ppm | 1.35$^{ABC}$ | 0.40$^{B}$ | 0.00 | 0.00 | 1.75$^{B}$ |
| Salinomycin + Zn Bacitracin 50 ppm | 0.95$^{C}$ | 0.10$^{B}$ | 0.05 | 0.10 | 1.20$^{B}$ |
| P= | 0.03 | 0.01 | 0.56 | 0.24 | 0.02 |

$^{A,B,C}$means with different superscripts differ significantly (P < 0.05), ANOVA, separated using Duncan's Multiple Range test.

The coccidial lesions were mainly of those typical of *E. acervulina*. PCR on the challenge litter showed the presence of *E. maxima. E. tenella* and *E. mitis* as well. This is consistent with oocyst data prior to challenge insomuch as looking at the oocysts when they were counted prior to challenge, only the smaller oocysts (*E. acervulina* and *E. mitis*) appeared to have a good level of sporulation.

Figure 24:
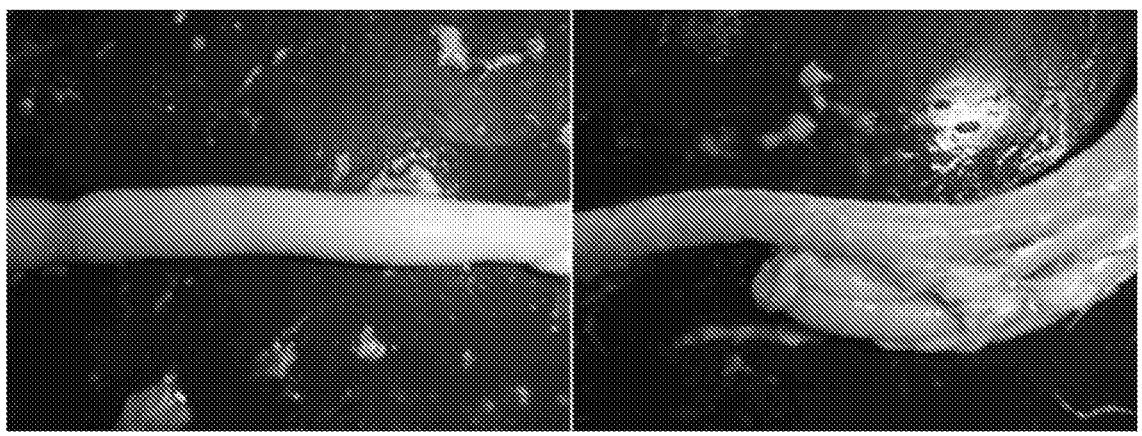
FIG. 24 *E. acervulina*-type lesions (from outside and inside the duodenum), score +1, from Example 3.
Figure 25:
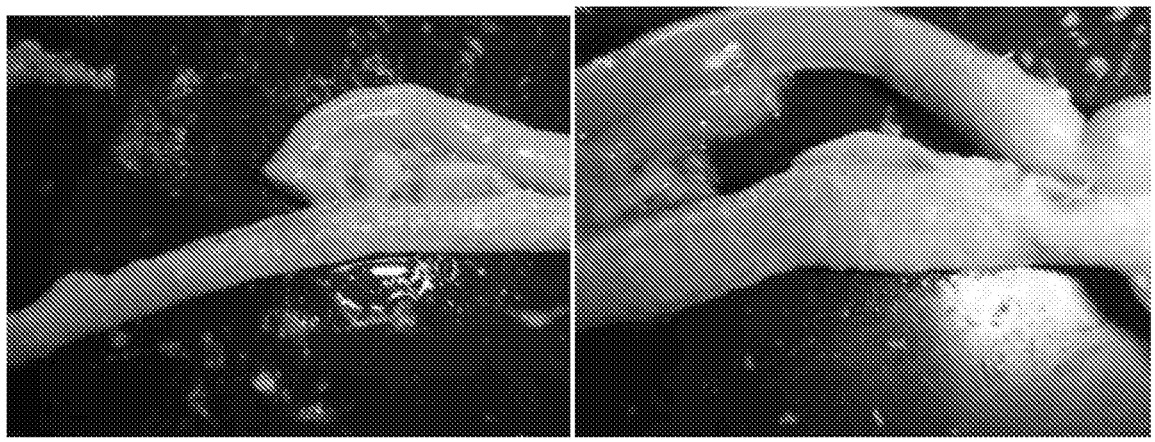
FIG. 25 *E. acervulina*-type lesions, scores +2 and +3, from Example 3.
Figure 26:
FIG. 26 *E. acervulina*-type lesions, score +4 from Example 3.

The negative control and the lowest level of the IVP showed the highest lesion scores in duodenum, jejunum and total gut. Location of the lesions and their appearance were typical of *E. acervulina* (see FIG. 24 to FIG. 26). In the duodenum, only Salinomycin plus bacitracin reduced the lesions significantly compared to the control and the two lower dose rates of IVP. Jejunal lesions were generally low but there were some significant differences. Overall, the highest level of IRP and Salinomycin containing feeds (#5 & #6) significantly reduced total gut lesion scores.

Pooled faecal samples from each pen were assessed for oocyst content. Table 38 shows the results. Results showed some consistency however oocyst counts in the faecal sample from one pen (in the 0.1 g IVP/kg group was extremely high (checked twice). This individual pen also showed very high coccidial lesion scores. This skewed the result for this treatment group. Raw oocyst counts were observed not to be homogeneous (by a significant Levene's test), hence counts were transformed to base 10 logarithms to overcome this problem for ANOVA analysis. The transformed log 10 results are also shown in Table 38. Although the oocyst counts in faeces were numerically lower for the IVP treated feed groups (#2, #3 & #4), only the feeds containing salinomycin (#5 & #6) significantly reduced oocyst counts in faeces compared with the negative controls.

TABLE 38

Faecal oocyst counts

| | Oocyst/g faeces | | | Log$_{10}$ (Oocyst/g faeces) | |
|---|---|---|---|---|---|
| Treatment | Mean | Std Dev | Coefficient of variation | Mean | Std Dev |
| Neg control | 266,615 | 109,155 | 40.9 | 5.39$^{A}$ | 0.19 |
| IRP 0.3 g/kg | 176,451 | 209,942 | 119.0 | 5.08$^{AB}$ | 0.38 |
| IRP 0.1 g/kg | 798,976 | 1,366,641 | 171.0 | 5.46$^{A}$ | 0.64 |
| IRP 0.03 g/kg | 92,206 | 45,375 | 49.2 | 4.90$^{AB}$ | 0.29 |
| Salinomycin | 72,046 | 49,588 | 68.8 | 4.72$^{B}$ | 0.44 |
| Salino + Zn Bac | 84,473 | 66,306 | 78.5 | 4.78$^{B}$ | 0.44 |
| P= | | | 0.33 | | 0.041 |

$^{A,B}$means with different superscripts differ significantly (P < 0.05), ANOVA, separated usingDuncan's Multiple Range test.

Figure 27:
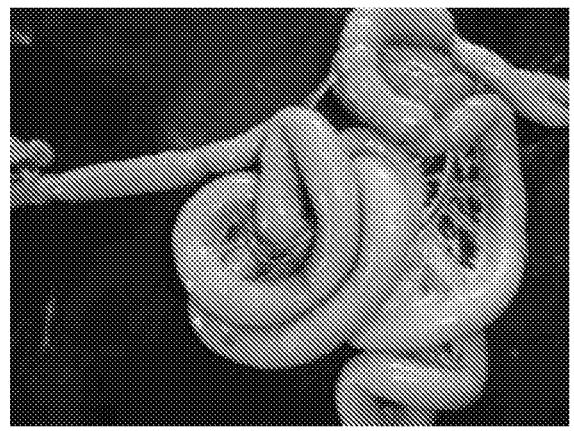
FIG. 27 ballooning of intestine from Example 3.
Figure 28:
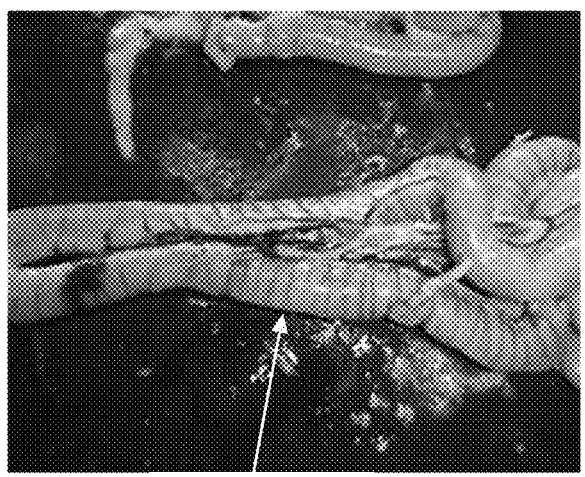
FIG. 28 Hyperaemia (white arrow; left hand side caption) of upper gut and intestinal translucency (black arrow; right hand side caption) from Example 3.
Figure 28:
Figure 29:
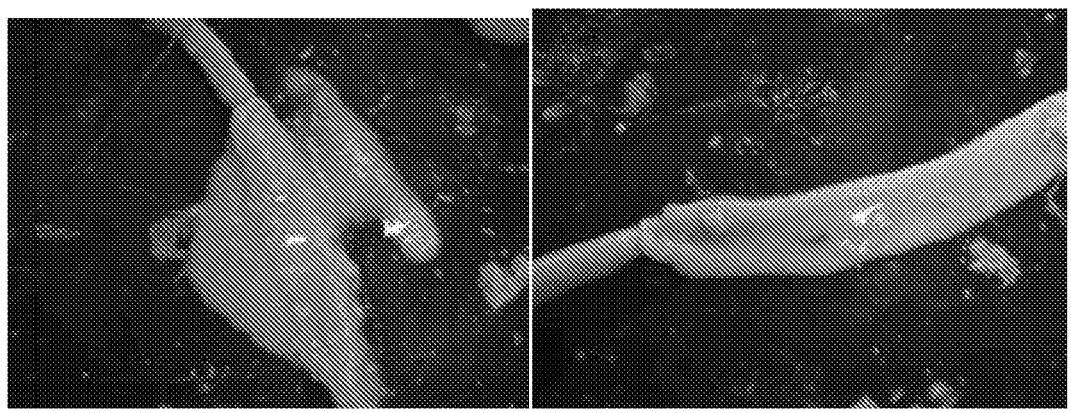
FIG. 29 Watery gut contents, including orange-coloured mucus from Example 3.

Table 39 shows the intestinal lesion scores based on Tierlynck et al. *Avian Pathology*, 2011, 40:139-144 (Tierlynck et al., 2011). This is a scoring system aimed at quantifying the level of dysbacteriosis present in a group of birds, attributing scores for certain grossly visible abnormalities. Higher total scores (maximum 10) reflect a higher level of dysbacteriosis, although this may be compromised if coccidiosis is present. For our purposes, the intestinal scores simply reflect gross gut pathology. Examples of some observed intestinal abnormalities are shown in FIG. 27 to FIG. 29.

Mean intestinal integrity scores at 21 days were lower than at 28 days in this experiment. At 21 days the areas of the intestine which raised the intestinal score were ballooning, hyperaemia, translucency and abnormal contents in the upper intestine and presence of undigested feed particles in the rectum. At 28 days the areas contributing to the higher scores were ballooning and hyperaemia, translucency and tonus in the upper intestine.

There were no significant differences in total intestinal health scores across any treatments at either 21 nor 28 days, however at 21 days the higher two levels of the IVP (0.3 and 0.1 g/kg) and both feeds containing salinomycin reduced translucency score in the upper intestine and the presence of undigested feed particles in the rectum compared with the controls and the lowest level of the IVP (0.03 g/kg). At 28 days, the IVP at 0.3 g/kg produced total intestinal health scores that approached significance compared with the controls (P=0.06).

TABLE 39

Intestinal health scores based on Tierlynck et al. 2011 at 21 and 28 days.

| Age (days) | Feed | Ballooning (total gut) | Hyperaemia upper intestine | Translucency upper intestine | Tonus upper intestine | Contents upper intestine | Hyperaemia lower intestine | Translucency lower intestine | Tonus lower intestine | Contents lower intestine | Undigested particles in rectum | Total Intestine |
|---|---|---|---|---|---|---|---|---|---|---|---|---|
| 21 | Neg control | 0.45 | 0.35 | $0.45^{AB}$ | 0.25 | 0.75 | 0.05 | 0.55 | 0.35 | 0.45 | $0.45^A$ | 4.10 |
| | IRP 0.3 g/kg | 0.25 | 0.20 | $0.25^B$ | 0.15 | 0.80 | 0.05 | 0.85 | 0.35 | 0.10 | $0.10^B$ | 3.10 |
| | IRP 0.1 g/kg | 0.28 | 0.25 | $0.20^B$ | 0.25 | 0.85 | 0.05 | 0.60 | 0.35 | 0.40 | $0.30^A$ | 3.53 |
| | IRP 0.03 g/kg | 0.23 | 0.35 | $0.55^A$ | 0.35 | 0.75 | 0.10 | 0.75 | 0.40 | 0.35 | $0.05^B$ | 3.88 |
| | Salino | 0.10 | 0.15 | $0.20^B$ | 0.50 | 0.65 | 0.00 | 0.85 | 0.50 | 0.45 | $0.15^B$ | 3.55 |
| | Sal Zn Bac | 0.13 | 0.40 | $0.40^{AB}$ | 0.20 | 0.75 | 0.15 | 0.40 | 0.25 | 0.30 | $0.15^B$ | 3.13 |
| | P = | 0.11 | 0.57 | 0.04 | 0.65 | 0.81 | 0.40 | 0.08 | 0.93 | 0.22 | 0.02 | 0.45 |
| 28 | Neg control | 0.80 | 0.80 | 0.60 | 0.80 | 1.00 | 0.60 | 0.80 | 0.60 | 0.40 | 0.40 | 6.80 |
| | IRP 0.3 g/kg | 1.00 | 0.60 | 0.40 | 0.20 | 0.60 | 0.00 | 0.80 | 0.40 | 0.00 | 0.20 | 4.20 |
| | IRP 0.1 g/kg | 0.80 | 1.00 | 0.60 | 0.60 | 1.00 | 0.20 | 0.40 | 0.40 | 0.40 | 0.40 | 5.80 |
| | IRP 0.03 g/kg | 0.60 | 0.80 | 0.00 | 0.80 | 0.60 | 0.00 | 0.80 | 1.00 | 0.00 | 0.40 | 5.00 |
| | Salino | 0.80 | 0.80 | 0.40 | 0.80 | 1.00 | 0.20 | 0.20 | 0.60 | 0.00 | 0.40 | 5.20 |
| | Sal Zn Bac | 1.00 | 0.40 | 0.20 | 0.60 | 0.60 | 0.20 | 1.00 | 1.00 | 0.20 | 0.40 | 5.60 |
| | P = | 0.59 | 0.40 | 0.35 | 0.35 | 0.20 | 0.20 | 0.06 | 0.14 | 0.24 | 0.99 | 0.06 |

$^{A,B}$-means with uncommon superscripts differ significantly (P <0.05)

TABLE 40

Significant correlations between performance and observations (Pearson correlation coefficients).

| | Total coccidiosis lesion scores day 21 | $Log_{10}$ oocysts in faeces day 21 | Intestinal Ballooning day 21 | Undigested feed in rectum day 21 | Intestinal integrity score day 28 |
|---|---|---|---|---|---|
| C FCR 42 days | 0.70 | 0.42 | 0.41 | 0.51 | 0.39 |
| Total coccidiosis lesion scores d 21 | | 0.38 | ns[1] | 0.44 | 0.51 |
| $Log_{10}$ oocysts in faeces d 21 | 0.38 | | 0.40 | ns | ns |
| Intestinal integrity score d 21 | 0.51 | ns | ns | ns | ns |

[1]not significant (P > 0.05)

Figures shown are Pearson correlation coefficients (r) and reveal a significant relationship (P < 0.05) between the column and row factors.

Figure 30:
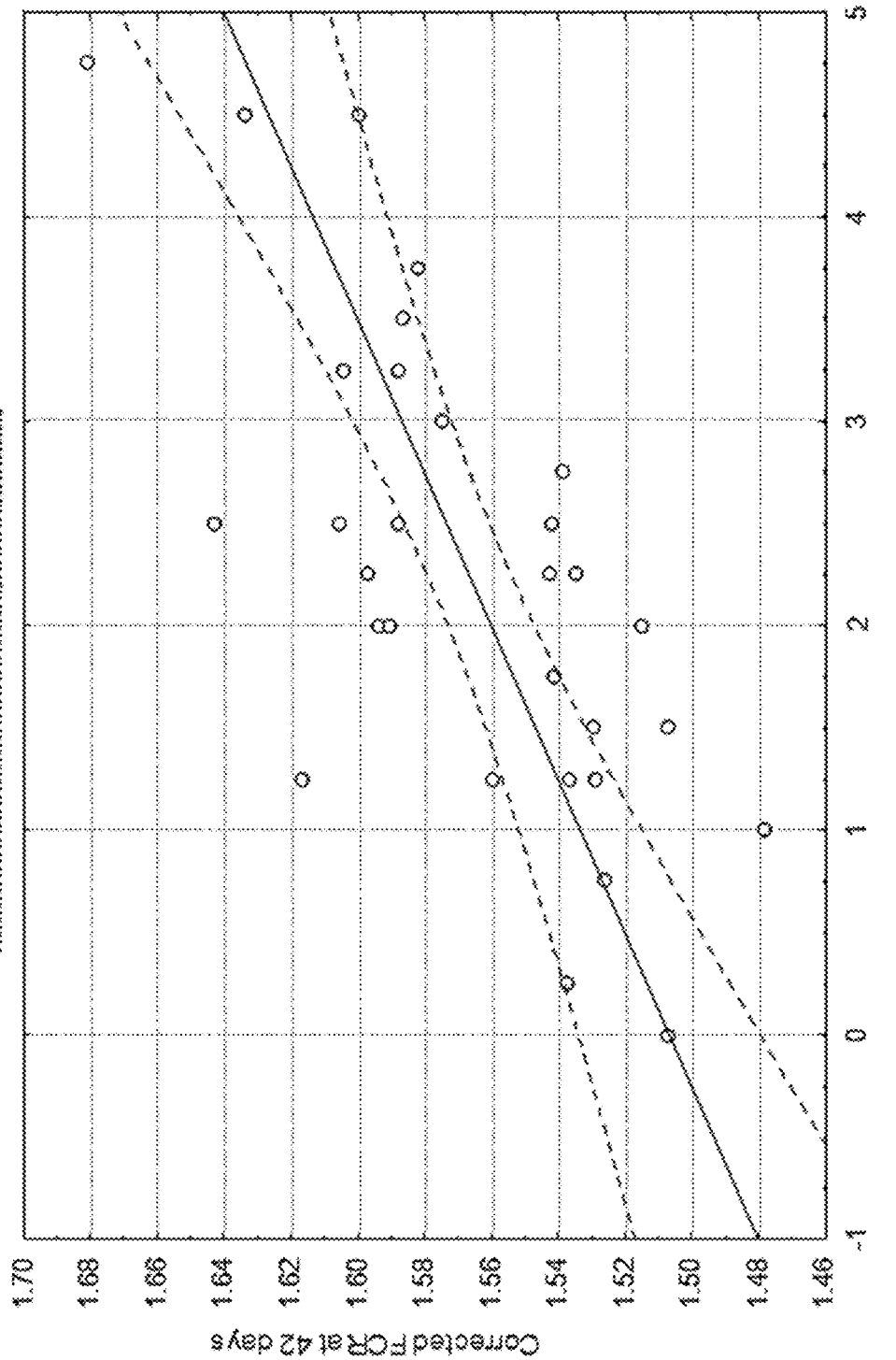
FIG. 30 depicts the correlation between corrected Feed Conversion Ratio at 42 days and total intestinal coccidiosis lesion scores at 21 days. The solid line shows the line of best fit; dashed lines show 95% confidence intervals.

Corrected feed conversion ratios at 42 days had a significant and strong positive correlation (r=0.70) with total coccidiosis lesions scores at day 21 (i.e. higher lesion scores were associated with higher FCR and the variation in these lesions accounted for 83% of the variation in FCR). This relationship is shown graphically in FIG. 30. Coccidial lesions cores were moderately positively correlated with oocyst numbers in faeces at 21 days (variation in one accounted for 62% of variation in the other). Intestinal ballooning at 21 days was moderately associated with faecal oocsyt counts on day 21 and with FCR at 42 days. The presence of a higher level of undigested feed particles in the rectum at day 21 was correlated with higher coccidial lesion scores and with poorer (higher) FCR at day 42. Total intestinal integrity scores at day 28 also showed moderate positive correlation with coccidial lesion scores from day 21 and with FCR at day 42.

Discussion and Conclusions

Although the coccidial challenge applied contained several species of *Eimeria*, only the *E. acervulina* type showed good sporulation at the time of challenge. Sporulation conditions are generally considered to be the same for all species so this observation is unusual and the reason for it unknown. The observation was certainly accurate as only *E. acervulina*-type lesions were seen at examination on day 21. *E. acervulina* is a lower pathogenicity species and is not likely to lead to mortality and has less effect on growth rate. It may produce diarrhoea and affect feed conversion efficiency however.

The challenge applied produced moderate coccidial lesions in the negative control group which were significantly reduced by the feds containing salinomycin and by the feed containing 0.30 g/kg IVP; but not by the lower dose rates. Only the salinomycin containing feeds were able to significantly reduce oocyst levels in faeces at day 21 although all groups receiving IVP levels were numerically lower than the controls. So there would appear to be some effect of IVP against *E. acervulina*.

Early growth rate of chicks receiving feed containing 0.30 g/kg of IVP was significantly lower than all other groups (up to 21 days), and although their rate of growth improved subsequently, they remained the lightest birds in the experiment. This was associated with a lower feed intake per bird to day 21. The feed with this higher level of IVP was bright yellow in colour and the birds eating it exhibited moist yellow-ish droppings. Whether this lower feed intake was due to palatability cannot be determined exactly and would require further evaluation, the prevalence of loose droppings may indicate an unfavourable effect of some nature at this inclusion rate.

Corrected feed conversion ratio over the whole trial (days 0-42) was slightly reduced by all treatments, but only significantly so by the feeds containing salinomycin, compared with the negative controls. FCR was strongly correlated with coccidial lesion scores at 21 days and moderately with faecal oocyst numbers and some intestinal integrity scores (ballooning, undigested feed particles in the rectum at day 21 and with total intestinal score at day 28). 83% of the variation in FCR at day 42 could be statistically explained by variation in coccidial lesion score at day 21. Intestinal ballooning is a sign frequently described associated with coccidosis. As day 28 intestinal scores were also moderately correlated to coccidial lesion scores at day 21 we may assume an effect of the coccidial infection continuing on in the gut after their lesions had resolved (no coccidial lesions were observed at day 28). The intestinal scoring system is aimed at quantifying the presence and level of the condition known as dysbacteriosis in broiler chickens, and this condition is thought to be provoked by coccidial infection. The intestinal integrity scores were higher (i.e. more severe) at day 28 than at day 21 and would suggest a level of dysbacteriosis to be present. The treated feeds decreased intestinal scores at a level that approached statistical significance (P=0.06) compared to the negative controls. In this respect, the IVP provided a similar improvement to salinomycin and salinomycin plus zinc bacitracin. This would be reasonable evidence that the IVP may have some protective effect against dysbacteriosis.

Campylobacteriosis

Campylobacteriosis is a gastrointestinal disease caused by bacteria called *Campylobacter* (CB). In Australia, CB is one of the most common causes of bacterial gastroenteritis and is frequently associated with the consumption of contaminated poultry. Infection can occur at any time of the year, but is more common the warmer months. In 2011, *Campylobacter* was the fourth leading cause of foodborne illness in the United States.

Most people who become infected with CB will get diarrhoea, cramping, abdominal pain, and fever that lasts from one to two weeks. Symptoms usually develop within 2 to 5 days after infection. The diarrhoea may contain blood or mucous. In rare cases, CB can enter the bloodstream and cause more serious disease.

Figure 3:
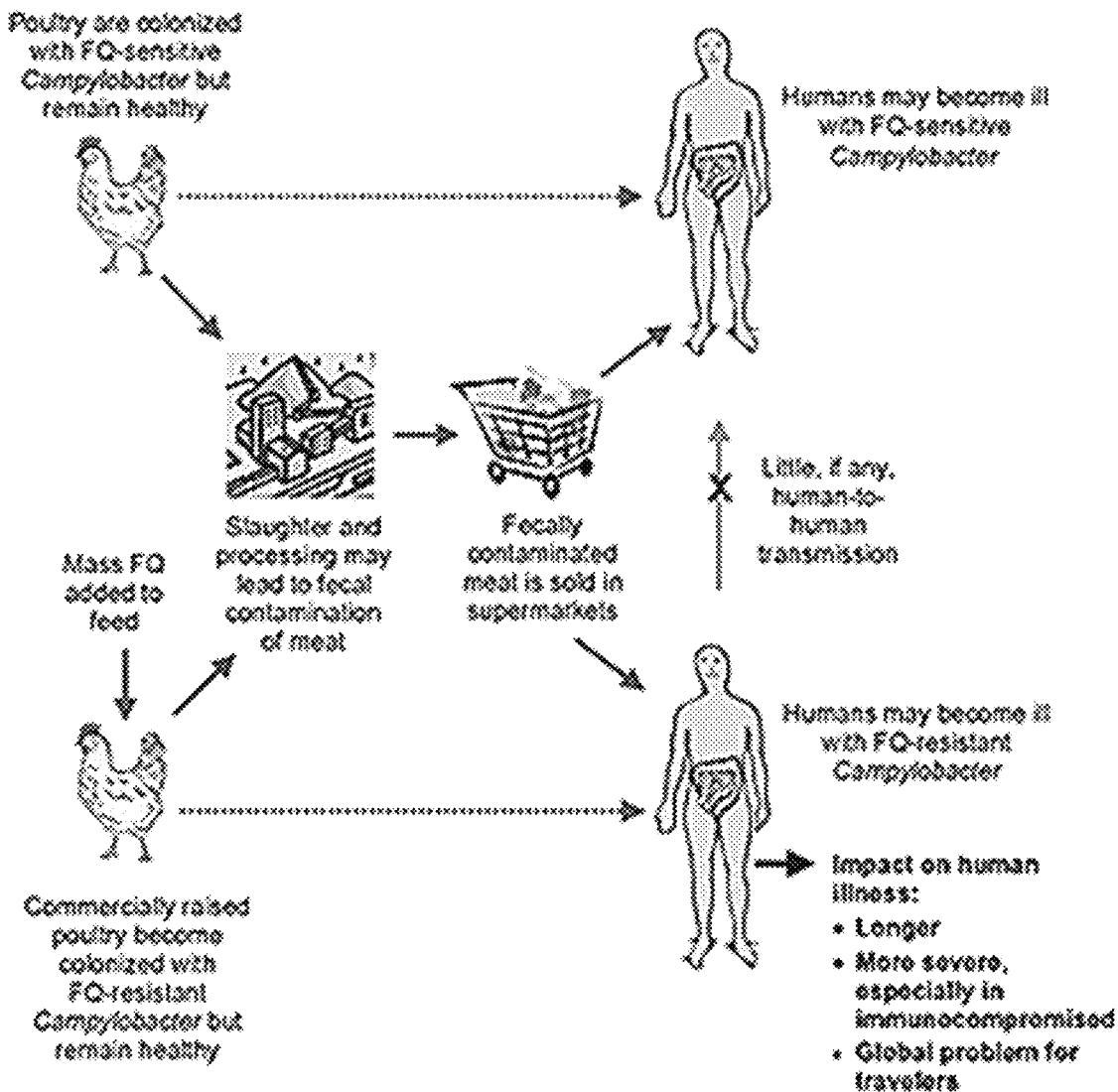
FIG. 3 depicts *Campylobacter* epidemiology. Figure is taken from https://wwwnc.cdc.gov/eid/article/10/6/04-0403-f1.

CB is mainly spread to humans by eating or drinking contaminated food (mainly poultry), water or unpasteurised milk. CB can also be spread through contact with infected people, or from contact with cats, dogs and farm animals that carry the bacteria (FIG. 3 shows the epidemiology).

Anyone can get campylobacteriosis, although very young children, the elderly, people with poor immunity and people who work with farm animals are at greater risk of infection.

Most people will recover from campylobacteriosis with rest and fluids. It usually takes one week to recover, but can take as long as two weeks. Treatment usually involves a rehydration solution, available from your pharmacist, to help with the dehydration resulting from the diarrhoea. In severe or complicated cases, antibiotics such as Erythromycin may be prescribed to reduce the duration of the illness.

There is a continued occurrence of CB contamination of poultry carcass/meat. Methods to control CB contamination have been focused at the processing plant through washing and evisceration. However, it is thought that if CB colonisation can be controlled in the birds" intestinal tract, prior to slaughter, then contamination of the processed birds will be reduced.

Example 4 discloses the antimicrobial activity of certain natural compounds against *Campylobacter*.

Example 4

Laboratory Work

Natural compounds were identified for potential use in the prevention and treatment of *Campylobacter* induced disease. In vitro Minimum inhibitory concentrations (MIC) and Minimum bactericidal concentration (MBC) were tested.
  1. Berberine chloride
  2. Berberine sulfate
  3. Arecoline
  4. Anemonin
  5. Matrine
  6. Oxymatrine
  7. Andrographolide 8. Palmatine
9. Baicalin Materials and Methods The Clinical and Laboratory Standards Institute (CLSI) guidelines were adopted for this project. Ten representative strains were selected. Concentrations tested for each compound were: 1000, 500, 250, 125, 62.5 µg/ml. Positive control used was Tetracycline.

TABLE 41

Campylobacter strains tested for MIC and MBC

| SNP Type | Isolate no. | State | Species |
|---|---|---|---|
| Reference strain | C70 | ATCC 33560 | C. jejuni |
| 284 | C1334 | Queensland | C. jejuni |
| 310 | C1394 | New South Wais | C. jejuni |
| 206 | C1478 | Victoria | C. jejuni |
| 277 | C1998 | Western Australia | C. jejuni |
| 34 | C1571 | South Australia | C. jejuni |
| 17 | C1874 | New South Wales | C. jejuni |
| 189 | C1496 | Tasmania | C. jejuni |
|  | C1829 | New South Wales | C. coli |
|  | C1319 | Queensland | C. coli |
|  | C1436 | Victoria | C. coli |

Results

TABLE 42

Campylobacter in vitro results

| Test | Results* |
|---|---|
| MIC | Two compounds exhibited MICs of 62.5 µg/ml. |
| MBC | The same two compounds exhibited MBC of 62.5 µg/ml. |

*Tetracycline results were in-line with reference standard for both MIC and MBC.

Diseases of the Pig
E. coli—Scour (Diarrhoea)

Of all the diseases in the sucking piglet, diarrhoea is the most common and probably the most important. In some outbreaks it is responsible for high morbidity and mortality. In a well-run herd there should be less than 3% of litters at any one time requiring treatment and piglet mortality from diarrhoea should be less than 0.5%. In severe outbreaks levels of mortality can rise to 7% or more and in individual untreated litters up to 100%. The main bacterial cause is E. coli. Scour in the piglet can occur at any age during sucking but there are often two peak periods, before 5 days and between 7 and 14 days.

For the acute disease, the only sign may be that a perfectly good pig is found dead. Post-mortem examinations show severe acute enteritis, so sudden that there may be no evidence of scour externally. Clinically affected piglets huddle together shivering or lie in a corner. The skin around the rectum and tail are wet. Looking around the pen there may be evidence of a watery to salad cream consistency scour. In many cases, there is a distinctive smell. As the diarrhoea progresses the piglet becomes dehydrated, with sunken eyes and a thick leathery skin. The scour often sticks to the skin of other piglets giving them an orange to white colour. Prior to death piglets may be found on their sides paddling and frothing at the mouth.

In the sub-acute disease, the symptoms are similar but the effects on the piglet are less dramatic, more prolonged and mortality tends to be lower. This type of scour is often seen between 7 to 14 days of age manifest by a watery to thin salad cream consistency diarrhoea, often white to yellow in colour.

Piglet scour is estimated to cost the Australian pig industry more than $7 million each year. The incidence and type of scours, health costs and recovery rate determine the extent of this loss in individual piggeries. Antidiarrhoeal agents such as Bentonite or Kaolin clay are used to protect the gut wall. Addition of electrolytes to drinking is also oftentimes used. Antibiotics are used to reduce the population of bacteria in the gut although drug abuse needs to be avoided as resistance will develop. Current antibiotic medicines are listed in Table 43 below.

TABLE 43

Antibiotics used to treat piglet diarrhoea

| | Method of Dosing | |
|---|---|---|
| Medicine | Oral | Injection |
| Amoxycillin | X | X |
| Ampicillin | X | X |
| Apramycin | X |  |
| Ceftiofur |  | X |
| Chloramphenicol* |  | X |
| Enrofloxacin | X | X |
| Framycetin |  | X |
| Furazolidone* | X |  |
| Neomycin | X |  |
| Spectinomycin | X |  |
| Streptomycin* | X | X |
| Sulphonamides | X | X |
| Trimethoprim/Sulpha | X | X |
| Tylosin |  | X |

*Banned in some countries

Example 5 discloses the antimicrobial activity of certain natural compounds against pig disease.

Example 5

Laboratory Work

Natural compounds were identified for potential use in the prevention and treatment of infectious intestinal disease in pig including scour-inducing E. Coli. In vitro Minimum inhibitory concentrations (MIC) were tested. The compounds tested were.
 1. Berberine chloride
 2. Berberine sulfate
 3. Arecoline
 4. Anemonin
 5. Matrine
 6. Oxymatrine
 7. Andrographolide
 8. Palmatine
 9. Baicalin Materials and Methods The Clinical and Laboratory Standards Institute (CLSI) guidelines were adopted for this project following the method for evaluating MIC adapted from Wiegland et al. "Agar and broth dilution methods to determine the minimal inhibitory concentration (MIC) of antimicrobial substances" Nature Protocols 2008; 3 (2): 163-175. Representative strains were selected. Concentrations tested for each compound were: 1000, 500, 250, 125, 62.5 µg/ml. Positive control used was Tetracycline.

TABLE 44

Pig disease strains tested for MIC

| SNP Type | Isolate no. | State | Species |
|---|---|---|---|
| 1498 | 162 | Victoria | E. coli |
| 1501 | 1229 | Victoria | E. coli |
| 1502 | 1232 | Victoria | E. coli |
| 1505 | 1455 | New South Wales | E. coli |
| 1507 | 1514 | South Australia | E. coli |

Results

Berberine and palmatine exhibited MICs of 125 µg/ml against all 5 strains of E. coli causing scour. Tetracycline results were in-line with standard results obtained for MIC.

Clostridium Difficile

Clostridium difficile (CD) is a bacterium that can cause conditions ranging from diarrhoea to life-threatening inflammation of the colon. Illness from CD most commonly affects older adults or in long-term care facilities and typically occurs after use of antibiotic medications. However, studies show increasing rates of CD infection among people traditionally not considered high risk, such as younger and healthy individuals without a history of antibiotic use or exposure to health care facilities. Each year in the United States, about a half million people get sick from CD, and in recent years, CD infections have become more frequent, severe and difficult to treat with the rise of antimicrobial resistance.

Some people carry the bacterium C. difficile in their intestines but never become sick, though they may still spread the infection. Signs and symptoms usually develop within five to ten days after starting a course of antibiotics, but may occur as soon as the first day or up to two months later. The most common symptoms of mild to moderate CD infection are water diarrhea and mild abdominal cramping. In severe cases, people tend to become dehydrated and may need hospitalization. The colon becomes inflamed (colitis) and sometimes may form patches of raw tissues that can bleed or produce pus.

The antibiotics that most often lead to CD infections include Fluoroquinolones, Cephalosporins, Penicillins and Clindamycin. Ironically, the standard treatment for CD is another antibiotic. For mild to moderate infection, Metronidazole taken orally is often prescribed despite not FDA approved. For more severe cases, Vancomycin taken orally is prescribed. Fidaxomicin is another approved option to treat CD but costs considerably more. Up to 20 percent of people with CD get sick again. After two or more recurrences, rates of further recurrence increase up to 65 percent. Treatment for CD recurrence typically involves Vancomycin. Fecal microbiota transplant or stool transplant may be considered but is not yet FDA approved.

Thus, the present disclosure relates to a method for preventing or treating an infectious disease caused by bacteria from the genus Clostridium in humans comprising administering a berberine alkaloid.

The present disclosure also contemplates that a berberine alkaloid or animal feed disclosed herein may inhibit spore formation. The overgrowth of spores after antibiotic treatment is acknowledged to be a problem in humans. Thus, the present disclosure relates to preventing C. difficile spores overgrowing after antibiotic treatment by administration of a berberine alkaloid or animal feed disclosed herein.

Example 6 discloses the antimicrobial activity of certain natural compounds against Clostridium.

Example 6

Laboratory Work

Natural compounds were identified for potential use in the prevention and treatment of Clostridium Difficile. In vitro Minimum inhibitory concentrations (MIC) and Minimum bactericidal concentrations (MBC) were tested. Clostridium Perfringens was also tested. The natural compounds tested were:
1. Berberine chloride
2. Berberine sulfate
3. Arecoline
4. Anemonin
5. Matrine
6. Oxymatrine
7. Andrographolide
8. Palmatine
9. Baicalin Materials and Method The Clinical and Laboratory Standards Institute (CLSI) guidelines were adopted for this project. Guidelines were adopted for following the method for evaluating MIC adapted from Wiegland et al. "Agar and broth dilution methods to determine the minimal inhibitory concentration (MIC) of antimicrobial substances" Nature Protocols 2008; 3 (2): 163-175 and the method for evaluating MBC adapted from Chen "Novel therapeutic approaches targeting Clostridium difficile", in: Biology Dissertations, Boston (Mass.): Northeastern University, 2014. Representative strains were selected. Concentrations tested for each compound were: 1000, 500, 250, 125, 62.5 µg/ml. Positive control used was Vancomycin.

Results

TABLE 45

Clostridia in vitro results

| Disease | Results* |
|---|---|
| C. difficile | Berberine and palmatine exhibited MICs of 640-820 µg/ml against CD. The above compounds exhibited MBCs of 880-1000 µg/ml against CD. |
| C. perfringens | Berberine and palmatine exhibited MICs of 62.5-125 µg/ml against all 6 strains. |

*Vancomycin results were in-line with standard for both MIC and MBC.

Experimental Data

Minimum inhibitory concentration (MIC) assays were conducted for a Necrotic Enteritis strain of C. perfringens and a clinical isolate of C. difficile using Berberine sulfate as the test agent and Vancomycin as an established control. Berberine sulfate with a purity of 98.0% was obtained as a natural extract from Sichuan BioFarm Inc. The MIC of Berberine for C. perfringens was 125 µg/ml, however partial inhibition of growth could be seen at a concentration of 62.5 µg/ml, indicating the true MIC is in between these two values.

The Minimum Bacterial Concentration (MBC) of Berberine for *C. perfringens* was equal to the MIC (125 μg/ml), with 100% killing of viable cells observed at this concentration. The MIC of Berberine for *C. difficile* was found to be 500-1000 μg/ml (variation between the replicates). The MBC of Berberine for *C. difficile* was 1000 μg/ml. The MIC and MBC values for Berberine for *C. difficile* were equal to or within a 2-fold dilution of values from a previous study. Vancomycin MICs were within the expected range for both *C. perfringens* and *C. difficile*.

Example 7

This study aims to determine tissue residues of the naturally occurring plant compound IRP001 chloride (berberine chloride) when administered orally via feed to commercial broiler chickens.

Summary

Broiler chickens received either 0.3 g/kg or 0.03 g/kg IRP001 chloride mixed into their feed, or received regular feed without additive (i.e. control groups). Treatment began immediately after the birds were housed in pens (in groups of 10) and treatment continued for 35 days. Birds were either euthanized on day 35 for tissue collection or were fed beyond day 35 on regular feed for up to 7 days to examine residues after a washout period. Two other groups received IRP001 chloride feed additive for 28 days at either 0.3 g/kg or 0.03 g/kg mixed into their feed (i.e., 0.3 g IRP001 chloride in 1 kg of feed or 0.03 g IRP001 chloride in 1 kg of feed) and were subsequently fed on regular food for a washout period of 14 days prior to euthanasia and tissue collection.

IRP001 chloride was extracted from 1 g samples of three muscle tissues taken from each bird (in each case from breast, upper leg and lower leg). The residual mass of IRP001 chloride was determined using LC-MS/MS. The method allowed IRP001 to be detected with a lower limit of 2 ng IRP001/g tissue. The assay was fully validated during each assay run and proved to be quantitative to be better than +20% accuracy at 5 ng/g tissue. Levels lower than 2 ng IRP001/g were found to be within the baseline noise of the assay and were below the lower limit of detection (LLOD), i.e. IRP001 was not detectable.

In one embodiment, the method was optimized so that IRP001 chloride could be detected with certainty at 2 ng/g tissue. The assay was fully validated during each assay run and proved to be quantitative to better than +20% accuracy at 4 ng/g or 5 ng/g tissue. Levels of 1 ng/g tissue or below were found to be within the baseline noise of the assay and were below the lower limit of quantitation (LLOQ).

Residues of berberine were detectable and quantifiable after feeding for 35 days at the high IRP001 chloride concentration. The mean residue levels (n=3) at the high feed additive concentration after 35 days feeding without washout were 6.1 ng. 5.5 ng and 11.6 ng per gram of tissue in breast, lower leg and upper leg tissue respectively. A washout effect was evident at the high feed additive concentration in all three muscle tissues, reaching levels of approximately 1 ng/g, below the LLOQ after 4 days washout. At the low concentration of feed additive the mean residue levels were less than 1 ng/g, below the LLOQ, in all cases, with or without washout.

All residue levels determined in the study were below the nominated safe residue level of 13 ng/g, even when measured after 35 days feeding at 0.3 g IRP001 chloride/kg feed without a washout period.

The residue levels in the liver after the high feed additive concentration were above 13 ng/g without washout but below 13 ng/g after one day of washout. Given the average consumption of chicken liver is limited, the levels of IRP001 in liver do not represent cause for concern.

The data taken as a whole indicate that the risk of cancer resulting from consumption of chicken meat from IRP001 chloride-fed chickens is less than one in a million at feed additive levels equal to or less than 0.3 g berberine/kg feed.

Berberine levels in chicken muscle (i.e. chicken meat) were below the LLOD after dosing at 0.03 IRP001/kg feed, or after 4 days of washout after dosing at 0.3 g IRP001/kg feed.

Introduction

Berberine alkaloids, including berberine, are safe. Berberine has been used as a dietary supplement by humans for many years and is available from several manufacturers in capsule form. It is sold for use once or twice daily at doses as high as 400 mg berberine chloride per capsule. Further, in experiments leading to the present invention, no adverse reaction or unanticipated event has been observed in broilers treated with berberine at a dose of 1 g berberine in 1 kg of commercial feed over 42 days (see EXAMPLE 8).

As described elsewhere, in the US, the Food and Drug Administration (FDA) is responsible for the approval of human and animal drugs and feed additives which are governed by the Federal Food, Drug, and Cosmetic Act (FD&C Act).

The FD&C Act requires that compounds intended for use in food-producing animals are shown to be safe and that food produced from animals exposed to these compounds is shown to be safe for consumption by people. In particular, the use in food-producing animals of any compound found to induce cancer when ingested by people or animal is prohibited by statute (21 CFR Part 500, Subpart E—Regulation of carcinogenic compounds used in food-producing animals) unless certain conditions are met (the so-called "Diethylstilbestrol (DES) Proviso"). Under the DES proviso use of a suspected carcinogenic compound is not prohibited if it can be determined by prescribed methods of examination that "no residue" of that compound will be found in the food produced from food-producing animals under conditions of use reasonably certain to be followed in practice.

Thus, if the FDA decides that berberine should be regulated as a carcinogenic compound, US statue prohibits the use of berberine in food-producing animals unless the "no residue" DES proviso applies.

The term "no residue" refers to any residue remaining in the edible tissues that is so low that it presents an insignificant risk of cancer to consumers. More specifically, an insignificant risk of cancer is defined as a 1 in 1 million increase in risk.

Despite the recorded safety of berberine, a toxicology study was commissioned by the US Government (National Centre for Toxicological Research) and this study identified potential carcinogenicity in a high-dose chronic rodent study.

As a result to obtain GRAS status it has been necessary to estimate the maximum residue of berberine in chicken meat that would be acceptable, given the typical lifetime consumption of chicken meat. To ensure lower than a one in a million risk of cancer resulting from chicken consumption, it has been estimated that the maximum acceptable residue is 13 ng berberine per gram of chicken meat (i.e. breast or leg muscle tissue).

To investigate whether the disclosed feed additive is safe and suitable for GRAS status at specified doses a suitable residue trial was conducted. Invetus Pty Ltd was contracted to conduct a trial, collect tissue and Monash University was contracted to assay tissue samples for berberine.

Residue Study Design

The protocol for this study using broiler chickens is annexed to the Example as Appendix B. Two concentrations of IRP0001 chloride were investigated: 0.3 g/kg feed and 0.03 g/kg feed, representing high and low concentrations of feed additive.

One hundred and eighty birds were split into 18 pens, each containing 10 birds. To represent the typical farming process for broiler chickens, test birds received feed with additive for 35 days at either the high or low concentration. After 35 days one group at each additive concentration was euthanized for tissue collection (6 largest birds in each pen).

To investigate whether elimination (metabolism and excretion) of IRP001 chloride was evident when feed containing IRP001 chloride was replaced with regular feed, other groups received IRP001 chloride for 35 days and then were given regular feed for either 1, 2, 4 or 7 days prior to euthansia and tissue collection. Two additional groups received IRP001 chloride for 28 days and then regular feed for 14 days (i.e a 14 day washout). Parallel control groups were treated in exactly the same manner except that the control birds received regular feed throughout the study. In all cases, samples were taken from three regions of muscle tissue (breast, upper and lower thigh). Samples were collected, frozen and shipped for analysis. Table 46 summarises the study design showing the concentration of IRP001 used and the feeding regimen for each of the 18 groups of birds in the residue study.

TABLE 46

Summary of the feeding regime for each group of broilers

| Group | Bird type | Treatment | [IVP] in feed g/kg | Euthanasia (Day) | Treatment In feed Days | No. samples |
|---|---|---|---|---|---|---|
| 1 | Broiler | IRP001 | 0.03 | 35 | 0-35 | 6 |
| 2 | Broiler | IRP001 | 0.03 | 36 | 0-35 | 6 |
| 3 | Broiler | IRP001 | 0.03 | 37 | 0-35 | 6 |
| 4 | Broiler | IRP001 | 0.03 | 39 | 0-35 | 6 |
| 5 | Broiler | IRP001 | 0.03 | 42 | 0-35 | 6 |
| 6 | Broiler | IRP001 | 0.03 | 42 | 0-28* | 6 |
| 7 | Broiler | IRP001 | 0.3 | 35 | 0-35 | 6 |
| 8 | Broiler | IRP001 | 0.3 | 36 | 0-35 | 6 |
| 9 | Broiler | IRP001 | 0.3 | 37 | 0-35 | 6 |
| 10 | Broiler | IRP001 | 0.3 | 39 | 0-35 | 6 |
| 11 | Broiler | IRP001 | 0.3 | 42 | 0-35 | 6 |
| 12 | Broiler | IRP001 | 0.3 | 42 | 0-28* | 6 |
| 13 | Broiler | Nil | Control | 35 | 0-35 | 6 |
| 14 | Broiler | Nil | Control | 36 | 0-35 | 6 |
| 15 | Broiler | Nil | Control | 37 | 0-35 | 6 |
| 16 | Broiler | Nil | Control | 39 | 0-35 | 6 |
| 17 | Broiler | Nil | Control | 42 | 0-35 | 6 |
| 18 | Broiler | Nil | Control | 42 | 0-28 | 6 |

NB-Controls received regular feed without additive

Performance of the LC-MS/MS Assay

Details of the assay methods used for tissue extraction and LC-MS/MS are summarised in Appendix A. The assay of berberine was calibrated initially from simple solutions and subsequently methods for assay after tissue extraction were validated.

Berberine peaks from tissue samples could be detected at concentrations as low as 2 ng/g tissue, but interference due to tissue matrix effects and analyte carryover at 1 ng/g tissue made quantitation of IRP001 difficult at this or lower concentrations. At 5 ng/g (or 4 ng/g on some occasions) the assay could be validated as accurate at ±20% true analyte concentration. In the results section IRP001 levels greater than 5 ng/g are quoted as absolute values, IRP001 levels between 2 and 5 ng/g are considered to be below the LLOQ and outputs indicating values lower than 2 ng/g are considered to be within baseline noise, below the LLOD, and as such are not detectable.

In one embodiment, berberine peaks from tissue samples could be detected at concentrations as low as 1 ng/g tissue, but interference due to tissue matrix effects and analyte carryover at 1 ng/g tissue made quantitation of IRP001 difficult at this or lower concentrations. At 5 ng/g (or 4 ng/g on some occasions) the assay could be validated as accurate at +20% true analyte concentration. Realistically a concentration of less than 2 ng/g can be considered to be below the lower limit of quantitation (LLOQ). The lower limit of peak detection was 1-2 ng/g.

Results

Tissue samples from 3 birds from each feed additive group were received by the Monash analytical team and analysed by LC-MS/MS. A single sample from each control group was assayed.

Table 47 shows mean concentration of berberine and standard deviation determined for each muscle tissue excised from 3 birds in each group. One representative from each control group was assayed and these values were found to be effectively zero, expressed in the results table as below the LLOD "<LLOD", i.e. not detectable.

Broadly speaking the breast tissue samples, upper and lower leg muscle samples were comparable and despite the low concentrations determined the data shows distinct and logical trends. At the low feed additive concentration of 0.03 g/kg feed, mean residues of berberine were not detectable in all cases, with or without washout (i.e. below the LLOD and LLOQ).

At the higher IRP001 concentration of 0.3 g/kg feed, the mean berberine residues after 35 days were in the quantifiable range; 6.1+1.6 for breast, 5.5+3.0 ng/g for lower leg and 11.6+6.6 ng/g for upper leg tissue. In both tissues a progressive washout was evident. Berberine residues fell after 1 and 2 days and after 4 days the berberine levels were below the LLOD.

TABLE 47

Residues of IRP001 chloride in muscle tissues

| Group | Sample Description | days of washout | Animal ID | Mean residue and SD in brackets (n = 3) ng IRP001/g muscle | | |
|---|---|---|---|---|---|---|
| | | | | Breast | Lower leg | Upper leg |
| 1 | 0.03 g/kg IRP001 in feed (0-35 days) Euthanasia on day 35 | 0 | 2, 4 and 6 | <LLOD | <LLOD | <LLOD |
| 2 | 0.03 g/kg IRP001 in feed (0-35 days) Euthanasia on day 36 | 1 | 11, 12 and 13 | <LLOD | <LLOD | <LLOD |
| 3 | 0.03 g/kg IRP001 in feed (0-35 days) Euthanasia on day 37 | 2 | 24, 25 and 26 | <LLOD | <LLOD | <LLOD |
| 4 | 0.03 g/kg IRP001 in feed (0-35 days) Euthanasia on day 39 | 4 | 31, 34 and 35 | <LLOD | <LLOD | <LLOD |
| 5 | 0.03 g/kg IRP001 in feed (0-35 days) Euthanasia on day 42 | 7 | 42, 43 and 45 | <LLOD | <LLOD | <LLOD |
| 6 | 0.03 g/kg IRP001 in feed (0-28 days) Euthanasia on day 42 | 14 | 53, 55 and 56 | <LLOD | <LLOD | <LLOD |
| 7 | 0.3 g/kg IRP001 in feed (0-35 days) Euthanasia on day 35 | 0 | 63, 65 and 66 | 6.1 (1.6) | 5.5 (3.0) | 11.6 (6.6) |
| 8 | 0.3 g/kg IRP001 in feed (0-35 days) Euthanasia on day 36 | 1 | 73, 74 and 75 | 5.7 (2.4) | 3.2* (1.5) | 6.0 (2.9) |
| 9 | 0.3 g/kg IRP001 in feed (0-35 days) Euthanasia on day 37 | 2 | 81, 85 and 86 | 3.6* (2.6) | 3.1* (1.6) | 4.5* (0.6) |
| 10 | 0.3 g/kg IRP001 in feed (0-35 days) Euthanasia on day 39 | 4 | 91, 93 and 96 | <LLOD | 1.1* (0.5) | 1.6* (0.7) |
| 11 | 0.3 g/kg IRP001 in feed (0-35 days) Euthanasia on day 42 | 7 | 102, 104 and 105 | <LLOD | <LLOD | <LLOD |
| 12 | 0.3 g/kg IRP001 in feed (0-28 days) Euthanasia on day 42 | 14 | 111, 113 and 115 | <LLOD | <LLOD | <LLOD |
| 13-18 | Control | 0 | 121, 132, 146, 154, 166 and 171 | <LLOD | <LLOD | <LLOD |

NB < LLOD = below the lower limit of detection (i.e. not detectable)
*asterisks indicate estimates <LLOQ (below the validated lower limit of quantitation)

Table 48 shows mean concentration of berberine and standard deviation determined for liver tissue excised from 3 birds in each group. One representative from each control group was assayed and these values were found to be effectively zero. expressed in the results table as below the LLOD "<LLOD". i.e. not detectable.

TABLE 48

Residues of IRP001 chloride in muscle tissues

| Group | Sample Description | days of washout | Animal ID | Mean residue and SD in brackets (n = 3) ng IRP001/g muscle Liver |
|---|---|---|---|---|
| 1 | 0.03 g/kg IRP001 infeed (0-35 days) Euthanasia on day 35 | 0 | 2, 4 and 6 | <LLOD |
| 2 | 0.03 g/kg IRP001 infeed (0-35 days) Euthanasia on day 36 | 1 | 11, 12 and 13 | <LLOD |
| 3 | 0.03 g/kg IRP001 infeed (0-35 days) Euthanasia on day 37 | 2 | 24, 25 and 26 | <LLOD |
| 4 | 0.03 g/kg IRP001 infeed (0-35 days) Euthanasia on day 39 | 4 | 31, 34 and 35 | <LLOD |

TABLE 48-continued

Residues of IRP001 chloride in muscle tissues

| Group | Sample Description | days of washout | Animal ID | Mean residue and SD in brackets (n = 3) ng IRP001/g muscle Liver |
|---|---|---|---|---|
| 5 | 0.03 g/kg IRP001 infeed (0-35 days) Euthanasia on day 42 | 7 | 42, 43 and 45 | <LLOD |
| 6 | 0.03 g/kg IRP001 infeed (0-28 days) Euthanasia on day 42 | 14 | 53, 55 and 56 | <LLOD |
| 7 | 0.3 g/kg IRP001 infeed (0-35 days) Euthanasia on day 35 | 0 | 63, 65 and 66 | 35.2 (4.0) |
| 8 | 0.3 g/kg IRP001 infeed (0-35 days) Euthanasia on day 36 | 1 | 73, 74 and 75 | 8.0 (3.1) |
| 9 | 0.3 g/kg IRP001 infeed (0-35 days) Euthanasia on day 37 | 2 | 81, 85 and 86 | 7.9 (1.0) |
| 10 | 0.3 g/kg IRP001 infeed (0-35 days) Euthanasia on day 39 | 4 | 91, 93 and 96 | 9.3 (11.1) |
| 11 | 0.3 g/kg IRP001 infeed (0-35 days) Euthanasia on day 42 | 7 | 102, 104 and 105 | 6.5 (5.7) |
| 12 | 0.3 g/kg IRP001 infeed (0-28 days) Euthanasia on day 42 | 14 | 111, 113 and 115 | 3.0* (2.2) |
| 13-18 | Control | 0 | 121, 132, 146, 154, 166 and 171 | <LLOD |

NB
<LLOD = below the lower limit of detection (i.e. not detectable)
*asterisks indicate estimates <LLOQ (below the validated lower limit of quantitation)

Conclusions

All residue levels in muscle tissue (chicken meat) determined in the study were below the nominated safe residue level of 13 ng/g, even when measured after 35 days feeding at 0.3 g berberine/kg feed without a washout period. Residue levels at the lower IRP001 concentration of 0.03 g/kg feed were determined to be less than 2 ng per gram of tissue in all cases and can be considered to be not detectable.

Residue levels in liver were above the limits of quantitation after birds were fed with 0.3 g IRP001/kg feed, were reduced by washout period over 7 days, and reduced to below the limit of quantitation after a 14-day washout. Residue levels in liver after birds were fed with 0.03 g IRP001/kg feed were below the limit of detection before and after washout.

APPENDIX A

Analytical Methods

Berberine was assayed by LC-MS/MS using tetrahydropalmitine as an internal standard.

Preparation of Tissue Samples

1. Approximately 1 g of tissues were cut out and weighed into M-tubes. The tissues were stored in a freezer at −20° C. until they were ready to be homogenized.
2. For each gram of tissue, 2 volumes of MilliQ water was added to the tubes.
3. The M-tubes were attached onto the GentleMACS homogenizer and the program method RNA_01_01 (60 seconds) was run 3 times to ensure that the tissue was completely homogenized.
4. The tissue homogenates were distributed into Eppendorf tubes in 200 μL aliquots.
5. To each 200 μL aliquot of tissue homogenate, 10 μL internal standard solution was added, followed by 600 μL of 100% methanol. Samples were vortexed at maximum setting for 3×10 seconds and then centrifuged at 10,000 rpm for 3 minutes.
6. 100 μL of supernatant was transferred into LC vials for analysis.

Method Validation

1. The method was validated for selectivity, linearity, LLOQ, accuracy, precision, recovery, stability and matrix effect.
2. Selectivity was assessed by preparing samples spiked with individual analyte at concentrations up to 500 ng/g with 5 replicates each. The peak signal was compared with the calibration standards (spiked with analytes) to ensure that there was no interference.
3. To evaluate LLOQ, the 5 ng/g and 10 ng/g standards were prepared at 6 replicates. The LLOQ was determined at the lowest concentration of the calibration curve which both precision and accuracy were ≤20%.
4. For an indication of accuracy and precision, 4 concentration levels of 20, 50, 100 and 500 ng/g were prepared (5 replicates each). Accuracy was denoted as bias (%) from the nominal concentration and precision was denoted as the relative standard deviation (RSD) of the replicates.
5. To evaluate recovery, matrix recovery samples were prepared by extracting blank tissue and then spiking with the analyte solutions to give various concentration levels up to 500 ng/g (5 replicates each). The recovery was defined by the ratio of the mean peak area of extracted samples to the mean peak area of matrix recovery samples.

6. To evaluate bench-top stability, 4 concentration levels of 20, 50, 100 and 500 ng/g were prepared at 5 replicates each, where they were kept at room temperature for 30 minutes prior to extraction. The mean peak area was compared to that of freshly-prepared standards.

7. To evaluate matrix effect (ME), 4 concentration levels of 20, 50, 100 and 500 ng/g in neat solution were prepared at 5 replicates each. ME was defined as the ratio of the mean peak area of recovery samples to that of the neat standard samples.

TABLE 49

| LCMS Assay conditions | |
|---|---|
| Instrument | Shimadzu LCMS 8050-2 |
| Mobile phase | A: 0.1% formic acid in MilliQ water B: 0.1% formic acid in methanol |
| Column | Phenomenex Kinetex 2.6 μm × B-C18 100 Angstrom 50 × 3 mm |
| Column Temperature | 40° C. |
| Injection Volume | 1 μl |
| Run time | 4.5 min |
| Flow Rate | 0.4 mL/min |
| Needle wash solution | 90:10:1 Methanol-Water-Acetic acid |
| Elution mode | Gradient |

| Gradient conditions: | |
|---|---|
| Time (minutes) | % B |
| 0.01 | 10 |
| 0.5 | 30 |
| 3 | 70 |
| 3.2 | 95 |
| 3.8 | 95 |
| 4.0 | 10 |
| 4.5 | 10 |

APPENDIX B

Compliance

This tissue residue depletion study was conducted according to the agreed protocol utilizing SOPs and good scientific practice.

Study Design a. Experimental Unit: Both the experimental and observational unit was the individual animal. The statistical unit was the treatment group.

b. Animal Model: Feed intake, daily water consumption, weight change, mortality and marker residue in tissues were used as outcome parameters.

C. Inclusion Criteria: Animals were selected for the study if they met the criteria outlined in below.

d. Exclusion and Removal Criteria: Animals that, on receipt, are debilitated, suffering from disease, injury, or otherwise unsuitable for inclusion in the study, in the opinion of the Investigator, were excluded.

Subsequent to selection, animals that may be deemed unsuitable for continuation in the study will only be removed with the documented concurrence of the Sponsor or Investigator. The reason for any removal will be fully documented and justified in the raw data and Study Report. Any animal that is removed from the study will receive appropriate veterinary care.

e. Allocation: Broiler Chicks: On receival the one hundred and eighty (180) broiler chicks that met the inclusion criteria were sequentially allocated as they were removed from the transport container to eighteen (18) individual treatment groups, each of ten (10) birds. The method of allocation and randomisation was described in the raw data and Study Report.

f. Blinding: Not applicable.

Investigational Veterinary Product (IVP)

All formulation details including batch number, expiry date, receipt and usage were recorded.

a. Investigational Veterinary Product: IRP001 Cl as 100% IRP001 Cl.

b. Source: The IVP was supplied by the Sponsor.

c. Storage: The IVP was stored at ambient temperature in a temperature designated area. The storage location and conditions of the IVP were recorded.

d. Safety: A SDS or its equivalent (if available) was provided by the Sponsor.

e. Assays: A Certificate of Analysis (if available) was provided for the IVP.

f. Drug Disposal: The disposal of all remaining IVP was recorded.

Treatment a. Dose Calculation: Doses were based on fixed concentrations of IRP001 Cl in feed (0.03 or 0.1 g/kg IRP001 Cl).

b. Dose Preparation: Powdered IRP001 Cl was incorporated with raw commercial feed ingredients then thoroughly mixed in, for example a "concrete mixer" type apparatus, to provide the final concentrations in feed as outlined.

c. Method of Dose Administration: Study animals were dosed according to the treatment regime detailed in Table 49 below. Medicated feed was provided to chickens in the relevant treatments ad libitum as their sole source of feed.

TABLE 50

| Treatment regime-feed conversion ratio | | | | | | |
|---|---|---|---|---|---|---|
| Grp. | Bird type | Treatment | IVP concentration in feed g/kg | Euth*. (Day) | Trt. In feed Days | No. Animals |
| 1 | Broiler | IVP | 0.03 | 35 | 0-35 | 10 |
| 2 | Broiler | IVP | 0.03 | 36 | 0-35 | 10 |
| 3 | Broiler | IVP | 0.03 | 37 | 0-35 | 10 |
| 4 | Broiler | IVP | 0.03 | 39 | 0-35 | 10 |
| 5 | Broiler | IVP | 0.03 | 42 | 0-35 | 10 |
| 6 | Broiler | IVP | 0.03 | 42 | 0-28** | 10 |
| 7 | Broiler | IVP | 0.3 | 35 | 0-35 | 10 |
| 8 | Broiler | IVP | 0.3 | 36 | 0-35 | 10 |
| 9 | Broiler | IVP | 0.3 | 37 | 0-35 | 10 |
| 10 | Broiler | IVP | 0.3 | 39 | 0-35 | 10 |

TABLE 50-continued

Treatment regime-feed conversion ratio

| Grp. | Bird type | Treatment | IVP concentration in feed g/kg | Euth*. (Day) | Trt. In feed Days | No. Animals |
|---|---|---|---|---|---|---|
| 11 | Broiler | IVP | 0.3 | 42 | 0-35 | 10 |
| 12 | Broiler | IVP | 0.3 | 42 | 0-28** | 10 |
| 13 | Broiler | IVP | Control | 35 | 0-35 | 10 |
| 14 | Broiler | IVP | Control | 36 | 0-35 | 10 |
| 15 | Broiler | IVP | Control | 37 | 0-35 | 10 |
| 16 | Broiler | IVP | Control | 39 | 0-35 | 10 |
| 17 | Broiler | IVP | Control | 42 | 0-35 | 10 |
| 18 | Broiler | IVP | Control | 42 | 0-28** | 10 |

*Euthanasia
**Note:
Medicated feed is withdrawn from Groups 6 and 12 on Day 28 to allow a 14 day washout period for these groups.

Schedule of Events

TABLE 51

Schedule of events

| Approx. Study Day | Event |
|---|---|
| Pre-study | Receipt of formulation. Receipt of Animal Ethics Committee approval. |
| 0 | Broiler chicks hatched. Broiler chicks transported and placed into temperature controlled floor pens. Birds weighed (by treatment group). Commence twice daily health observations. |
| Days 0-49 | Weigh daily feed added and calculate daily feed intake by treatment group. Measure daily water volume and calculate daily water intake by treatment group. |
| 7, 14, 21, 28 and 35 | Weigh all birds - Groups 1 through Group 18 inclusive. Record individual bird bodyweight. |
| Day 28 | Groups 6 and 12. Cease medicated feed thus allowing 14 day washout period when sacrificed at Day 42. |
| Day 35 | Weigh all birds - Groups 1 through Group 18 inclusive. Withdraw medicated feed from all groups. |
| 9.00am | At the point of medicated feed withdrawal euthanise, conduct individual clinical examination and gross visual pathological assessment on the six heaviest birds in Groups 1, 7 and 13. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 36 9.00am | Euthanise, conduct individual clinical examination and gross visual pathological assessment on the six heaviest birds in Groups 2, 8 and 14. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 37 9.00am | Euthanise, conduct individual clinical examination and gross visual pathological assessment on the six heaviest birds in Groups 3, 9 and 15. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 39 9.00am | Euthanise, conduct individual clinical examination and gross visual pathological assessment on the six heaviest birds in Groups 4, 10 and 16. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 42 9.00am | Euthanise, conduct individual clinical examination and gross visual pathological assessment on the six heaviest birds in Groups 5, 11 and 17. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |
| Day 42 9.00am | Euthanise, conduct individual clinical examination and gross visual pathological assessment on the six heaviest birds in Groups 6, 12 and 18. Collect tissues - liver, kidney, breast muscle (1) leg muscle (2) [upper and lower thigh] and skin (feathers removed, intact with any subcutaneous fat). Store frozen duplicate samples of tissues (<10 degrees Celsius). |

Test System

Animal details were recorded in the raw data. That is: Species, broiler chickens: Number, 180; Source, commercial (one batch of 90): Age, one day old.

Animal Management a. Animal Welfare: Study animals were managed similarly and with due regard for their welfare. Study animals were observed according to Animal Ethics Committee (AEC) requirements and a "Record of Animal Care" was completed.

b. Health Management: Any routine prophylactic treatments were given as soon as possible, if necessary, and recorded (product name, batch number, expiry date, dose, route and date(s) of administration).

The study animals were observed twice daily according to the standard operating protocol (SOP) in place commencing on Day 0. Any health problem that requires further examination was recorded.

All health problems and adverse events must be reported to the Investigator within one working day. Any adverse event characterised by the Investigator as product related, results in death, is life-threatening, involves a large number of animals, or is a human adverse event, must be recorded and reported to the Sponsor and AEC within one working day.

Normal veterinary care and procedures may be performed and are described in the raw data. Concurrent medications may be administered for standard management practice and humane reasons, with prior approval from the Investigator, and Sponsor (if relevant). No treatments similar to the IVP are administered. All concurrent medications are recorded giving identity of materials used (product name, batch number and expiry date), animal ID(s), the reason for use, route of administration, dose and the date(s) administered, and are included in the raw data (Trial Log) and the Study Report.

If an injury or illness results in euthanasia or death of a study animal, this should be recorded and a post-mortem conducted, if possible, by a veterinarian. A "Post Mortem Report", including the probable cause of death, is included in the raw data.

All health problems, adverse events and animal mortality, including their relationship to treatment, were included in the Study Report.

c. Housing: Chickens were kept in purpose built chicken floor pens by treatment group in two separate and discrete controlled environment rooms at an approved animal facility. One room houses all unmedicated Groups 13 to 18 inclusive birds with the second room housing all medicated birds—Groups 1 to 12 inclusive. Each pen has a floor space of approx. 1.5 m². Chickens were raised on litter according to normal commercial practice.

There were 18 floor pens, 10 chickens per pen up to Day 49. The maximum chicken weight of each pen at study conclusion is well below the recommended maximum of 40 kg/m² for meat chickens in the Australian Code of Practice.

Note—birds in Groups 13 to 18 inclusive (untreated control animals) were maintained in a similar, but physically separate isolation room to medicated Groups 1 to 12 birds thus ensuring no cross contamination during the study.

d. Experimental diets: A formulated commercial starter then grower ration was fed throughout the study. A copy of a feed bag label, or equivalent, showing feed composition, was included in the raw data.

e. Feed and Water Intake: Weigh and record daily feed added and calculate daily feed intake by treatment group. Measure and record daily water volume and calculate daily water intake by treatment group.

f. Animal Disposal: Study animals were humanely euthanised according to AEC approval and recorded at the intervals as outlined in the Schedule of Events (Table 50).

Study Procedures a. Trial Log: All scheduled and unscheduled events during the study were recorded.

Assessment of Effects a. Body Weights: Chickens were weighed on Days 0 (Group weight) and 7, 14, 21, 28 and 35 days-individual animal weights were recorded. Weigh scales were checked pre- and post-weighing with calibrated test weights and recorded. Body weights at study termination were compared between groups to determine treatment effects (if any).

b. Examinations: Individual clinical examinations were performed on euthanasia at the time of gross pathology and tissue collection. Clinical examinations were recorded. Digital still images may be recorded as appropriate.

c. Observations: Birds were inspected twice daily for general well-being, typically prior to 8 am of a morning, and after 4 μm of an afternoon. Thus a typical interval between observations would be 9 hours during the day, and 15 hours overnight. Birds showing abnormal clinical signs were recorded, observed closely and euthanized if deemed to be suffering significantly (e.g. marked depression with low likelihood of recovery) by the Investigator.

d. Necropsy Examinations: All birds were euthanized and necropsied between Days 35 and 49 as per schedule—Table 14.

e. Gross Pathology: All chickens from all Group 1 through 18 were necropsied and examined for gross visual pathological changes which were described and scored as appropriate by individual bird.

f. Tissue Residue Analysis: Duplicate representative samples of liver, kidney, breast muscle (1), leg muscle (2) [upper and lower thigh] and entire skin with fat intact was collected and stored frozen (<10 degrees Celsius) from the six (6) heaviest birds in each group (Groups 1 to 18 inclusive) as per schedule, Table 50, for subsequent marker residue analysis. Groups 13 to 18 birds shall be sacrificed at Day 35 as untreated control birds with tissues collected for tissue assay requirements.

Samples were labelled with adhesive labels listing the study number, animal ID, time point, date, sample type and replicate.

For residue analysis, samples were thawed and a known weight of tissue (approximately 1 g) homogenized in 2 ml water. Samples were centrifuged and a known volume of the supernatant removed for analysis by LC-MS/MS.

TABLE 52

Analytical matrix

| Sacrifice Time (Days) | Group | IRP001 HCl (Marker residue) | | | | | |
|---|---|---|---|---|---|---|---|
| | | Liver | Kidney | Breast Muscle | Upper leg Muscle | Lower leg Muscle | Skin (entire) |
| 0 | 1 | ☑ | ☑ | ☑ | ☑ | ☑ | ☑ |
| 1 | 2 | ☑ | ☑ | ☑ | ☑ | ☑ | ☑ |
| 2 | 3 | ☑ | ☑ | ☑ | ☑ | ☑ | ☑ |
| 4 | 4 | ☑ | ☑ | ☑ | ☑ | ☑ | ☑ |
| 7 | 5 | ☑ | ☑ | ☑ | ☑ | ☑ | ☑ |
| 14 | 6 | ☑ | ☑ | ☑ | ☑ | ☑ | ☑ |
| 0 | 7 | ☑ | ☑ | ☑ | ☑ | ☑ | ☑ |
| 1 | 8 | ☑ | ☑ | ☑ | ☑ | ☑ | ☑ |
| 2 | 9 | ☑ | ☑ | ☑ | ☑ | ☑ | ☑ |
| 4 | 10 | ☑ | ☑ | ☑ | ☑ | ☑ | ☑ |
| 7 | 11 | ☑ | ☑ | ☑ | ☑ | ☑ | ☑ |
| 14 | 12 | ☑ | ☑ | ☑ | ☑ | ☑ | ☑ |
| 0 | 13 | ☑ | ☑ | ☑ | ☑ | ☑ | ☑ |
| 1 | 14 | ☑ | ☑ | ☑ | ☑ | ☑ | ☑ |
| 2 | 15 | ☑ | ☑ | ☑ | ☑ | ☑ | ☑ |

TABLE 52-continued

| | Analytical matrix | | | | | |
|---|---|---|---|---|---|---|
| Sacrifice | IRP001 HCl (Marker residue) | | | | | |
| Time (Days) | Group | Liver | Kidney | Breast Muscle | Upper leg Muscle | Lower leg Muscle | Skin (entire) |
| 4 | 16 | ☑✢ | ☑✢ | ☑✢ | ☑✢ | ☑✢ | ☑✢ |
| 7 | 17 | ☑✢ | ☑✢ | ☑✢ | ☑✢ | ☑✢ | ☑✢ |
| 14 | 18 | ☑✢ | ☑✢ | ☑✢ | ☑✢ | ☑✢ | ☑✢ |
| | Total | 31 | 31 | 21 | 46 | 46 | 175 |

✢ To be analysed if required for assay validation and verification.

g. Sample Storage, Transfer & Disposal: Sample storage, transfer and disposal were recorded. Replicate 1 tissue samples were shipped frozen on wet ice to the Analytical Laboratory at times outlined in Section 10. Samples were transferred according to the standard operating protocol (SOP) with an accompanying temperature data logger and frozen water vial. Replicate 2 tissue samples were retained frozen for a period of 6 months after the last sample collection time-point. Beyond that point they may be discarded at the study site's discretion unless specifically requested not to by the Sponsor's Representative.

Statistical Analysis

Methods were documented in the Study Report.

Data Records

Protocol specifications are to supersede facility SOPs. Study forms may be added or amended as required during the study without the need for a Protocol Amendment or Deviation.

a. Protocol Approval: The Protocol is to be approved and signed by all relevant personnel (see page 1) prior to study start.

b. Amendments/Deviations: An amendment is a change or modification of the Protocol made prior to execution of the changed or modified task. Amendments must state the reason for the change and have documented authorisation from the Sponsor. The amendment must be signed by the Investigator, and the Sponsor.

Deviations from this Protocol or applicable SOPs are to be documented, signed and dated by the Investigator at the time the deviation(s) are identified. An assessment on the impact on the overall outcome or integrity of the study is to be made. Deviations must be communicated to the Sponsor as soon as practically possible.

All Protocol amendments and deviations are to be recorded accordingly and numbered sequentially based on the date of occurrence or date of identification.

c. Notes to File: Notes to File are to be recorded accordingly to clarify events or circumstances that may not otherwise be apparent from the raw data. Notes to File must be communicated to the Sponsor as soon as practically possible.

d. Change of Study Personnel: Change of the study Investigator, or other responsible study personnel, is to be recorded accordingly.

e. Raw Data: All original raw data pages were paginated, identified with the study number and signed and dated by the person making the observation and by the person recording the information.

f. Communication Log: The Investigator maintained copies of all correspondence relating to the study. Any telephone conversations that resulted in a change in the documentation, design, conduct, or reporting of the study, were recorded.

g. Permits: The study detailed in this Protocol is to be covered by government agency permit (for example an APVMA small trial permit).

Study Report

A Study Report was prepared by the Investigator, or designee. Data listings of each variable measured was included. The study Investigator's Compliance Statement was included in the Study Report. The original signed Study report with raw data and Statistical Report appended was submitted to the Sponsor and archived.

Example 8

This study evaluates the safety of IRP001 chloride in broilers through examination of histology.

Summary and Conclusion

Histology results are shown in Table 53.

TABLE 53

| | | Histology | | | | |
|---|---|---|---|---|---|---|
| Indexes Treatment | Product | g/kg | Pen | Cumulative Pathology | Enteritis | Coccidia |
| 1 | Nil | 0 | 1 | 10.8 | 8.2 | 2.6 |
| 2 | IRP001 | 0.05 | 2 | 9.6 | 6.4 | 3.2 |
| 3 | IRP001 | 0.5 | 3 | 7.6 | 6.0 | 1.6 |
| 4 | IRP001 | 1 | 4 | 9.2 | 8.2 | 1.0 |

From above, Cumulative Pathology and Enteritis scores were equal or lower than the control Treatment 1 Nil group. In conclusion, all gastrointestinal tract (GIT) histologic lesions identified were within normal limits for broiler chickens in a production environment. All liver histologic lesions identified were within normal limits for broiler chickens in a production environment.

Experimental Description and Protocols

Study Objective

The objective of this study was to test the general safety of IRP001 chloride in broilers reared to market weight by examination of histology.

Experimental Design

The experiment consisted of the following treatments (1 pen per treatment, Table 54).

TABLE 54

| | Treatments | | | |
|---|---|---|---|---|
| TRT | Bird type | Start Day | In-feed medication | G/Kg |
| 1 | Broiler | 0 | Nil | 0.0 |
| 2 | Broiler | 0 | IRP001 | 0.05 |
| 3 | Broiler | 0 | IRP001 | 0.5 |
| 4 | Broiler | 0 | IRP001 | 1.0 |

Floor Pen Description and Management

Birds were kept in a pen having an area of 4×10=40 ft$^2$, with clean wood shavings as bedding with a thickness of approximately 4 inches. The pen had 5 feet high side walls with a bottom 1 ½ feet being of solid wood to prevent bird migration.

The temperature of the building was monitored. Environmental conditions during the trial (temperature) were appropriate (optimum) to the age of the animals. Illumination was provided by fluorescent bulbs placed above the pens. The diets were provided ad libitum in one tube-type feeder per pen. From D0 until D7, feed was also supplied on a tray placed on the litter of each pen. Water was provided ad libitum from one Plasson drinker per pen.

Standard floor pen management practices were used throughout the experiment. Animals and housing facilities were inspected twice daily, observing and recording the general health status, constant feed and water supply as well as temperature, removing all dead birds, and recognizing unexpected events. Birds found dead during the study were noted on the Daily Mortality Record, and were not replaced. Pen number, the date of mortality, sex, weight, and diagnosis were recorded.

Birds

Day of hatch male Cobb chicks were obtained and ten male broiler chicks were placed in each pen. Accountabilities of all test animals and any extra birds were recorded on animal disposition form. The birds were sexed at the hatchery. The breeder flock history and vaccination record at the hatchery were recorded. Bird weights by pen were recorded on D0 and 42.

Feed

All feeds were manufactured and fed as crumbles/pellets.

Quantities of all basal feed and items used to prepare treatment batches were documented. Each batch of feed was mixed and bagged separately. Each bag was identified with the study number, date of mix, type of feed, and correct treatment number. Complete records of feed mixing and test article inventories were maintained.

Feed Samples

Treatment feed samples (~150 g each) were collected and blended: one each from the beginning, middle, and end of each batch of treatment diet. Samples are retained until directed to ship or discarded 2 months post submission of report.

Feeding Schedule

All weights were by pen. Treatment Starter feed was fed from D0 to 21. On D21, non-consumed Starter was weighed by pen and discarded. Grower feed was issued and fed until D35. On D35, non-consumed Grower was weighed by pen and discarded. Finisher feed was fed until D42. On D42, non-consumed Finisher was weighed by pen and discarded.

Diets

Diet specifics are shown in Table 55 and Table 56.

TABLE 55

| Nutrition | | | |
|---|---|---|---|
| | Commercial grade diet | | |
| | Starter | Grower | Finisher |
| ME, kcal/kg | 3,067 | 3,130 | 3,165 |
| Crude protein, % | 20.96 | 20.03 | 19.16 |
| Dig. Lysine, % | 1.20 | 1.10 | 1.00 |
| Dig. Methionine, % | 0.61 | 0.52 | 0.48 |
| Dig. TSAA, % | 0.90 | 0.80 | 0.75 |
| Dig. Threonine, % | 0.81 | 0.68 | 0.65 |
| Calcium, % | 0.90 | 0.85 | 0.8 |
| Avail. phosphorus, % | 0.42 | 0.42 | 0.4 |

The main ingredients used were corn, soybean meal and animal by product.

TABLE 56

| Ingredients | | | |
|---|---|---|---|
| | Commercial grade diet (%) | | |
| Ingredients | Starter | Grower | Finisher |
| CORN, YELLOW, GRAIN | 64.675 | 66.460 | 68.491 |
| SOYBEAN MEAL DEHULLED, SOLVENT | 29.020 | 26.663 | 24.677 |
| Ampro 55 (animal by-product 55% protein) | 2.500 | 3.000 | 3.000 |
| CALCIUM CARBONATE | 0.886 | 0.735 | 0.684 |
| FAT, VEGETABLE | 0.883 | 1.485 | 1.702 |
| DICALCIUM PHOSPHATE. | 0.706 | 0.612 | 0.500 |
| SALT, PLAIN (NaCl) | 0.439 | 0.435 | 0.436 |
| Methionine MHA | 0.358 | 0.259 | 0.221 |
| L - LYSINE | 0.273 | 0.208 | 0.145 |
| L-Threonine 98.5 | 0.103 | 0.000 | 0.000 |
| Trace Mineral[1] | 0.075 | 0.075 | 0.075 |
| Vitamin premix [2] | 0.065 | 0.050 | 0.050 |
| ronozymep-(ct) | 0.019 | 0.019 | 0.019 |

[1]Vitamin mix provided the following (per kg of diet): thiamin•mononitrate, 2.4 mg; nicotinic acid, 44 mg; riboflavin, 4.4 mg; D-Ca pantothenate, 12 mg; vitamin $B_{12}$ (cobalamin), 12.0 ug; pyridoxine•HCL, 4.7 mg; D-biotin, 0.11 mg; folic acid, 5.5 mg; menadione sodium bisulfite complex, 3.34 mg; choline chloride, 220 mg; cholecalciferol, 27.5 ug; trans-retinyl acetate, 1,892 ug; all-rac α tocopheryl acetate, 11 mg; ethoxyquin, 125 mg.
[2] Trace mineral mix provided the following (per kg of diet): manganese ($MnSO_4$•$H_2O$), 60 mg; iron ($FeSO_4$•$7H_2O$), 30 mg; zinc (ZnO), 50 mg; copper ($CuSO_4$•$5H_2O$), 5 mg; iodine (ethylene diamine dihydroiodide), 0.15 mg; selenium ($NaSeO_3$), 0.3 mg.

The basal feed did not contain any probiotic/prebiotic feed additives, NSPases, coccidiostats or antibiotic growth promoter. All diets contained phytase.

Histological Samples

On the day of study completion (D42), five birds from each pen were humanly euthanized and upper, mid and lower gut sections plus liver lobe were collected and stored in neutral buffered formalin. Theses samples were shipped for analysis.

Procedures

1. Standard floor pen management practices were used throughout the experiment. The temperature of the building was monitored. Environmental conditions during the trial (temperature) were appropriate (optimum) to the age of the animals. Illumination was provided by fluorescent bulbs placed above the pens. The lighting scheme was 24 hours of light from D0 to D14, then 18 hours of light to D42.
2. The diets were provided ad libitum in one tube-type feeder per pen. From day 1 until day 7 feed was also supplied on a tray placed on the litter on each pen.
3. Feed and watering method. ad libitum.
4. Environmental control. There was ambient humidity.
5. Disease control. No concomitant drug therapy was used during the study.
6. Bird identification. The pen was the unit of measure. Pen security prevented bird migration.
7. Twice daily observations were recorded during the study for general flock condition. Observations included were the availability of feed and water, temperature control, and any unusual conditions. The birds were watched closely for any abnormal reactions.

Data Entry and Analysis

Source data were entered with indelible ink. Entries were legible, signed or initialed, and dated by the person making the observation entry. Each sheet of source data was signed by the person(s) attributed to the data. Any mistakes or changes to the source data were initialed and dated and a correction code or statement added as to why the changes were made.

Disposal of Birds and Feed

All birds and feed were buried in following SOPs. Records of disposition were included in the source data.

Locations of Source Data

The original source data sheets and the final report were sent to Sponsor. An exact copy of the file and the final report were retained.

Example 9

This study measures the anticoccidial efficacy/sensitivity of IRP001 against a mixture of Eimeria acervulina, E. maxima, and E. tenella.

Experimental Design

The experiment consisted of 72 cages starting with 8 male chicks. The treatments were replicated in 6 blocks, randomized within blocks of 12 cages each. A randomization procedure for pen assignment for treatments and blocks was provided by Southern Poultry Research, Inc. (SPR, Athens, GA 30607) who conducted the study for the Sponsor.

Treatment groups are set out in Table 57.

TABLE 57

Treatment groups

| Trt | Description |
| --- | --- |
| 1 | No Treatment/No Challenge |
| 2 | No Treatment/Challenge |
| 3 | IRP001-0.03 g/kg |
| 4 | IRP001-0.1 g/kg |

Management
1. The facility was checked thoroughly to assure that all cages had water and feed available in each cage. The building temperature was maintained as appropriate for the age of the birds.
2. Even, continuous illumination was provided by fluorescent lamps hung vertically along the wall.
3. Feed and water were provided ad libitum.
4. Cages were checked twice daily. Observations including availability of feed, water, temperature and any unusual conditions were recorded.
5. When mortality birds were removed from cages, the cage number, date, weight of the bird, sex and probable cause of death were recorded in the Daily Mortality Record.

Experimental Ration

An unmedicated commercial starter ration compounded with feedstuffs commonly used in North Georgia was formulated. This ration (in mash form) was fed ad libitum from the date of chick arrival until completion of the study. Experimental diets were prepared from a uniform basal diet. Quantities of all basal feed and test articles used to prepare treatment batches were documented. Treatment diets were mixed to assure a uniform distribution of test article. The mixer was flushed between medicated treatment diets. The feed was transferred to building #2 and distributed among cages of the same treatment.

Feed issued and remaining on DOT 14 and 20 were weighed.

Feed Samples

One each from the beginning, middle, and end of each batch of treatment diet was collected and mixed to form a composite sample. One sample was taken from the composite for each treatment and held until completion of study.

Animals

Day of hatch male chicks (Cobb 500) were obtained for the study. The strain, source, and vaccination record were recorded. Upon arrival, chicks were assigned to treatment battery cages. Chicks (DOT 0) was grouped into sets of 8, weighed, and placed into assigned cage. The total number of birds entering the test was 576. Accountabilities of all birds were recorded in the source data.

Birds were weighed by cage on DOT 0, 14, and 20.

Oocysts Inoculation

Coccidial oocyst inoculation procedures are described in SPR SOP. On DOT 14 of the study all T1 birds received 1 ml of distilled water by oral pipette (p.o.). All other birds received the coccidial inoculum diluted to a 1 ml volume (p.o.). The inoculum was a mixture of Eimeria acervulina (100,000 oocysts/bird), E. maxima (50,000 oocysts/bird), and E. tenella (75,000 oocysts/bird).

Oocysts Per Gram Fecal Material

On DOT 19, all fecal collection pans were cleaned. On DOT 20, from all treatments cages, samples of the feces were collected. Feces collected from each cage were thoroughly mixed and prepared for fecal floatation. Each sample was examined for the number of ooycsts per gram fecal material.

Lesion Scoring

On DOT 20, all birds per cage were lesion scored. The Johnson and Reid, 1970 method of coccidiosis lesion scoring was used to score the infected region(s) of the intestine (Johnson J, Reid WM. "Anticoccidial drugs: lesion scoring techniques in battery and floor-pen experiments with chickens" Exp Parasitol. 1970 August; 28 (1): 30-6).

Data Collected
1. The following schedule was followed for data collection:
    DOT 0 Feed issued, birds weighed by cage and allocated.
    DOT 14 Birds inoculated with coccidia (except T1).
    DOT 19 Dropping pans cleaned
    DOT 20 Birds weighed by cage. Remaining feed weighed. Fecal material collected by cage. All birds coccidia lesion scored.
2. Death weights recorded with autopsy to determine probable cause of death.

Clinical observations, twice daily, were recorded.

Disposal of Test Animals and Feed

All birds and remaining feed were buried in SPR pit according to SPR SOPs. Records of disposal were included in the source data.

Data Analysis

Mean for group weight gain, feed consumption, feed conversion, opgs, coccidia lesion scores, and mortality were calculated. The data were analyzed according to the SPR standard operating procedures for data analysis. The raw data were analyzed using STATIX program LSD test. P value 0.05 was used to separate means when ANOVA F values are significant (p≤0.05).

Records

Final Report and original source data sheets were sent to the Sponsor. Southern Poultry Research, Inc. maintained an exact copy.

Results

Results for Feed Intake, adjusted feed conversion ratio (Adj. FCR), weight gain (Wt. Gain), Mortality (% Cocci Mort.); lesion scores; and fecal oocyst counts (for *Eimeria acervulina* (*E. acer*), *E. maxima*, and *E. tenella*) are shown in Table 58.

TABLE 58

Example 9 Results

| Day 0-20 Treatment | Feed Intake | Adj. FCR | Wt. Gain (kg) | % Cocci Mort. |
|---|---|---|---|---|
| 1) Nonmed, noninfect | 4.929ab | 1.597b | 0.403a | 0.0b |
| 2) Nonmed, infected | 4.718ab | 1.682ab | 0.363abc | 4.2a |
| 3) IRP001, 0.03 g/kg | 4.336ab | 1.882a | 0.303c | 0.0b |
| 4) IRP001, 0.10 g/kg | 4.504ab | 1.692ab | 0.339bc | 0.0b |
| Day 14-20 (challenge period) | | | | |

| Treatment | | | | |
|---|---|---|---|---|
| 1) Nonmed, noninfect | 2.767a | 1.702b | 0.214a | |
| 2) Nonmed, infected | 2.526ab | 2.082a | 0.156bc | |
| 3) IRP001, 0.03 g/kg | 2.293b | 2.220a | 0.137bc | |
| 4) IRP001, 0.10 g/kg | 2.482ab | 1.990a | 0.156bc | |

| Lesion Scores Treatment | E. acer. | E. maxima | E. tenella | Average |
|---|---|---|---|---|
| 1) Nonmed, noninfect | 0.0d | 0.0e | 0.0e | 0.0d |
| 2) Nonmed, infected | 2.7a | 2.3a | 1.6a | 2.2a |
| 3) IRP001, 0.03 g/kg | 2.3b | 1.8bc | 1.2ab | 1.8b |
| 4) IRP001, 0.10 g/kg | 2.1bc | 1.5bcd | 0.8bcd | 1.5bc |

TABLE 58-continued

Example 9 Results

| Oocysts/Gram Fecal Treatment | E. acer. | E. maxima | E. tenella | Total |
|---|---|---|---|---|
| 1) Nonmed, noninfect | 0b | 0b | 0c | 0c |
| 2) Nonmed, infected | 50105a | 1898ab | 19821a | 71824a |
| 3) IRP001, 0.03 g/kg | 19486b | 1206ab | 14707ab | 35398abc |
| 4) IRP001, 0.10 g/kg | 18079b | 1809ab | 13300ab | 33187bc |

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

The invention claimed is:

1. A method for the treatment of an infectious disease in a pig caused by an antibiotic-resistant bacterial strain from the genus *Lawsonia*, wherein the method comprises administering an effective amount of a composition comprising a berberine alkaloid and piceid, to the pig for a period of 1-6 weeks.

2. The method according to claim 1, wherein the pig is a food producing animal.

3. The method according to claim 1, wherein the infectious disease is diarrhoea.

4. The method according to claim 1, wherein the infectious disease is caused by *Lawsonia intracellularis*.

5. The method according to claim 4, wherein the infectious disease is represented by a group of conditions selected from: porcine intestinal adenopathy, necrotic enteritis, regional ileitis and proliferative haemorrhagic enteropathy.

6. The method according to claim 1, wherein the composition is in the form of an animal feed comprising 0.0001 to 0.2% w/w of berberine alkaloid and piceid.

7. The method according to claim 1, wherein the composition is in the form of an animal feed comprising 0.003 to 0.2% w/w of berberine alkaloid and piceid.

8. The method according to claim 1, wherein the composition further comprises baicalin.

9. The method according to claim 8, wherein the composition is in the form of an animal feed comprising 0.1% w/w berberine alkaloid, 0.005% w/w piceid and 0.00003% w/w baicalin.

* * * * *